(12) United States Patent
Strobel et al.

(10) Patent No.: US 8,304,438 B2
(45) Date of Patent: Nov. 6, 2012

(54) HETEROARYLACRYLAMIDES AND THEIR USE AS PHARMACEUTICALS

(75) Inventors: Hartmut Strobel, Frankfurt am Main (DE); Paulus Wohlfart, Frankfurt am Main (DE); Heinz-Werner Kleemann, Frankfurt am Main (DE); Gerhard Zoller, Schöneck (DE); David William Will, Frankfurt am Main (DE)

(73) Assignee: Sanofi, Paris (FR)

( * ) Notice: Subject to any disclaimer, the term of this patent is extended or adjusted under 35 U.S.C. 154(b) by 555 days.

(21) Appl. No.: 12/486,117

(22) Filed: Jun. 17, 2009

(65) Prior Publication Data
US 2010/0016272 A1    Jan. 21, 2010

Related U.S. Application Data

(63) Continuation of application No. PCT/EP2007/010709, filed on Dec. 8, 2007.

(30) Foreign Application Priority Data

Dec. 20, 2006 (EP) .................................... 06026397

(51) Int. Cl.
*C07D 401/06* (2006.01)
*A61K 31/44* (2006.01)

(52) U.S. Cl. ........ 514/357; 514/332; 514/334; 514/336; 546/255; 546/268.4; 546/280.1; 546/336

(58) Field of Classification Search .................... None
See application file for complete search history.

(56) References Cited

U.S. PATENT DOCUMENTS

| | | | |
|---|---|---|---|
| 5,198,014 A | 3/1993 | Maravetz | |
| 5,250,504 A | 10/1993 | Maravetz | |
| 5,438,033 A * | 8/1995 | Drumm et al. | 504/130 |
| 6,369,002 B1 | 4/2002 | Kunz et al. | |
| 6,897,220 B2 * | 5/2005 | Delorme et al. | 514/275 |
| 2003/0018025 A1 | 1/2003 | Thurkauf et al. | |
| 2004/0121994 A1 | 6/2004 | Anderson et al. | |

FOREIGN PATENT DOCUMENTS

| | | |
|---|---|---|
| EP | 0210782 | 2/1987 |
| EP | 0402246 | 12/1990 |
| EP | 0489660 | 6/1992 |
| EP | 1340749 | 9/2003 |
| GB | 1237194 | 6/1971 |
| JP | 5345772 | 12/1993 |
| WO | WO 96/16040 | 5/1996 |
| WO | WO 98/21199 * | 5/1998 |
| WO | WO 99/47153 | 9/1999 |
| WO | WO 00/03746 | 1/2000 |
| WO | WO 01/62709 | 8/2001 |
| WO | WO 01/70026 | 9/2001 |
| WO | WO 02/20484 | 3/2002 |
| WO | WO 02/40458 | 5/2002 |
| WO | WO 02/064146 | 8/2002 |
| WO | WO 02/064545 | 8/2002 |
| WO | WO 02/064546 | 8/2002 |
| WO | WO 02/064565 | 8/2002 |
| WO | WO 03/057215 | 7/2003 |
| WO | WO 2004/014369 | 2/2004 |
| WO | WO 2004/014372 | 2/2004 |
| WO | WO 2004/014842 | 2/2004 |
| WO | WO 2004/039365 | 5/2004 |
| WO | WO 2004/043925 | 5/2004 |
| WO | WO 2004/094425 | 11/2004 |

OTHER PUBLICATIONS

U.S. Appl. No. 12/486,118, filed Jun. 17, 2009, Strobel, et al.
U.S. Appl. No. 12/486,144, filed Jun. 17, 2009, Strobel, et al.
Walker, et. al., A Rationally Designed Universal Catalyst for Suzuki-Miyaura Coupling Processes, Angew. Chem. Int. Ed., (2004), vol. 43, pp. 1871-1876.
Bohm, M., et. al., Exploration of Novel Aryl Binding Site of Farnesyltransferase Using Molecular Modeling and Benzophenone-Based Farnesyltransferase Inhibitors, J. Med. Chem., (2001), vol. 44, pp. 3117-3124.
Endres, M., et al., Stroke Protection By 3-Hydroxy-3-Methylgiutaryl (HMG)—CoA Reductase Inhibitors Mediated By Endothelial Nitric Oxide Synthase, Proc. Natl. Acad. Sci. USA, vol. 95, (1998), pp. 8880-8886.

(Continued)

*Primary Examiner* — Zinna Northington Davis
(74) *Attorney, Agent, or Firm* — Scully, Scott, Murphy & Presser, P.C.

(57) ABSTRACT

The present invention relates to heteroarylacrylamides of the formula I,

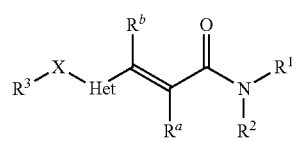

in which Het, X, $R^a$, $R^b$, $R^1$, $R^2$ and $R^3$ have the meanings indicated in the claims, which modulate the transcription of endothelial nitric oxide (NO) synthase and are valuable pharmacologically active compounds. Specifically, the compounds of the formula I upregulate the expression of the enzyme endothelial NO synthase and can be applied in conditions in which an increased expression of said enzyme or an increased NO level or the normalization of a decreased NO level is desired. The invention further relates to processes for the preparation of compounds of the formula I, to pharmaceutical compositions comprising them, and to the use of compounds of the formula I for the manufacture of a medicament for the stimulation of the expression of endothelial NO synthase or for the treatment of various diseases including cardiovascular disorders such as atherosclerosis, thrombosis, coronary artery disease, hypertension and cardiac insufficiency, for example.

11 Claims, No Drawings

OTHER PUBLICATIONS

Keshavarz-K., M., et. al.,, An Improved Isolation of Triformylmetharie (TFM): Properties and Preparation of Some Derivatives, Synthesis, (1988), pp. 641-645.

Kotha, S., et. al., Recent applications of the Suzuki-Miyaura cross-coupling reaction in organic synthesis, Tetrahedron, (2002), vol. 58, pp. 9633-9695.

Li, H., et al., Activation of Protein Kinase Ca and/or E Enhances Transcription of the Human Endothelial Nitric Oxide Synthase Gene, Molecular Pharmacology, vol. 53, pp. 630-637, (1998).

Miyaura, N., et. al., Organoborn Compounds, Topics in Current Chemistry, vol. 219, (2002), pp. 11-59.

Moroi, M., et al., Interaction of Genetic Deficiency of Endothelial Nitric Oxide, Gender, and Pregnancy in Vascular Response to Injury in Mice, J. Clin. Invest., vol. 101, (1998), pp. 1225-1232.

Nakayama, M., et al., T-786-C Mutation in the 5'-Flanking Region of the Endothelial Nitric Oxide Synthase Gene is Associated with Coronary Spasm , Circulation, American Heart Association, Inc., (1999), pp. 2864-2870.

Nishikawa, Y., et. al., Acrylamide Derivatives as Antiallergic Agents. 2. Synthesis and Structure-Activity Relationships of N-[4-[4-(Diphenylmethyl)-1-Piperazinyl]Butyl]-3-(3-Pyridyl)Acrylamides, J. Med, Chem., vol. 32, (1989), pp. 583-593.

Varenne, O., et al., Percutaneous Gene Therapy Using Recombinant Adenoviruses Encoding Human Herpes Simplex Virus Thymidine Kinase, Human PAI-1 , and Human NOS3 in Balloon-injured Porcine Coronary Arteries, Human Gene Therapy (2000), vol. 11, pp. 1329-1339.

Sessa, et. al., Chronic Exercise In Dogs Increases Coronary Vascular Nitric Oxide Production And Endothelial Cell Nitric Oxide Synthase Gene Expression, Circ. Res., (1994), Vol. 74, No. 2, pp. 349-353.

Database Chemcats XP002439343 (2005).

Database Chemcats XP002439342, (2005).

Database Registry XP2439344, (2006).

Schlitzer, et. al., Synthesis of Potential Aldose Reductase inhibitors Based on Minimal Pharmacophore Requirements, J. Pharmacy & Pharmacology, vol. 53, (2001), pp. 831-839.

* cited by examiner

HETEROARYLACRYLAMIDES AND THEIR USE AS PHARMACEUTICALS

CONTINUING DATA

This application is a CON of PCT/EP2007/010709 filed Dec. 8, 2007.

FIELD OF THE INVENTION

The present invention relates to heteroarylacrylamides of the formula I,

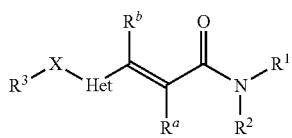

in which Het, X, $R^a$, $R^b$, $R^1$, $R^2$ and $R^3$ have the meanings indicated below, which modulate the transcription of endothelial nitric oxide (NO) synthase and are valuable pharmacologically active compounds. Specifically, the compounds of the formula I upregulate the expression of the enzyme endothelial NO synthase and can be applied in conditions in which an increased expression of said enzyme or an increased NO level or the normalization of a decreased NO level is desired. The invention further relates to processes for the preparation of compounds of the formula I, to pharmaceutical compositions comprising them, and to the use of compounds of the formula I for the manufacture of a medicament for the stimulation of the expression of endothelial NO synthase or for the treatment of various diseases including cardiovascular disorders such as atherosclerosis, thrombosis, coronary artery disease, hypertension and cardiac insufficiency, for example.

BACKGROUND OF THE INVENTION

Endothelial NO synthase (eNOS, NOS-III) belongs to a group of three isoenzymes which produce nitric oxide (nitrogen monoxide, NO) by oxidation of arginine. Endothelially released NO is of central importance in a number of key cardiovascular mechanisms. It has a vasodilating effect and inhibits the aggregation of platelets, the adhesion of leukocytes to the endothelium and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349) were able to obtain a marked increase in eNOS by means of exercise training and the increase in shear stress associated therewith.

Whether regulation at the post-transcriptional level is relevant in vivo, has not been unambiguously proven. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides to the lipid lowering, also in part to an increase in eNOS expression in vivo (Endres et al., Proc. Natl. Acad. Sci. USA 95 (1998) 8880). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension which may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329).

Some low molecular weight compounds which, in cell cultures, may lead to a direct effect on eNOS transcription and expression are disclosed in the literature. For the statins, as has already been mentioned, it has been possible to show such an increase in eNOS in vivo as a side effect. In view of the known range of side effects of this class of substances, however, it is unclear how far use of this effect can be made in a toxicologically unproblematic dose. Liao et al. claim in WO 99/47153 and WO 00/03746 the use of rhoGTPase inhibitors and agents which influence the organization of the actin cytoskeleton for increasing eNOS in endothelial cells and for the therapy of various disorders such as, for example, strokes or pulmonary hypertension without, however, indicating a specific way of achieving this. Certain amide derivatives which upregulate the expression of endothelial NO synthase, in particular N-cycloalkyl amides in which the cycloalkyl ring is fused to a benzene ring or a heteroaromatic ring, have been described in WO 02/064146, WO 02/064545, WO 02/064546, WO 02/064565, WO 2004/014369, WO 2004/014372 and WO 2004/014842. Certain triaza- and tetraazaanthracenedione derivatives which upregulate the expression of endothelial NO synthase have been described in WO 2004/094425. There still exists a need for further compounds which upregulate the expression of endothelial NO synthase and have a favorable property profile and are useful as pharmaceuticals for the treatment of various diseases such as atherosclerosis, coronary artery disease or cardiac insufficiency, for example. Surprisingly it has now been found that the compounds of the formula I are modulators of the transcription of endothelial NO synthase and in particular stimulate, or upregulate, the expression of eNOS, and are useful for the treatment of various diseases such as the mentioned cardiovascular disorders.

Certain heteroarylacrylamides, in which an aryl or heteroaryl group is linked to the heteroaryl substituent on the acrylamide moiety and which are structurally related to formula I, have already been described. For example, in EP 0210782 and in Nishikawa et al., J. Med. Chem. 32 (1989) 583, pyridylacrylamide derivatives are described which comprise a 4-benzhydrylpiperazinylalkyl moiety in the amide group and which exhibit antiallergic activity. In WO 01/62709 and WO 01/70026 phenylenediamine derivatives are described which are antiinfectives and herbicides and which, among others, are N-benzoylphenyl-substituted furylacrylamide and thiazoylacrylamide derivatives carrying a phenyl substituent on the furyl group and thiazolyl group. In Bohm et al., J. Med. Chem. 44 (2001) 3117, it is described that the latter compounds are also inhibitors of farnesyl transferase and potential cancer drugs. In Schlitzer et al., J. Pharmacy Pharmacology 53 (2001) 831, nitrophenylfurylacrylamides and phenylthiazolylacrylamides are described which comprise a carboxy-substituted or methoxycarbonyl-substituted alkyl group in the amide group and which are aldose reductase inhibitors. The compounds described in JP 5-345772, which are inhibitors of acetylcholine esterase useful for the treatment of CNS diseases, include phenylthiazolylacrylamides which comprise a benzylpiperidinyl moiety in the amide group. In EP 0402246 and EP 0489660 N-vinyl-substituted heteroarylacrylamides and other vinyl compounds are described which are fungicides, insecticides and acaricides and which are characterized by an oxy substituent, such as alkoxy, and a methoxycarbonyl substituent on the vinyl group.

An intermediate in the preparation of such compounds is (3-(2-(2-ethylthiazol-4-yl)-thiazol-4-yl)-acryloyl)-methyl-amino-acetic acid methyl ester. 2-(2-Phenylthiazol-4-yl) acrylamide, which is unsubstituted in the amide group, is described in GB 1237194 which relates to compounds having anti-inflammatory activity. In WO 02/040458 (EP 1340749) isoxazole derivatives are described which promote the secretion of insulin and which include isoxazol-4-ylacrylamides in which the isoxazole group carries a cyclic group, such as isoxazol-4-ylacrylamides in which the isoxazole group is substituted by unsubstituted phenyl in the 5-position and optionally by methyl in the 3-position. In WO 03/057215 it is described that such isoxazole derivatives also accelerate the production/secretion of neurotrophic factor. Among the amides described in WO 02/20484, which are characterized by a 4-phenoxypiperidin-1-ylalkyl moiety in the amide group and which are modulators of chemokine and H1 receptor activity useful for the treatment of asthma or rhinitis, are some pyridylacrylamides. In WO 96/16040 and US 2003/0018025, which relate to brain dopamine agonistic and antagonistic imidazolylalkylamine derivatives, certain 1-(2-(4-phenylimidazol-4(5)-yl)acryloyl)-piperazines and -piperidines are described as intermediates which comprise a phenyl or heteroaryl group in the piperazine group and the piperidine group and which can be reduced to the respective imidazolylalkylamine derivatives. In U.S. Pat. No. 5,198,014 and U.S. Pat. No. 5,250,504 herbicidal 3-(4-cyano-1H-pyrazol-5-yl)-acrylic acid derivatives are described which are substituted by an optionally substituted phenyl or pyridin-2-yl group in the 1-position of the pyrazol-5-yl group, which compounds may also be regarded as 3-(4-cyano-2H-pyrazol-3-yl)-acrylic acid derivatives which carry the said phenyl or pyridinyl group in the 2-position of the pyrazol-3-yl group. Some further specific heteroarylacrylamides are known such as the compound (E)-3-[6-(2,6-diethylphenyl)-4-ethyl-2-methylpyridin-3-yl]-1-(piperidin-1-yl)-propenone which is described in WO 2004/043925 which relates to compounds acting as ligands of C5a receptors. A stimulating effect of known heteroarylacrylamides on the transcription or the expression of eNOS and their use in the treatment of diseases which is based on such effect, has not been described.

SUMMARY OF THE INVENTION

A subject of the present invention is a compound of the formula I,

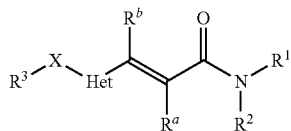

in which

Het is a 5-membered or 6-membered, monocyclic aromatic group which contains one or two identical or different heteroatom ring members chosen from N, $NR^4$, O and S, and which can be substituted on ring carbon atoms by one or more identical or different substituents $R^5$;

X is chosen from a direct bond, $CH_2$, O and NH, provided that X cannot be O or NH if the group $R^3$—X— is bonded to a ring nitrogen atom of the group Het;

$R^a$ and $R^b$ are independently of each other chosen from hydrogen and $(C_1-C_4)$-alkyl;

$R^1$ and $R^2$ are independently of each other chosen from hydrogen, $(C_1-C_6)$-alkyl, $(C_3-C_6)$-alkenyl, $(C_3-C_6)$-alkynyl, $(C_3-C_7)$-cycloalkyl-$C_nH_{2n}$—, phenyl-$C_nH_{2n}$— and heteroaryl-$C_nH_{2n}$—, wherein the groups $(C_1-C_6)$-alkyl, $(C_3-C_7)$-cycloalkyl, $(C_3-C_6)$-alkenyl and $(C_3-C_6)$-alkynyl can all be substituted by one or more identical or different substituents $R^6$, and the groups $C_nH_{2n}$ can all be substituted by one or more identical or different substituents chosen from fluorine and $(C_1-C_4)$-alkyl, and all phenyl and heteroaryl groups can independently of each other be substituted on carbon atoms by one or more identical or different substituents $R^7$, or $R^1$ and $R^2$, together with the nitrogen atom carrying them, form a 4-membered to 7-membered monocyclic, saturated or unsaturated ring which, in addition to the ring nitrogen atom carrying $R^1$ and $R^2$, can contain one or two further heteroatom ring members chosen from N, $NR^9$, O, S, SO and $SO_2$ which can be identical or different, with the proviso that two ring members from the series O, S, SO and $SO_2$ cannot be present in adjacent ring positions, wherein the ring formed by $R^1$ and $R^2$ together with the nitrogen atom carrying them can be substituted on ring carbon atoms by one or more identical or different substituents $R^8$;

$R^3$ is chosen from phenyl and heteroaryl which can all be substituted by one or more identical or different substituents chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_3)$-alkylenedioxy which can be substituted by one or more fluorine atoms, $(C_1-C_4)$-alkylmercapto, $NH_2$, $(C_1-C_4)$-alkylamino, di(($C_1-C_4)$-alkyl)

amino, (($C_1$-$C_4$)-alkyl)-CONH—, di(($C_1$-$C_4$)-alkyl)aminocarbonyl-, (($C_1$-$C_4$)-alkyl)aminocarbonyl-, (($C_1$-$C_4$)-alkyloxy)carbonyl-, $CONH_2$, CN, $CF_3$, $H_2NSO_2$— and ($C_1$-$C_4$)-alkyl-$SO_2$—;

$R^4$ is chosen from hydrogen and ($C_1$-$C_4$)-alkyl;

$R^5$ is chosen from halogen, ($C_1$-$C_4$)-alkyl, ($C_1$-$C_4$)-alkyloxy-($C_1$-$C_2$)-alkyl-, OH, ($C_1$-$C_4$)-alkyloxy which can be substituted by one or more fluorine atoms, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, di(($C_1$-$C_4$)-alkyl)aminocarbonyl-, (($C_1$-$C_4$)-alkyl)aminocarbonyl-, (($C_1$-$C_4$)-alkyloxy)carbonyl-, $CONH_2$, CN, $CF_3$ and ($C_1$-$C_4$)-alkyl-$SO_2$—;

$R^6$ is chosen from fluorine, OH, oxo, ($C_1$-$C_4$)-alkyloxy, ($C_1$-$C_4$)-alkylmercapto, di(($C_1$-$C_4$)-alkyl)amino, (($C_1$-$C_4$)-alkyl)-CONH—, di(($C_1$-$C_4$)-alkyl)aminocarbonyl-, (($C_1$-$C_4$)-alkyl)aminocarbonyl-, (($C_1$-$C_4$)-alkyloxy)carbonyl-, $CONH_2$, CN and $CF_3$;

$R^7$ is chosen from halogen, ($C_1$-$C_4$)-alkyl, ($C_1$-$C_4$)-alkyloxy-($C_1$-$C_2$)-alkyl-, OH, ($C_1$-$C_4$)-alkyloxy which can be substituted by one or more fluorine atoms, ($C_1$-$C_3$)-alkylenedioxy which can be substituted by one or more fluorine atoms, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, di(($C_1$-$C_4$)-alkyl)aminocarbonyl-, (($C_1$-$C_4$)-alkyl)aminocarbonyl-, (($C_1$-$C_4$)-alkyloxy)carbonyl-, $CONH_2$, CN, $CF_3$, $SF_5$, $H_2NSO_2$— and ($C_1$-$C_4$)-alkyl-$SO_2$—;

$R^8$ is chosen from fluorine, ($C_1$-$C_4$)-alkyl, ($C_1$-$C_4$)-alkyloxy-($C_1$-$C_2$)-alkyl-, OH, oxo, ($C_1$-$C_4$)-alkyloxy which can be substituted by one or more fluorine atoms, ($C_1$-$C_3$)-alkylenedioxy, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, di(($C_1$-$C_4$)-alkyl)aminocarbonyl-, (($C_1$-$C_4$)-alkyl)aminocarbonyl-, (($C_1$-$C_4$)-alkyloxy)carbonyl-, $CONH_2$, CN and $CF_3$;

$R^9$ is chosen from hydrogen, ($C_1$-$C_4$)-alkyl, (($C_1$-$C_4$)-alkyl)-CO— and phenyl-CO—, wherein the phenyl group can be substituted by one or more identical or different substituents chosen from halogen, ($C_1$-$C_4$)-alkyl, $CF_3$ and ($C_1$-$C_4$)-alkyloxy;

$R^{10}$ is chosen from hydrogen and ($C_1$-$C_4$)-alkyl;

heteroaryl is a 5-membered or 6-membered, monocyclic aromatic group which contains one, two or three identical or different heteroatom ring members chosen from N, $NR^{10}$, O and S;

n is 0, 1 or 2, where all numbers n are independent of each other and can be identical or different;

in any of its stereoisomeric forms or a mixture of stereoisomeric forms in any ratio, or a physiologically acceptable salt thereof;

provided that $R^1$ and $R^2$, together with the nitrogen atom carrying them, cannot be a piperidin-1-yl group if simultaneously $R^a$ and $R^b$ are hydrogen and the group $R^3$—X—Het- is 6-(2,6-diethylphenyl)-4-ethyl-2-methyl-pyridin-3-yl, 5-(4-chloro-phenyl)-furan-2-yl, 5-(4-bromo-phenyl)-furan-2-yl or 5-(2,5-dichloro-phenyl)-furan-2-yl; and that one of the groups $R^1$ and $R^2$ cannot be benzyl if simultaneously the other of these groups is ethyl, $R^a$ and $R^b$ are hydrogen and the group $R^3$—X—Het- is 5-phenyl-thiophen-2-yl; and that $R^1$ and $R^2$ cannot both be hydrogen if simultaneously the group $R^3$—X—Het- is 2-phenyl-thiazol-4-yl; and that $R^6$ cannot be methoxycarbonyl- if simultaneously the group $R^3$—X—Het- is 2-phenyl-thiazol-4-yl or 2-(2-ethyl-thiazol-4-yl)-thiazol-4-yl; and that the group $R^3$—X—Het- cannot be 5-phenyl-isoxazol-4-yl which is optionally substituted by methyl in the 3-position or 4-cyano-1H-pyrazol-5-yl which is substituted by optionally substituted phenyl or pyridin-2-yl in the 1-position.

Another subject of the present invention is the use of a compound of the formula Ia

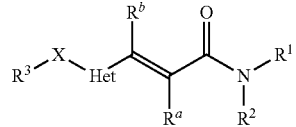

in which

Het is 5-membered to 10-membered, monocyclic or bicyclic, aromatic group which contains one or more identical or different heteroatom ring members chosen from N, $NR^4$, O and S, and which can be substituted on ring carbon atoms by one or more identical or different substituents $R^5$;

X is chosen from a direct bond, $CH_2$, O, $CH_2$—O, O—$CH_2$, S, NH and N(($C_1$-$C_4$)-alkyl), or X is absent and in this case the phenyl, naphthalenyl or heteroaryl group representing the group $R^3$ is fused to the group Het, provided that X cannot be O, $CH_2$—O, S, NH or N(($C_1$-$C_4$)-alkyl) if the group $R^3$—X— is bonded to a ring nitrogen atom of the group Het;

$R^a$ and $R^b$ are independently of each other chosen from hydrogen and ($C_1$-$C_4$)-alkyl;

$R^1$ and $R^2$ are independently of each other chosen from hydrogen, ($C_1$-$C_{10}$)-alkyl, ($C_3$-$C_{10}$)-alkenyl, ($C_3$-$C_{10}$)-alkynyl, ($C_3$-$C_{10}$)-cycloalkyl-$C_nH_{2n}$—, phenyl-$C_nH_{2n}$—, naphthalenyl-$C_nH_{2n}$— and heteroaryl-$C_nH_{2n}$—, wherein the groups ($C_1$-$C_{10}$)-alkyl, ($C_3$-$C_{10}$)-cycloalkyl, ($C_3$-$C_{10}$)-alkenyl and ($C_3$-$C_{10}$)-alkynyl can all be substituted by one or more identical or different substituents $R^6$, and the groups $C_nH_{2n}$ can all be substituted by one or more identical or different substituents chosen from fluorine and ($C_1$-$C_4$)-alkyl, and all phenyl, naphthalenyl and heteroaryl groups can independently of each other be substituted by one or more identical or different substituents $R^7$, or $R^1$ and $R^2$, together with the nitrogen atom carrying them, form a 4-membered to 10-membered, monocyclic or bicyclic, saturated or unsaturated ring which, in addition to the ring nitrogen atom carrying $R^1$ and $R^2$, can contain one or two further heteroatom ring members chosen from N, $NR^9$, O, S, SO and $SO_2$ which can be identical or different, with the proviso that two ring members from the series O, S, SO and $SO_2$ cannot be present in adjacent ring positions, wherein the ring formed by $R^1$ and $R^2$ together with the nitrogen atom carrying them can be substituted by one or more identical or different substituents $R^8$;

$R^3$ is chosen from phenyl, naphthalenyl and heteroaryl which can all be substituted by one or more identical or different substituents chosen from halogen, ($C_1$-$C_6$)-alkyl, ($C_1$-$C_6$)-alkyloxy-($C_1$-$C_3$)-alkyl-, OH, ($C_1$-$C_6$)-alkyloxy which can be substituted by one or more fluorine atoms, ($C_1$-$C_3$)-alkylenedioxy which can be substituted by one or more fluorine atoms, ($C_1$-$C_6$)-alkylmercapto, $NH_2$, ($C_1$-$C_6$)-alkylamino, di(($C_1$-$C_6$)-alkyl)amino, (($C_1$-$C_6$)-alkyl)-CONH—, (($C_1$-$C_6$)-alkyl)-$SO_2NH$—, di(($C_1$-$C_6$)-alkyl)aminocarbonyl-, (($C_1$-$C_6$)-alkyl)aminocarbonyl-, (($C_1$-$C_6$)-alkyloxy)carbonyl-, COOH, $CONH_2$, CN, $CF_3$, (($C_1$-$C_6$)-alkyl)$NHSO_2$—, di(($C_1$-$C_6$)-alkyl)$NSO_2$—, $H_2NSO_2$— and ($C_1$-$C_6$)-alkyl-$SO_2$—;

$R^4$ is chosen from hydrogen and ($C_1$-$C_4$)-alkyl;

$R^5$ is chosen from halogen, ($C_1$-$C_6$)-alkyl, ($C_1$-$C_6$)-alkyloxy-($C_1$-$C_3$)-alkyl-, OH, ($C_1$-$C_6$)-alkyloxy which can be substituted by one or more fluorine atoms, ($C_1$-$C_6$)-alkylmercapto, $NH_2$, ($C_1$-$C_6$)-alkylamino, di(($C_1$-$C_6$)-alkyl)amino, $((C_1-C_6)$-alkyl)-CONH—, $((C_1-C_6)$-alkyl)-SO$_2$NH—, di(($C_1-C_6$)-alkyl)aminocarbonyl-, (($C_1-C_6$)-alkyl)aminocarbonyl-, (($C_1-C_6$)-alkyloxy)carbonyl-, COOH, CONH$_2$, CN, CF$_3$, H$_2$NSO$_2$—, (($C_1-C_6$)-alkyl)NHSO$_2$—, di(($C_1-C_6$)-alkyl)NSO$_2$— and ($C_1-C_6$)-alkyl-SO$_2$—;

$R^6$ is chosen from fluorine, OH, oxo, ($C_1-C_6$)-alkyloxy, ($C_1-C_6$)-alkylmercapto, di(($C_1-C_6$)-alkyl)amino, (($C_1-C_6$)-alkyl)-CONH—, (($C_1-C_6$)-alkyl)-SO$_2$NH—, di(($C_1-C_6$)-alkyl)aminocarbonyl-, (($C_1-C_6$)-alkyl)aminocarbonyl-, (($C_1-C_6$)-alkyloxy)carbonyl-, CONH$_2$, CN and CF$_3$;

$R^7$ is chosen from halogen, ($C_1-C_6$)-alkyl, ($C_1-C_6$)-alkyloxy-($C_1-C_3$)-alkyl-, OH, ($C_1-C_6$)-alkyloxy which can be substituted by one or more fluorine atoms, ($C_1-C_3$)-alkylenedioxy which can be substituted by one or more fluorine atoms, ($C_1-C_6$)-alkylmercapto, NH$_2$, ($C_1-C_6$)-alkylamino, di(($C_1-C_6$)-alkyl)amino, (($C_1-C_6$)-alkyl)-CONH—, (($C_1-C_6$)-alkyl)-SO$_2$NH—, di(($C_1-C_6$)-alkyl)aminocarbonyl-, (($C_1-C_6$)-alkyl)aminocarbonyl-, (($C_1-C_6$)-alkyloxy)carbonyl-, CONH$_2$, CN, CF$_3$, SF$_5$, H$_2$NSO$_2$—, (($C_1-C_6$)-alkyl)NHSO$_2$—, di(($C_1-C_6$)-alkyl)NSO$_2$— and ($C_1-C_6$)-alkyl-SO$_2$—;

$R^8$ is chosen from halogen, ($C_1-C_6$)-alkyl, ($C_1-C_6$)-alkyloxy-($C_1-C_3$)-alkyl-, OH, oxo, ($C_1-C_6$)-alkyloxy which can be substituted by one or more fluorine atoms, ($C_1-C_3$)-alkylenedioxy which can be substituted by one or more fluorine atoms, ($C_1-C_6$)-alkylmercapto, NH$_2$, ($C_1-C_6$)-alkylamino, di(($C_1-C_6$)-alkyl)amino, (($C_1-C_6$)-alkyl)-CONH—, (($C_1-C_6$)-alkyl)-SO$_2$NH—, di(($C_1-C_6$)-alkyl)aminocarbonyl-, (($C_1-C_6$)-alkyl)aminocarbonyl-, (($C_1-C_6$)-alkyloxy)carbonyl-, CONH$_2$, CN, CF$_3$, H$_2$NSO$_2$—, (($C_1-C_6$)-alkyl)NHSO$_2$—, di(($C_1-C_6$)-alkyl)NSO$_2$— and ($C_1-C_6$)-alkyl-SO$_2$—;

$R^9$ is chosen from hydrogen, ($C_1-C_6$)-alkyl, (($C_1-C_6$)-alkyl)-CO— and phenyl-CO—, wherein the phenyl group can be substituted by one or more identical or different substituents chosen from halogen, ($C_1-C_4$)-alkyl, CF$_3$ and ($C_1-C_4$)-alkyloxy;

$R^{10}$ is chosen from hydrogen and ($C_1-C_4$)-alkyl;

heteroaryl is a 5-membered to 10-membered, monocyclic or bicyclic aromatic group which contains one or more identical or different heteroatom ring members chosen from N, NR$^{10}$, O and S;

n is 0, 1, 2 or 3, where all numbers n are independent of each other and can be identical or different;

in any of its stereoisomeric forms or a mixture of stereoisomeric forms in any ratio, or a physiologically acceptable salt thereof, for the manufacture of a medicament for the stimulation of the expression of endothelial NO synthase and for the treatment of a disease in which such a stimulation, or an increase in NO level, is desired, for example a cardiovascular disorder such as atherosclerosis, coronary artery disease or cardiac insufficiency or any other disease mentioned above or below herein.

DETAILED DESCRIPTION OF THE INVENTION

If in the compounds of the formulae I and Ia any groups, substituents, heteroatom ring members, numbers or other features such as, for example, $R^4$, $R^5$, $R^6$, $R^7$, $R^8$, $R^9$, $R^{10}$, alkyl groups, the number n, etc. can occur several times, they can all independently of one another have any of the indicated meanings and can in each case be identical or different from one another. Similarly, in groups such as dialkylamino, for example, the alkyl groups can be identical or different.

Alkyl, alkenyl and alkynyl groups can be linear, i.e. straight-chain, or branched. This also applies when they are part of other groups, for example alkyloxy groups (=alkoxy groups, i.e. alkyl-O— groups), alkyloxycarbonyl groups or alkyl-substituted amino groups, or when they are substituted. Substituted alkyl, alkenyl and alkynyl groups can be substituted by one or more, for example one, two, three, four or five, identical or different substituents which can be located in any desired positions.

Examples of alkyl groups containing one, two, three, four, five, six, seven, eight, nine or ten carbon atoms are methyl, ethyl, propyl, butyl, pentyl, hexyl, heptyl, octyl, nonyl, and decyl and, more specifically, the n-isomer of each of these groups, isopropyl, isobutyl, isopentyl, sec-butyl, tert-butyl, neopentyl or 3,3-dimethylbutyl. Alkenyl groups and alkynyl groups containing three, four, five, six, seven, eight, nine or ten carbon atoms can contain one or more double bonds and/or triple bonds. Preferably they contain one double bond or one triple bond, respectively, which can be present in any desired position of the group. In one embodiment of the invention a carbon atom which is part of a double bond or triple bond is not directly bonded to a nitrogen atom. I.e., in this embodiment a double bond or triple bond is not present in the terminal position of the alkenyl or alkynyl group which is directly bonded to the nitrogen atom. Examples of alkenyl and alkynyl are prop-1-enyl, prop-2-enyl (=allyl), but-2-enyl, 2-methylprop-2-enyl, 3-methylbut-2-enyl, hex-3-enyl, hex-4-enyl, 4-methylhex-4-enyl, dec-3-enyl, dec-9-enyl, prop-2-ynyl (=propargyl), but-2-ynyl, but-3-ynyl, hex-4-ynyl or hex-5-ynyl.

As far as applicable, the preceding explanations regarding alkyl groups apply correspondingly to divalent alkyl groups, i.e. alkanediyl groups and alkylene groups, such as the methylene group —CH$_2$— and the polymethylene groups —CH$_2$—CH$_2$— and —CH$_2$—CH$_2$—CH$_2$— occurring in divalent alkylenedioxy groups such as —O—CH$_2$—O—, —O—CH$_2$—CH$_2$—O— or —O—CH$_2$—CH$_2$—CH$_2$—O—, and the groups C$_n$H$_{2n}$, which can also be linear or branched and/or can be substituted by one or more, for example one, two, three, four or five, identical or different substituents which can be located in any desired positions. In general, the number of substituents can of course not exceed the number of hydrogen atoms in the unsubstituted parent system which can be replaced with a substituent and can be only one or two in the case of a CH$_2$ group, for example. Examples of the group C$_n$H$_{2n}$, in which the number n is 1, 2, or 3, are —CH$_2$—, —CH$_2$—CH$_2$—, —CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—. If the number n in the group C$_n$H$_{2n}$ is 0 (=zero), the two groups which are attached to the group C$_n$H$_{2n}$ are directly connected to one another via a single bond. Similarly, if the group X is a direct bond, the groups R$^3$ and Het are directly connected to one another via a single bond. The two free bonds of a divalent alkylenedioxy group can be connected to the same carbon atom or to different carbon atoms in the residual molecule, for example to two adjacent carbon atoms in an aromatic ring.

Examples of cycloalkyl groups are cyclopropyl, cyclobutyl, cyclopentyl, cyclohexyl, cycloheptyl, cyclooctyl, cyclononyl and cyclodecyl. Substituted cycloalkyl groups can be substituted by one or more, for example one, two, three, four or five, identical or different substituents which can be located in any desired positions. In general, besides any other specified substituents, all cycloalkyl groups in the compounds of the formulae I and Ia, specifically cycloalkyl groups in the groups R$^1$ and R$^2$, can also carry one or more, for example one, two, three, four or five, identical or different (C$_1$-C$_4$)-alkyl substituents, for example methyl substituents, which can be located in any desired positions. Examples of alkyl-substituted cycloalkyl groups are 4-methylcyclohexyl, 4-tert-butylcyclohexyl or 2,3-dimethylcyclopentyl.

If a group like phenyl, naphthalenyl and heteroaryl, including the group Het, which can be unsubstituted or substituted, is substituted by one or more substituents, in general it can carry one, two, three, four or five identical or different substituents, for example. The substituents can be located in any desired positions. Substituted heteroaryl groups can be substituted on ring carbon atoms and/or on suitable ring nitrogen atoms, i.e. on ring nitrogen atoms which in the parent ring system are capable of carrying a hydrogen atom or a substituent, where substituents on such substituted ring nitrogen atoms are in particular alkyl groups such as $(C_1-C_4)$-alkyl groups. Suitable ring nitrogen atoms, such as the ring nitrogen atoms in a pyridine ring or a quinoline ring, can also be present as N-oxides or as quaternary salts, the latter preferably having a counter-anion which is derived from a physiologically acceptable acid. In monosubstituted phenyl groups the substituent can be located in the 2-position, the 3-position or the 4-position. In a disubstituted phenyl group the substituents can be located in 2,3-position, 2,4-position, 2,5-position, 2,6-position, 3,4-position or 3,5-position. In trisubstituted phenyl groups the substituents can be located in 2,3,4-position, 2,3,5-position, 2,3,6-position, 2,4,5-position, 2,4,6-position or 3,4,5-position. Naphthalenyl (=naphthyl) can be naphthalen-1-yl or naphthalen-2-yl. In monosubstituted naphthalen-1-yl groups the substituent can be located in the 2-, 3-, 4-, 5-, 6-, 7- or 8-position, in monosubstituted naphthalen-2-yl groups the substituent can be located in the 1-, 3-, 4-, 5-, 6-, 7- or 8-position. In disubstituted naphthalenyl groups the substituents can likewise occur in any desired positions in the ring via which the naphthalenyl group is bonded to the residual molecule, and/or in the other ring.

Unless stated otherwise in the respective definitions, heteroaromatic groups including heteroaryl groups and the group Het are preferably 5-membered or 6-membered monocyclic aromatic heterocyclic groups or 9-membered or 10-membered bicyclic aromatic heterocyclic groups, where the bicyclic groups contain a 6-membered ring fused to a 5-membered ring or two fused 6-membered rings. In bicyclic heteroaryl groups one or both rings can be aromatic, and one or both rings can contain heteroatom ring members. Preferably heteroaryl groups and other heterocyclic groups contain one, two or three, for example one or two, identical or different heteroatom ring members. The heteroatom ring members in heteroaryl groups and other heterocyclic groups are generally chosen from ring heteroatoms such as nitrogen, oxygen and sulfur, it being possible for suitable ring nitrogen atoms to carry a hydrogen atom or a substituent, such as the groups $R^4$ and $R^{10}$, as is the case in 5-membered aromatic heterocycles such as pyrrole, pyrazole, imidazole or triazole, or in bicyclic aromatic heterocycles such as benzoimidazole, for example. A monocyclic heteroaryl group or group Het which contains a group $R^4$ or $R^{10}$ can contain only one group $R^4$ or $R^{10}$, respectively, and is 5-membered. The heteroatom ring members in heteroaryl groups and other heterocyclic groups can be located in any desired positions provided that the resulting heterocyclic system is known in the art and is stable and suitable as a subgroup in a drug substance. For example, generally it is preferred that two atoms from the series O and S are not present in adjacent ring positions.

Examples of parent heterocycles of heteroaryl groups and other heterocyclic groups including the group Het are pyrrole, furan, thiophene, imidazole, pyrazole, 1,2,3-triazole, 1,2,4-triazole, oxazole (=1,3-oxazole), isoxazole (=1,2-oxazole), thiazole (=1,3-thiazole), isothiazole (=1,2-thiazole), tetrazole, pyridine, pyridazine, pyrimidine, pyrazine, 1,2,3-triazine, 1,2,4-triazine, 1,3,5-triazine, 1,2,4,5-tetrazine, indole, benzothiophene, benzofuran, 1,3-benzodioxole (=1,2-methylenedioxybenzene), 1,3-benzoxazole, 1,3-benzothiazole, benzoimidazole, chroman, isochroman, 1,4-benzodioxane (=1,2-ethylenedioxybenzene), quinoline, isoquinoline, cinnoline, quinazoline, quinoxaline, phthalazine, thienothiophenes, 1,8-naphthyridine and other naphthyridines, acridine or pteridine. Heteroaryl groups, including heteroaryl groups representing $R^3$, and other heterocyclic groups can be bonded via any desired suitable ring carbon atom and, in the case of nitrogen heterocycles, via any suitable ring nitrogen atom. Preferably they are bonded via a ring carbon atom. For example, thiophenyl (=thienyl) can be thiophen-2-yl or thiophen-3-yl, pyridinyl (=pyridyl) can be pyridin-2-yl, pyridin-3-yl or pyridin-4-yl, imidazolyl can be, for example, 1H-imidazol-1-yl, 1H-imidazol-2-yl, 1H-imidazol-4-yl or 1H-imidazol-5-yl, quinolinyl (=quinolyl) can be quinolin-2-yl, quinolin-3-yl, quinolin-4-yl, quinolin-5-yl, quinolin-6-yl, quinolin-7-yl or quinolin-8-yl. In monosubstituted pyridin-2-yl the substituent can be located in the 3-position, 4-position, 5-position or 6-position, in monosubstituted pyridin-3-yl the substituent can be located in the 2-position, 4-position, 5-position or 6-position, in monosubstituted pyridin-4-yl the substituent can be located in the 2-position or 3-position.

As far as applicable, the preceding explanations regarding heteroaryl groups apply correspondingly to groups which can be regarded as divalent heteroaryl groups, i.e. heteroarylene groups, such as the group Het in formulae I and Ia. In general, a divalent heteroaryl group can be bonded to the adjacent groups via any two desired suitable ring atoms including ring carbon atoms and/or, in the case of nitrogen heterocycles, ring nitrogen atoms. Preferably they are bonded via any two ring carbon atoms, in particular in the case of the group Het. In the case of a divalent bicyclic heteroaryl group, the positions via which it is bonded to the adjacent groups can be located in the same ring or in different rings. In the case of a divalent group derived from furan or thiophene, for example, the adjacent groups can be bonded in 2,3-position, 2,4-position, 2,5-position or 3,4-position. A divalent group derived from thiazole can be thiazole-2,4-diyl, thiazole-2,5-diyl or thiazole-4,5-diyl. A divalent group derived from pyridine can be pyridine-2,3-diyl, pyridine-2,4-diyl, pyridine-2,5-diyl, pyridine-2,6-diyl, pyridine-3,4-diyl or pyridine-3,5-diyl. In the case of an unsymmetrical divalent group the present invention includes all positional isomers, i.e., in the case of a pyridine-2,5-diyl group, for example, it includes the compound in which the one adjacent group is present in the 2-position and the other adjacent group is present in the 5-position as well as the compound in which the one adjacent group is present in the 5-position and the other adjacent group is present in the 2-position. Depending on the ranking order of the adjacent groups in the nomenclature of the compound, in the name of a compound the numbers of the locations of the adjacent groups may differ from the ones indicated above and, for example, a pyridine-2,5-diyl group may be designated as a pyridine-3,6-diyl group.

As far as applicable, the above explanations also apply correspondingly to the aromatic heterocycle which is formed by fusion of the group $R^3$ to the group Het in case the group X is absent. In the respective compounds of the formula Ia the resulting polycyclic heteroaromatic group, which represents the $R^3$—X—Het- moiety, is a bicyclic or tricyclic or tetracyclic ring system, preferably a bicyclic or tricyclic ring system, for example a bicyclic ring system, and contains one or more, for example one, two, three or four, identical or different heteroatom ring members chosen from those which can be present in the groups Het and $R^3$. A phenyl or naphthalenyl or heteroaryl group representing $R^3$ can be fused to, or condensed to, the group Het via any suitable bond in $R^3$ and any suitable bond in the group Het, provided that the resulting polycyclic heteroaromatic group is known in the art and is stable and suitable as a subgroup in a drug substance and that in the resulting group at least the ring bonded to the group $CR^b$ can be an aromatic ring, i.e. contain six conjugated pi electrons in case of a 5-membered or 6-membered monocyclic ring. For example, if the group Het in a compound of the formula Ia is a pyridine ring, X is absent and $R^3$ is phenyl, the latter carbocyclic ring can be fused to the bond between positions 2 and 3 or the bond between positions 3 and 4 in the pyridine ring, and the resulting polycyclic heteroaromatic group representing the $R^3$—X—Het- moiety is a quinolinyl or isoquinolinyl group. If a naphthalenyl group representing $R^3$ is fused to a pyridine ring representing Het, the resulting polycyclic heteroaromatic group representing the $R^3$—X—Het- moiety is an aza-anthracenyl or aza-phenanthrenyl group. The polycyclic heteroaromatic which is present in case X is absent, can be bonded to the group $CR^b$ via any suitable ring atom, preferably a ring carbon atom, in an aromatic ring originating from the group Het, and can be substituted by substituents as outlined above for the groups $R^3$ and Het.

The heterocyclic ring which can be formed by $R^1$ and $R^2$ together with the nitrogen atom which carries them, can be 4-membered, 5-membered, 6-membered, 7-membered, 8-membered, 9-membered or 10-membered, and can be saturated, i.e. contain no double bond within the ring, or unsaturated, including partially unsaturated and aromatic, in particular partially unsaturated, and contain, for example, one, two, three or four double bonds within the ring, provided the respective ring system is known in the art and is stable and suitable as a subgroup in a drug substance. Examples of residues of heterocyclic rings formed by $R^1$ and $R^2$ together with the nitrogen atom which carries them, are azetidin-1-yl, pyrrolidin-1-yl, 2,5-dihydro-1H-pyrrol-1-yl, piperidin-1-yl, 1,2,3,4-tetrahydropyridin-1-yl, 1,2,5,6-tetrahydropyridin-1-yl, azepan-1-yl, azocan-1-yl, azecan-1-yl, octahydrocyclopenta[b]pyrrol-1-yl, 2,3-dihydro-1H-indol-1-yl, octahydro-1H-indol-1-yl, 2,3-dihydro-1H-isoindol-2-yl, octahydro-1H-isoindol-2-yl, 1,2,3,4-tetrahydroquinolin-1-yl, decahydroquinolin-1-yl, 1,2,3,4-tetrahydroisoquinolin-2-yl, decahydroisoquinolin-2-yl, 4,5,6,7-tetrahydrothieno[3,2-c]pyridin-5-yl, pyrazolidin-1-yl, imidazolidin-1-yl, hexahydropyrimidin-1-yl, piperazin-1-yl, [1,3]diazepan-1-yl, [1,4]diazepan-1-yl, oxazolidin-3-yl, [1,3]oxazinan-3-yl, morpholin-4-yl, [1,3]oxazepan-3-yl, [1,4]oxazepan-4-yl, thiazolidin-3-yl, [1,3]thiazinan-3-yl, thiomorpholin-4-yl, [1,3]thiazepan-3-yl, [1,4]thiazepan-4-yl. As applies to the ring which can be formed by $R^1$ and $R^2$ together with the nitrogen atom carrying them in general, all listed examples of heterocyclic groups can be unsubstituted or substituted as indicated above, for example by $R^8$. For example, they can be substituted on one or more, for example one, two or three, preferably one or two, more preferably one, ring carbon atoms by one or more, for example one, two, three or four, preferably one or two, identical or different substituents such as $(C_1-C_4)$-alkyl, for example methyl, and $(C_1-C_4)$-alkyloxycarbonyl, for example methoxycarbonyl, and/or on one or more ring nitrogen atoms by substituents such as $(C_1-C_4)$-alkyl, for example methyl, and $(C_1-C_4)$-alkyl-CO—, for example acetyl, which latter groups represent $R^9$. Besides that, as applies to the ring which can be formed by $R^1$ and $R^2$ together with the nitrogen carrying them in general, ring sulfur atoms in the listed heterocyclic groups can carry one or two oxo groups, i.e. doubly bonded oxygen atoms, and thus become SO or $SO_2$ groups, i.e. sulfoxide or sulfone groups or S-oxides or S,S-dioxides. For example, the sulfur atom in a thiomorpholin-4-yl group can carry one or two oxo groups, and besides the thiomorpholin-4-yl group also the groups 1-oxo-thiomorpholin-4-yl and 1,1-dioxo-thiomorpholin-4-yl can be present in a compound of the invention.

Halogen is fluorine, chlorine, bromine or iodine, preferably fluorine, chlorine or bromine, more preferably fluorine or chlorine.

An oxo group, when bonded to a carbon atom, replaces two hydrogen atoms on a carbon atom of the parent system. Thus, if a $CH_2$ group is substituted by oxo, i.e. by a doubly bonded oxygen atom, it becomes a CO group. Evidently, an oxo group cannot occur as a substituent on a carbon atom in an aromatic ring.

The present invention includes all stereoisomeric forms of the compounds of the formulae I and Ia and their salts. With respect to each chiral center, independently of any other chiral center, the compounds of formulae I and Ia can be present in S configuration or substantially in S configuration, or in R configuration or substantially in R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings, the invention includes both the E form and Z form, or the cis form and the trans form, as well as mixtures of these forms in all ratios. In one embodiment of the invention a double bond, including the double bond depicted in formulae I and Ia between the carbon atoms to which the groups $R^a$ and $R^b$ are bonded, is present in the E form or trans form or substantially in the E form or trans form. In another embodiment of the invention a double bond, including the double bond depicted in formulae I and Ia between the carbon atoms to which the groups $R^a$ and $R^b$ are bonded, is present in the Z form or cis form or substantially in the Z form or cis form. If desired, the preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally a derivatization can be carried out before a separation of stereoisomers. The separation of a mixture of stereoisomers can be carried out at the stage of the compound of the formula I or Ia or at the stage of a starting material or an intermediate during the synthesis. The present invention also includes all tautomeric forms of the compounds of formulae I and Ia and their salts.

In case the compounds of the formulae I and Ia contain one or more acidic and/or basic groups, i.e. salt-forming groups, the invention also comprises their corresponding physiologically or toxicologically acceptable salts, i.e. non-toxic salts, in particular their pharmaceutically acceptable salts. Thus, the compounds of the formulae I and Ia which contain an acidic group can be present on such groups, and can be used according to the invention, for example, as alkali metal salts, alkaline earth metal salts or as ammonium salts. More specific examples of such salts include sodium salts, potassium salts, calcium salts, magnesium salts, quaternary ammonium salts such as tetraalkylammonium salts, or acid addition salts with ammonia or organic amines such as, for example, ethylamine, ethanolamine, triethanolamine or amino acids. Compounds of the formulae I and Ia which contain a basic group, i.e. a group which can be protonated, can be present on such groups, and can be used according to the invention, for example, in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, nicotinic acid, isonicotinic acid, citric acid, adipic acid, and other acids known to the person skilled in the art. If the compounds of the formulae I and Ia simultaneously contain acidic and basic groups in the molecule, the invention also includes, in addition to the salt forms mentioned, inner salts or betaines or zwitterions. The salts of the compounds of the formulae I and Ia can be obtained by customary methods which are known to the person skilled in the art like, for example, by contacting the compound of the formula I or Ia with an organic or inorganic acid or base in a solvent or diluent, or by anion exchange or cation exchange from another salt. The present invention also includes all salts of the compounds of the formula I which, owing to low physiological compatibility, are not directly suitable for use in pharmaceuticals but which can be used, for example, as intermediates for chemical reactions or for the preparation of physiologically acceptable salts.

The present invention furthermore includes all solvates of compounds of the formulae I and Ia, for example hydrates or adducts with alcohols, active metabolites of the compounds of the formulae I and Ia, and also prodrugs and derivatives of the compounds of the formulae I and Ia which in vitro may not necessarily exhibit pharmacological activity but which in vivo are converted into pharmacologically active compounds, for example esters or amides of carboxylic acid groups.

In the compounds of the formula Ia the divalent group Het is preferably defined as in the compounds of the formula I. More generally, one embodiment of the present invention relates to the use of a compound of the formula I, which is defined as above or below, in any of its stereoisomeric forms or a mixture of stereoisomeric forms in any ratio, or a physiologically acceptable salt thereof, for the manufacture of a medicament for the stimulation of the expression of endothelial NO synthase and for the treatment of a disease in which such a stimulation, or an increase in NO level, is desired, for example a cardiovascular disorder such as atherosclerosis, coronary artery disease or cardiac insufficiency or any other diseases mentioned above or below herein.

More preferably, the divalent group Het in the compounds of the formulae I and Ia is a divalent aromatic group of the formula II

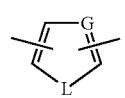

II in which G is chosen from N and CH and L is chosen from S, O, $NR^4$, CH=CH, CH=N and N=CH, and which can be substituted by one or more identical or different substituents $R^5$, i.e. in which one or more ring carbon atoms can carry a substituent $R^5$ instead of the hydrogen atoms which are implicitly present on the carbon atoms depicted in formula II or which are specified in the definition of the groups G and L, with the proviso that the ring system depicted in formula II comprises at least one heteroatom ring member, i.e. a group $NR^4$ or an N, S or O atom, as a ring member. $R^5$ and $R^4$ in the ring system of the formula II are defined as indicated above with respect to the compounds of the formulae I and Ia. Particularly preferably the group Het in the compounds of the formulae I and Ia and the group of the formula II is chosen from the heteroarylene groups pyridinediyl, pyrimidinediyl, thiazolediyl, oxazolediyl, imidazolediyl, furandiyl and thiophenediyl, i.e. the divalent residues of pyridine, pyrimidine, thiazole, oxazole, imidazole, furan and thiophene, more particularly preferably from pyridinediyl, pyrimidinediyl, thiazolediyl, oxazolediyl, imidazolediyl and thiophenediyl, which can all be substituted by one or more identical or different substituents $R^5$ and wherein one of the ring nitrogen atoms of the imidazolediyl group, which represents the nitrogen atom in the group $NR^4$ in the definition of the group L, carries a group chosen from hydrogen and $(C_1-C_4)$-alkyl. In one embodiment of the invention, Het is thus chosen from pyridinediyl, pyrimidinediyl, thiazolediyl, oxazolediyl, imidazolediyl and thiophenediyl. In another embodiment Het is chosen from pyridinediyl, thiazolediyl, oxazolediyl, imidazolediyl and thiophenediyl, in a further embodiment from pyridinediyl, pyrimidinediyl, thiazolediyl, imidazolediyl and thiophenediyl, which can all carry groups $R^4$ and $R^5$ as indicated. Especially preferably the group Het in the compounds of the formulae I and Ia and the group of the formula II is chosen from pyridinediyl, thiazolediyl, imidazolediyl and thiophenediyl, more especially preferably from pyridinediyl and thiazolediyl, which can all be substituted by one or more identical or different substituents $R^5$ and wherein one of the ring nitrogen atoms of the imidazolediyl group, which represents the nitrogen atom in the group $NR^4$ in the definition of the group L, carries a group chosen from hydrogen and $(C_1-C_4)$-alkyl. In one embodiment of the invention the group Het in the compounds of the formulae I and Ia and the group of the formula II is a pyridinediyl group which can be substituted by one or more identical or different substituents $R^5$. In another embodiment of the invention the group Het in the compounds of the formulae I and Ia and the group of the formula II is a pyrimidinediyl group which can be substituted by one or more identical or different substituents $R^5$. In one embodiment of the present invention the groups representing the group Het in the compounds of the formulae I and Ia or in the group of the formula II, in which latter group the bonds via which it is connected to the groups $R^3$—X and $CR^b$ are represented by the lines intersecting the ring sides, are bonded to the adjacent groups $R^3$—X and $CR^b$ via any two ring carbon atoms or via any one ring carbon atom and a suitable ring nitrogen atom, where in the latter case preferably the nitrogen atom is bonded to the group $R^3$—X and the carbon atom is bonded to the group $CR^b$. In another embodiment of the invention the groups representing the group Het or the group of the formula II are bonded to the adjacent groups $R^3$—X and $CR^b$ via any two ring carbon atoms. Preferably a pyridinediyl group representing Het or the group of the formula II is bonded to the adjacent groups via positions 3 and 6 of the pyridine ring, which positions may also be numbered as positions 5 and 2, respectively, depending on the ranking order of the groups bonded to the pyridine ring, or via positions 3 and 5, or via positions 2 and 6, particularly preferably via positions 3 and 6, where each of the groups $R^3$—X and $CR^b$ can be present in each of the positions. I.e., in the latter pyridinediyl group, for example, which is bonded via positions 3 and 6, the group $R^3$—X can be present in position 3 and the group $CR^b$ in position 6, as well as the group $R^3$—X can be present in position 6 and the group $CR^b$ in position 3, where preferably the group $R^3$—X is present in position 6 and the group $CR^b$ in position 3. A pyrimidinediyl group representing the group Het or the group of the formula II is preferably bonded to the adjacent groups via positions 2 and 5, where each of the groups $R^3$—X and $CR^b$ can be present in each of the positions and preferably the group $R^3$—X is present in position 2 and the group $CR^b$ is present in position 5. Preferably a group of the formula IIa,

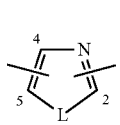

IIa which represents Het or the group of the formula II and in which L is O, S or $NR^4$, i.e. which is an oxazolediyl, thiazolediyl or imidazolediyl group, is bonded to the adjacent groups via positions 2 and 5 or via positions 2 and 4, particularly preferably via positions 2 and 4, where each of the groups $R^3$—X and $CR^b$ can be present in each of the positions and preferably the group $R^3$—X is present in position 4 and the group $CR^b$ in position 2. Preferably a thiophenediyl or a furandiyl group which represents Het or the group of the formula II is bonded to the adjacent groups via positions 2 and 5 or via positions 2 and 4, which latter positions may also be numbered as positions 5 and 3, particularly preferably via positions 2 and 4, where each of the groups $R^3$—X and $CR^b$ can be present in each of the positions and preferably the group $R^3$—X is present in position 4 and the group $CR^b$ in position 2.

Preferred groups Het or groups of the formula II thus include the divalent heteroaromatic groups depicted in the following formulae IIIa to IIIg which represent preferred embodiments of the structural moiety $R^3$—X—Het- in the compounds of the formulae I and Ia, and in which the heteroaromatic group can be unsubstituted or substituted by one or more identical or different substituents $R^5$. In formulae IIIa to IIIg the line starting at a ring carbon atom represents the free bond by which the group is bonded to the group $CR^b$.

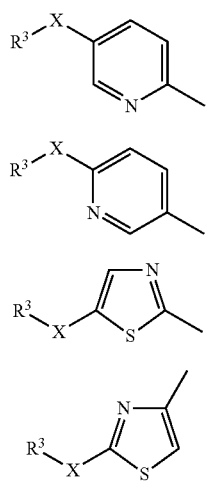

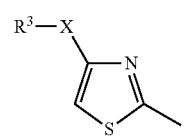

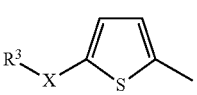

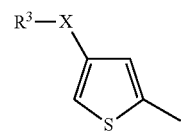

Particularly preferred groups Het or groups of the formula II include the divalent heteroaromatic groups depicted in the formulae IIIb, IIIe and IIIg, especially the group depicted in formula IIIb, which represent particularly and especially preferred embodiments of the structural moiety $R^3$—X—Het- in the compounds of the formulae I and Ia.

In the group $CH_2$—O representing the group X, the $CH_2$ group is bonded to the group $R^3$ and the oxygen atom is bonded to the group Het. In the group O—$CH_2$, the group $CH_2$ is bonded to the group Het and the oxygen atom is bonded to the group $R^3$. In one embodiment of the invention, the group X in the compounds of the formula Ia is defined as in the compounds of the formula I. Preferably, the group X in the compounds of the formulae I and Ia is chosen from a direct bond, $CH_2$ and O, in particular from a direct bond and O, or in the compounds of the formula Ia the group X is absent and in this case the phenyl, naphthalenyl or heteroaryl group representing the group $R^3$ is fused to the group Het, provided that X cannot be O if the group $R^3$—X— is bonded to a ring nitrogen atom of the group Het. In one embodiment of the present invention the group X in the compounds of the formulae I and Ia is chosen from a direct bond and O. In another embodiment of the present invention the group X in the compounds of the formulae I and Ia is a direct bond.

In a further embodiment of the present invention the group X in the compounds of the formula Ia is absent and in this embodiment the phenyl, naphthalenyl or heteroaryl group representing the group $R^3$ is fused to the group Het. In still a further embodiment of the present invention the group X in the compounds of the formula Ia cannot be absent, i.e. in this embodiment the group X in the compounds of the formula Ia it is chosen from a direct bond, $CH_2$, O, $CH_2$—O, O—$CH_2$, S, NH and N(($C_1$-$C_4$)-alkyl) and preferably is defined as with respect to the compounds of the formula I.

In case the group X is absent, the phenyl, naphthalenyl or heteroaryl group representing the group $R^3$ is fused to the group Het or the ring system depicted in formula II which contains the groups G and L. In case X is absent, in a particularly preferred embodiment of the present invention the structural moiety $R^3$—X—Het- in the compounds of the formula Ia is a bicyclic heteroaryl group which comprises a monocyclic 5-membered or 6-membered heteroaromatic ring which represents the group Het and to which the group $CR^b$ is bonded, and a benzene ring which is fused to said heteroaromatic ring system and which represents the group $R^3$, where the heteroaromatic ring can be substituted by one or more identical or different substituents $R^5$ and the benzene ring can be substituted as indicated above with respect to $R^3$. In case X is absent, the said structural moiety $R^3$—X—Het- is more particularly preferably chosen from quinolinyl, isoquinolinyl, benzoimidazolyl, benzothiazolyl and benzothienyl, especially preferably from quinolinyl, benzoimidazolyl and benzothiazolyl, which are all bonded to the group $CR^b$ via the heterocyclic ring and which can be substituted as indicated.

Preferably, the groups $R^a$ and $R^b$ in the compounds of the formulae I and Ia are independently of each other chosen from hydrogen and methyl. More preferably, one of $R^a$ and $R^b$ is hydrogen and the other is defined as indicated. Particularly preferably, $R^a$ and $R^b$ are both hydrogen.

If the ring which can be formed by the groups $R^1$ and $R^2$ together with the nitrogen atom carrying them is a monocyclic ring system, in one embodiment of the invention it is saturated or partially unsaturated. More specifically, in one embodiment the ring is saturated or contains one or two double bonds within the ring, and in another embodiment it is saturated or contains one double bond within the ring, and in a further embodiment it is saturated. If the said ring is a bicyclic ring system, in one embodiment the specific ring of the bicyclic ring system to which the CO group depicted in formula Ia is bonded, is saturated or is partially unsaturated, and in a more specific embodiment this ring contains one or two double bonds within the ring of which one double bond can be common to both rings, and the second ring of the bicyclic ring system is a saturated or an aromatic ring, in particular an aromatic ring such as a benzene ring. In the compounds of the formula Ia a monocyclic ring formed by the groups $R^1$ and $R^2$ together with the nitrogen atom carrying them preferably contains 4, 5, 6 or 7 ring members, and a bicyclic ring system preferably contains 9 or 10 ring members. The ring which can be formed by the groups $R^1$ and $R^2$ together with the nitrogen atom carrying them is preferably a monocyclic ring system.

In one embodiment of the present invention, the ring which can be formed by the groups $R^1$ and $R^2$ together with the nitrogen atom carrying them can contain, in addition to the said nitrogen atom carrying $R^1$ and $R^2$, one further heteroatom ring member, i.e. one further ring heteroatom or heteroatom group, which is chosen from N, $NR^9$, O, S, SO and $SO_2$ and preferably is chosen from $NR^9$, O, S, SO and $SO_2$ and more preferably is chosen from $NR^9$, O and S. If the heterocycle formed by $R^1$ and $R^2$ together with the nitrogen atom carrying them is substituted by one or more identical or different substituents $R^8$, it preferably is substituted by one, two, three, four or five, more preferably by one, two, three or four, particularly preferably by one, two or three, more particularly preferably by one or two identical or different substituents $R^8$ on ring carbon atoms, in addition to oxo groups on ring sulfur atoms and/or groups $R^9$ on ring nitrogen atoms which may be present.

If $R^1$ and $R^2$, together with the nitrogen atom carrying them, form a ring, in one embodiment of the invention they form a saturated monocyclic 4-membered, 5-membered, 6-membered or 7-membered ring which, in addition to the nitrogen atom carrying $R^1$ and $R^2$, can contain one further heteroatom ring member group chosen from $NR^9$, O, S, SO and $SO_2$, preferably from $NR^9$, O and S, wherein the ring can be substituted by one or more identical or different substituents $R^8$. Examples of residues of such rings, from which the group $-NR^1R^2$ in the formulae I and Ia, which results if $R^1$ and $R^2$ together with the nitrogen atom carrying them form a ring, is preferably chosen, are azetidin-1-yl, pyrrolidin-1-yl, piperidin-1-yl, azepan-1-yl, imidazolidin-1-yl, hexahydropyrimidin-1-yl, piperazin-1-yl, [1,3]diazepan-1-yl, [1,4]diazepan-1-yl, oxazolidin-3-yl, [1,3]oxazinan-3-yl, morpholin-4-yl, [1,3]oxazepan-3-yl, [1,4]oxazepan-4-yl, thiazolidin-3-yl, [1,3]thiazinan-3-yl, thiomorpholin-4-yl, [1,3]thiazepan-3-yl and [1,4]thiazepan-4-yl. Preferred such residues include azetidin-1-yl, pyrrolidin-1-yl, piperidin-1-yl, azepan-1-yl, morpholin-4-yl, [1,4]oxazepan-4-yl, thiazolidin-3-yl and thiomorpholin-4-yl.

All rings formed by $R^1$ and $R^2$ together with the nitrogen atom carrying them can be substituted on carbon atoms by one or more identical or different substituents $R^8$, and/or can carry on a ring nitrogen atom which is not bonded to the CO group, which is depicted in formulae I and Ia, a group $R^9$ and/or can carry on a ring sulfur atom one or two oxo groups, to give a substituted group as indicated above. As examples of such substituted groups which are substituted by methyl, acetyl or methoxycarbonyl groups representing $R^8$ and/or $R^9$, and/or by an oxo group on a carbon atom representing $R^8$, and/or by one or two oxo groups on a sulfur atom, and which can represent the group $-NR^1R^2$ in formulae I and Ia, the groups 2,6-dimethyl-piperidin-1-yl, 2,6-dimethyl-morpholin-4-yl, 4-methyl-piperazin-1-yl, 4-acetyl-piperazin-1-yl, 3-oxo-piperazin-1-yl, 4-methyl-3-oxo-piperazin-1-yl, 1-oxo-thiomorpholin-4-yl and 1,1-dioxo-thiomorpholin-4-yl may be mentioned.

If $R^1$ and $R^2$ do not form a ring together with the nitrogen atom carrying them, they preferably are independently of each other chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, more preferably from $(C_1-C_4)$-alkyl, $(C_3-C_7)$-cycloalkyl, phenyl, phenyl-$CH_2$—, heteroaryl and heteroaryl-$CH_2$—, particularly preferably from $(C_1-C_4)$-alkyl, $(C_3-C_7)$-cycloalkyl, phenyl and heteroaryl, and in each case $R^2$ can in addition be hydrogen, wherein the groups $(C_1-C_4)$-alkyl and $(C_3-C_7)$-cycloalkyl can both be substituted by one or more identical or different substituents $R^6$, and the groups phenyl and heteroaryl can both be substituted by one or more identical or different substituents $R^7$. A heteroaryl group present in $R^1$ or $R^2$ or representing $R^1$ or $R^2$ is preferably chosen from pyridinyl, thiophenyl and thiazolyl. In one embodiment of the invention, in compounds in which $R^1$ and $R^2$ together with the nitrogen atom carrying them do not form a ring, $R^2$ is chosen from hydrogen and $(C_1-C_4)$-alkyl which can be substituted by one or more identical or different substituents $R^6$, and $R^1$ is defined as indicated. In another embodiment of the invention, in compounds in which $R^1$ and $R^2$ together with the nitrogen atom carrying them do not form a ring, $R^2$ is hydrogen and $R^1$ is defined as indicated. In a further embodiment of the invention, in compounds in which $R^1$ and $R^2$ together with the nitrogen atom carrying them do not form a ring, $R^1$ and $R^2$ are defined as indicated, but none of them can be hydrogen. If $R^1$ and/or $R^2$ is an alkenyl group or an alkynyl group, preferably the nitrogen atom carrying $R^1$ and $R^2$ is not in conjugation with a double bond or triple bond, i.e., preferably the nitrogen atom carrying $R^1$ and $R^2$ is not directly bonded to a carbon atom in an alkenyl group or alkynyl group which is part of a double bond or triple bond.

In the compounds of the formula Ia the groups $R^1$ and $R^2$ are preferably defined as in the compounds of the formula I. More preferably, the groups $R^1$ and $R^2$ in the compounds of the formulae I and Ia are independently of each other chosen from $(C_1-C_6)$-alkyl, $(C_3-C_6)$-alkenyl, $(C_3-C_6)$-alkynyl, $(C_3-C_7)$-cycloalkyl-$C_nH_{2n}$—, phenyl-$C_nH_{2n}$— and heteroaryl-$C_nH_{2n}$—, and $R^2$ can in addition be hydrogen, wherein the groups $(C_1-C_6)$-alkyl, $(C_3-C_7)$-cycloalkyl, $(C_3-C_6)$-alkenyl and $(C_3-C_6)$-alkynyl can all be substituted by one or more identical or different substituents $R^6$, and the groups $C_nH_{2n}$ can all be substituted by one or more identical or different substituents chosen from fluorine and $(C_1-C_4)$-alkyl, and all phenyl groups and heteroaryl groups can be substituted by one or more identical or different substituents $R^7$, or $R^1$ and $R^2$, together with the nitrogen atom which carries them, form a 4-membered to 7-membered monocyclic, saturated or unsaturated ring which, in addition to the ring nitrogen atom carrying $R^1$ and $R^2$, can contain one or two further heteroatom ring members chosen from N, $NR^9$, O, S, SO and $SO_2$ which can be identical or different, with the proviso that two ring members from the series O, S, SO and $SO_2$ cannot be present in adjacent ring positions, wherein the ring formed by $R^1$ and $R^2$ and the nitrogen atom carrying them can be substituted by one or more identical or different substituents $R^8$.

Particularly preferably, the group $R^1$ in the compounds of the formulae I and Ia is chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, and the group $R^2$ is chosen from hydrogen, $(C_1-C_4)$-alkyl, $(C_3-C_7)$-cycloalkyl-$C_nH_{2n}$—, phenyl-$C_nH_{2n}$— and heteroaryl-$C_nH_{2n}$—, wherein all $(C_1-C_4)$-alkyl and $(C_3-C_7)$-cycloalkyl groups can be substituted by one or more identical or different substituents $R^6$, and all phenyl and heteroaryl groups can be substituted by one or more identical or different substituents $R^7$, and wherein preferably the numbers n are independently of each other chosen from 0 and 1, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ and the nitrogen atom carrying them can be substituted by one or more identical or different substituents $R^8$.

More particularly preferably, the group $R^1$ in the compounds of the formulae I and Ia is chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, and the group $R^2$ is chosen from hydrogen and $(C_1-C_4)$-alkyl, wherein all $(C_1-C_4)$-alkyl and $(C_3-C_7)$-cycloalkyl groups can be substituted by one or more identical or different substituents $R^6$, and all phenyl and heteroaryl groups can be substituted by one or more identical or different substituents $R^7$, and wherein preferably the numbers n are independently of each other chosen from 0 and 1, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ and the nitrogen atom carrying them can be substituted by one or more identical or different substituents $R^8$.

Especially preferably, the group $R^1$ in the compounds of the formulae I and Ia is chosen from $(C_1-C_4)$-alkyl, $(C_3-C_7)$-cycloalkyl, phenyl and heteroaryl, and the group $R^2$ is chosen from hydrogen and $(C_1-C_4)$-alkyl, wherein all $(C_1-C_4)$-alkyl and $(C_3-C_7)$-cycloalkyl groups can be substituted by one or more identical or different substituents $R^6$, and all phenyl and heteroaryl groups can be substituted by one or more identical or different substituents $R^7$, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ and the nitrogen atom carrying them can be substituted by one or more identical or different substituents $R^8$.

In one embodiment of the invention, the groups $R^1$ and $R^2$, together with the nitrogen atom carrying them, form a 4-membered to 7-membered monocyclic, saturated or unsaturated ring which, in addition to the ring nitrogen atom carrying $R^1$ and $R^2$, can contain one or two further heteroatom ring member chosen from N, $NR^9$, O, S, SO and $SO_2$, which can be identical or different, with the proviso that two ring members from the series O, S, SO and $SO_2$ cannot be present in adjacent ring positions, wherein the ring formed by $R^1$ and $R^2$ and the nitrogen atom carrying them can be substituted by one or more identical or different substituents $R^8$, and preferably $R^1$ and $R^2$, together with the nitrogen atom carrying them, form a 4-membered to 7-membered monocyclic saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ and the nitrogen atom carrying them can be substituted by one or more identical or different substituents $R^8$, and more preferred features of this embodiment are those outlined above.

In the compounds of the formula Ia the group $R^3$ is preferably chosen from phenyl, naphthalenyl and heteroaryl, more preferably from phenyl and heteroaryl, which can all be substituted by one or more identical or different substituents chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_3)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $((C_1-C_4)$-alkyl)-$SO_2NH$—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN, $CF_3$, $H_2NSO_2$— and $(C_1-C_4)$-alkyl-$SO_2$—. Particularly preferably, the group $R^3$ in the compounds of the formula Ia is defined as in formula I. More particularly preferably, the group $R^3$ in the compounds of the formulae I and Ia is chosen from phenyl and heteroaryl which can all be substituted by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—, and especially preferably by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $CF_3$ and $(C_1-C_4)$-alkyl-$SO_2$—, and more especially preferably by one or more identical or different substituents chosen from halogen, $(C_1-C_4)$-alkyl, $(C_1-C_4)$-alkyloxy which can be substituted by one or more fluorine atoms and $CF_3$. A heteroaryl group representing $R^3$ is preferably chosen from pyridinyl, pyrazolyl, thiophenyl, isoxazolyl and benzothiophenyl, more preferably from pyridinyl, pyrazolyl, isoxazolyl and thiophenyl, which can all be substituted as indicated, wherein in the respective X is preferably chosen from a direct bond and O. A heteroaryl group representing $R^3$ is preferably bonded to the group X-Het via a ring carbon atom. In one embodiment of the invention the group $R^3$ is phenyl which can be substituted as indicated, wherein in this embodiment X is preferably chosen from a direct bond and O. In another embodiment of the invention the group $R^3$ is phenyl which is substituted as indicated, wherein in this embodiment X is preferably chosen from a direct bond and O. In a substituted group $R^3$ the number of substituents preferably is one, two, three, four or five, more preferably one, two, three or four, particularly preferably one, two or three, more particularly preferably one or two. In one embodiment of the present invention the group $R^3$ is a carbocyclic group, i.e. a phenyl group or a naphthalenyl group, and in another embodiment of the invention the group $R^3$ is a monocyclic group, i.e. a phenyl group or a monocyclic heteroaryl group, where all these groups can be substituted as indicated.

Preferably, the group $R^4$ in the compounds of the formulae I and Ia is chosen from hydrogen and methyl.

The group $R^5$ in the compounds of the formula Ia is preferably defined as in the compounds of the formula I. More preferably, the group $R^5$ in the compounds of the formulae I and Ia is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $CONH_2$, CN, $CF_3$ and $(C_1-C_4)$-alkyl-$SO_2$—. Particularly preferably the group $R^5$ in the compounds of the formulae I and Ia is chosen from halogen, $(C_1-C_4)$-alkyl, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, CN and $CF_3$, more particularly preferably from halogen, $(C_1-C_4)$-alkyl, $NH_2$ and $CF_3$, especially preferably from halogen and $(C_1-C_4)$-alkyl, for example from fluorine, chlorine and methyl. In one embodiment of the invention the group Het in the compounds of the formulae I and Ia is unsubstituted or substituted by one or more identical or different substituents which are chosen from fluorine, chlorine, methyl, $CF_3$ and $NH_2$, and preferably are chosen from fluorine, chlorine and methyl. In another embodiment of the invention the group Het in the compounds of the formulae I and Ia is unsubstituted. The number of substituents $R^5$, which are present on a substituted group Het, preferably is one, two, three or four, more preferably one, two or three, particularly preferably one or two, more particularly preferably one.

The group $R^6$ in the compounds of the formula Ia is preferably defined as in the compounds of the formula I. More preferably the group $R^6$ in the compounds of the formulae I and Ia is chosen from fluorine, $(C_1-C_4)$-alkyloxy, di$((C_1-C_4)$-alkyl)amino, $((C_1-C_4)$-alkyl)-CONH—, di$((C_1-C_4)$-alkyl)aminocarbonyl- and $CF_3$, more particularly preferably from fluorine and $(C_1-C_4)$-alkyloxy. The number of substituents $R^6$ preferably is one, two or three, more preferably one or two, particularly preferably one.

The group $R^7$ in the compounds of the formula Ia is preferably defined as in the compounds of the formula I. More preferably the group $R^7$ in the compounds of the formulae I and Ia is chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_2)$-alkylenedioxy which can be substituted by one or more fluorine atoms, $NH_2$, $(C_1-C_4)$-alkylamino, di$((C_1-C_4)$-alkyl)amino, $((C_1-C_4)$-alkyl)-CONH—, $CONH_2$, CN, $CF_3$, $SF_5$ and $(C_1-C_4)$-alkyl-$SO_2$—, particularly preferably from halogen, $(C_1-C_4)$-alkyl, $(C_1-C_4)$-alkyloxy which can be substituted by one or more fluorine atoms, $(C_1-C_2)$-alkylenedioxy which can be substituted by one or more fluorine atoms, $NH_2$, $(C_1-C_4)$-alkylamino, di$((C_1-C_4)$-alkyl)amino, $CONH_2$, CN, $CF_3$, $SF_5$ and $(C_1-C_4)$-alkyl-$SO_2$—, more particularly preferably from halogen, $(C_1-C_4)$-alkyl, $(C_1-C_4)$-alkyloxy which can be substituted by one or more fluorine atoms, $(C_1-C_2)$-alkylenedioxy which can be substituted by one or more fluorine atoms, CN, $SF_5$ and $CF_3$, especially preferably from halogen, $(C_1-C_4)$-alkyl, $(C_1-C_4)$-alkyloxy which can be substituted by one or more fluorine atoms, CN and $CF_3$. The number of substituents $R^7$ preferably is one, two, three or four, more preferably one, two or three, particularly preferably one or two, for example one.

The group $R^8$ in the compounds of the formula Ia is preferably defined as in the compounds of the formula I. More preferably the group $R^8$ in the compounds of the formulae I and Ia is chosen from fluorine, $(C_1-C_4)$-alkyl, $(C_1-C_4)$-alkyloxy-$(C_1-C_2)$-alkyl-, oxo, $(C_1-C_4)$-alkyloxy which can be substituted by one or more fluorine atoms, $(C_1-C_2)$-alkylenedioxy, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$ and $CF_3$, particularly preferably from fluorine, $(C_1-C_4)$-alkyl, $(C_1-C_4)$-alkyloxy-$(C_1-C_2)$-alkyl-, oxo, $((C_1-C_4)$-alkyloxy)carbonyl- and $CF_3$, more particularly preferably from $(C_1-C_4)$-alkyl, oxo and $((C_1-C_4)$-alkyloxy)carbonyl-, where an oxo substituent representing $R^8$ can of course not be present in an aromatic ring in a ring system formed by $R^1$ and $R^2$ together with the nitrogen atom carrying them. The number of substituents $R^8$ preferably is one, two, three, four or five, more preferably one, two, three or four, particularly preferably one, two or three, more particularly preferably one or two, for example one.

The group $R^9$ in the compounds of the formula Ia is preferably defined as in the compounds of the formula I. More preferably the group $R^9$ in the compounds of the formulae I and Ia is chosen from hydrogen, $(C_1-C_4)$-alkyl and $((C_1-C_4)$-alkyl)-CO—, particularly preferably from hydrogen and $(C_1-C_4)$-alkyl.

Preferably, the group $R^{10}$ in the compounds of the formulae I and Ia is chosen from hydrogen and methyl.

In the compounds of the formula Ia a heteroaryl group is preferably defined as in the compounds of the formula I. Unless stated otherwise in the definition of any group containing a heteroaryl group, a heteroaryl group in the compounds of the formulae I and Ia is more preferably a 5-membered or 6-membered, monocyclic aromatic group which contains one or two identical or different heteroatom ring members chosen from N, $NR^{10}$, O and S. Aromatic heterocyclic residues which can represent heteroaryl occurring in the groups $R^1$, $R^2$ and $R^3$, for example, include pyridinyl, thiophenyl, pyrazolyl, thiazolyl and isoxazolyl.

The number n in the compounds of the formula Ia is preferably defined as in the compounds of the formula I. More preferably the number n in the compounds of the formulae I and Ia is 0 or 1, wherein all numbers n are independent of each other and can be identical or different. An example of the group phenyl-$C_nH_{2n}$— in which the number n is 1 is the benzyl group (=phenyl-$CH_2$—). If a group $C_nH_{2n}$ is substituted by one or more substitutents, it is preferably substituted by one, two, three or four, more preferably by one, two or three, particularly preferably by one or two substituents, for example by one or two alkyl groups or by two fluorine atoms.

In preferred embodiments of the present invention one or more or all of the groups contained in the compounds of formulae I and Ia can independently of each other have any of the preferred definitions of the groups specified above or any one or some of the specific denotations which are comprised by the definitions of the groups and specified herein, all combinations of preferred definitions and/or specific denotations being a subject of the present invention. Also with respect to all preferred embodiments the invention includes the compounds of the formulae I and Ia in all their stereoisomeric forms and mixtures of stereoisomeric forms in all ratios, and their physiologically acceptable salts, as well as their tautomeric forms.

For example, one such embodiment relates to a compound and its use according to the present invention in which in formula I or formula Ia Het is a 5-membered or 6-membered, monocyclic aromatic group which contains one or two identical or different heteroatom ring members chosen from N, $NR^4$, O and S, and which can be substituted on ring carbon atoms by one or more identical or different substituents $R^5$;

X is chosen from a direct bond and O, provided that X cannot be O if the group $R^3$—X— is bonded to a ring nitrogen atom of the group Het;

$R^a$ and $R^b$ are independently of each other chosen from hydrogen and $(C_1-C_4)$-alkyl;

$R^1$ is chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, and $R^2$ is chosen from hydrogen, $(C_1-C_4)$-alkyl, $(C_3-C_7)$-cycloalkyl-$CnH_{2n}$—, phenyl-$C_nH_{2n}$— and heteroaryl-$C_nH_{2n}$—, wherein all $(C_1-C_4)$-alkyl and $(C_3-C_7)$-cycloalkyl groups can be substituted by one or more identical or different substituents $R^6$, and all phenyl and heteroaryl groups can be substituted by one or more identical or different substituents $R^7$, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ together with the nitrogen atom carrying them can be substituted on ring carbon atoms by one or more identical or different substituents $R^8$;

$R^3$ is chosen from phenyl and heteroaryl which can all be substituted by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—;

$R^4$ is chosen from hydrogen and $(C_1-C_4)$-alkyl;

$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $CONH_2$, CN, $CF_3$ and $(C_1-C_4)$-alkyl-$SO_2$—;

$R^6$ is chosen from fluorine, $(C_1-C_4)$-alkyloxy, di$((C_1-C_4)$-alkyl)amino, $((C_1-C_4)$-alkyl)-CONH—, di$((C_1-C_4)$-alkyl)aminocarbonyl- and $CF_3$;

$R^7$ is chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_2)$-alkylenedioxy which can be substituted by one or more fluorine atoms, $NH_2$, $(C_1-C_4)$-alkylamino, di$((C_1-C_4)$-alkyl)amino, $((C_1-C_4)$-alkyl)-CONH—, $CONH_2$, CN, $CF_3$, $SF_5$ and $(C_1-C_4)$-alkyl-$SO_2$—;

$R^8$ is chosen from fluorine, $(C_1-C_4)$-alkyl, $(C_1-C_4)$-alkyloxy-$(C_1-C_2)$-alkyl-, OH, oxo, $(C_1-C_4)$-alkyloxy which can be substituted by one or more fluorine atoms, $(C_1-C_3)$-alkylenedioxy, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN and $CF_3$;

$R^9$ is chosen from hydrogen, $(C_1-C_4)$-alkyl and $((C_1-C_4)$-alkyl)-CO—;

$R^{10}$ is chosen from hydrogen and $(C_1-C_4)$-alkyl;

Heteroaryl is a 5-membered or 6-membered, monocyclic aromatic group which contains one, two or three identical or different heteroatom ring members chosen from N, $NR^{10}$, O and S;

n is 0 or 1, where all numbers n are independent of each other and can be identical or different;

in any of its stereoisomeric forms or a mixture of stereoisomeric forms in any ratio, or a physiologically acceptable salt thereof.

Another such embodiment relates to a compound and its use according to the present invention in which in formula I or formula Ia Het is a 5-membered or 6-membered, monocyclic aromatic group which contains one or two identical or different heteroatom ring members chosen from N, $NR^4$, O and S, and which can be substituted on ring carbon atoms by one or more identical or different substituents $R^5$;

X is chosen from a direct bond and O, provided that X cannot be O if the group $R^3$—X— is bonded to a ring nitrogen atom of the group Het;

$R^a$ and $R^b$ are independently of each other chosen from hydrogen and $(C_1-C_4)$-alkyl;

$R^1$ is chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, and $R^2$ is chosen from hydrogen and $(C_1-C_4)$-alkyl, wherein all $(C_1-C_4)$-alkyl and $(C_3-C_7)$-cycloalkyl groups can be substituted by one or more identical or different substituents $R^6$, and all phenyl and heteroaryl groups can be substituted by one or more identical or different substituents $R^7$, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ together with the nitrogen atom carrying them can be substituted on ring carbon atoms by one or more identical or different substituents $R^8$;

$R^3$ is phenyl which can be substituted by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—;

$R^4$ is chosen from hydrogen and $(C_1-C_4)$-alkyl;

$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $CONH_2$, CN, $CF_3$ and $(C_1-C_4)$-alkyl-$SO_2$—;

$R^6$ is chosen from fluorine and $(C_1-C_4)$-alkyloxy;

$R^7$ is chosen from halogen, $(C_1-C_4)$-alkyl, $(C_1-C_4)$-alkyloxy which can be substituted by one or more fluorine atoms, $(C_1-C_2)$-alkylenedioxy which can be substituted by one or more fluorine atoms, $NH_2$, $(C_1-C_4)$-alkylamino, di$((C_1-C_4)$-alkyl)amino, $((C_1-C_4)$-alkyl)-CONH—, $CONH_2$, CN, $CF_3$, $SF_5$ and $(C_1-C_4)$-alkyl-$SO_2$—;

$R^8$ is chosen from fluorine, $(C_1-C_4)$-alkyl, $(C_1-C_4)$-alkyloxy-$(C_1-C_2)$-alkyl-, oxo, $(C_1-C_4)$-alkyloxy which can be substituted by one or more fluorine atoms, $(C_1-C_2)$-alkylenedioxy, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$ and $CF_3$;

$R^9$ is chosen from hydrogen, $(C_1-C_4)$-alkyl and $((C_1-C_4)$-alkyl)-CO—;

$R^{10}$ is chosen from hydrogen and $(C_1-C_4)$-alkyl;

heteroaryl is a 5-membered or 6-membered, monocyclic aromatic group which contains one or two identical or different heteroatom ring members chosen from N, $NR^{10}$, O and S;

n is 0 or 1, where all numbers n are independent of each other and can be identical or different;

in any of its stereoisomeric forms or a mixture of stereoisomeric forms in any ratio, or a physiologically acceptable salt thereof.

Another such embodiment relates to the use of a compound according to the present invention in which in formula Ia Het is a 5-membered or 6-membered, monocyclic aromatic group which contains one or two identical or different heteroatom ring members chosen from N, $NR^4$, O and S, and which can be substituted on ring carbon atoms by one or more identical or different substituents $R^5$;

X is absent and the phenyl group representing the group $R^3$ is fused to the group Het, $R^a$ and $R^b$ are independently of each other chosen from hydrogen and $(C_1-C_4)$-alkyl;

$R^1$ is chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, and $R^2$ is chosen from hydrogen and $(C_1-C_4)$-alkyl, wherein all $(C_1-C_4)$-alkyl and $(C_3-C_7)$-cycloalkyl groups can be substituted by one or more identical or different substituents $R^6$, and all phenyl and heteroaryl groups can be substituted by one or more identical or different substituents $R^7$, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ together with the nitrogen atom carrying them can be substituted on ring carbon atoms by one or more identical or different substituents $R^8$;

$R^3$ is phenyl which can be substituted by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—;

$R^4$ is chosen from hydrogen and $(C_1-C_4)$-alkyl;

$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $CONH_2$, CN, $CF_3$ and $(C_1-C_4)$-alkyl-$SO_2$—;

$R^6$ is chosen from fluorine and $(C_1-C_4)$-alkyloxy;

$R^7$ is chosen from halogen, $(C_1-C_4)$-alkyl, $(C_1-C_4)$-alkyloxy which can be substituted by one or more fluorine atoms, $(C_1-C_2)$-alkylenedioxy which can be substituted by one or more fluorine atoms, $NH_2$, $(C_1-C_4)$-alkylamino, di$((C_1-C_4)$-alkyl)amino, $((C_1-C_4)$-alkyl)-CONH—, $CONH_2$, CN, $CF_3$, $SF_5$ and $(C_1-C_4)$-alkyl-$SO_2$—;

$R^8$ is chosen from fluorine, $(C_1-C_4)$-alkyl, $(C_1-C_4)$-alkyloxy-$(C_1-C_2)$-alkyl-, oxo, $(C_1-C_4)$-alkyloxy which can be substituted by one or more fluorine atoms, $(C_1-C_2)$-alkylenedioxy, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$ and $CF_3$;

$R^9$ is chosen from hydrogen, $(C_1-C_4)$-alkyl and $((C_1-C_4)$-alkyl)-CO—;

$R^{10}$ is chosen from hydrogen and $(C_1-C_4)$-alkyl;

heteroaryl is a 5-membered or 6-membered, monocyclic aromatic group which contains one or two identical or different heteroatom ring members chosen from N, $NR^{10}$, O and S;

n is 0 or 1, where all numbers n are independent of each other and can be identical or different;

in any of its stereoisomeric forms or a mixture of stereoisomeric forms in any ratio, or a physiologically acceptable salt thereof.

As in any embodiment of the invention, in the preceding embodiments, which contain exemplary definitions of compounds according to the invention, one or more or all of the groups can have any of its preferred definitions specified above or any one or some of the specific denotations which are comprised by their definitions and are specified above.

A further embodiment of the present invention relates to any of the individual compounds of the formulae I and Ia and their use according to the invention which are specifically disclosed herein, including the compounds of all examples described below, in the form of the respective free compound as well as in the form of the physiologically acceptable salts thereof in general and, if a specific salt is disclosed herein, in the form of this specific salt, as well as to all tautomeric forms of the free compounds and their salts if tautomeric forms exist. I.e., this embodiment encompasses the physiologically acceptable salts in general of any individual compound specifically disclosed herein, irrespective thereof whether the compound is specifically disclosed as the free compound or as a specific salt. For example, as regards the compound 3-(6-amino-5-phenyl-pyridin-2-yl)-1-(piperidin-1-yl)-propenone, which is specifically disclosed as the free compound, subjects of the present invention are "3-(6-amino-5-phenyl-pyridin-2-yl)-1-(piperidin-1-yl)-propenone" and "3-(6-amino-5-phenyl-pyridin-2-yl)-1-(piperidin-1-yl)-propenone or a physiologically acceptable salt thereof". As regards the compound 3-[5-(2-fluoro-phenyl)-thiophen-2-yl]-1-(4-methyl-piperazin-1-yl)-propenone, for example, which is specifically disclosed as its trifluoroacetic acid salt, subjects of the present invention are "3-[5-(2-fluoro-phenyl)-thiophen-2-yl]-1-(4-methyl-piperazin-1-yl)-propenone", "3-[5-(2-fluoro-phenyl)-thiophen-2-yl]-1-(4-methyl-piperazin-1-yl)-propenone or a physiologically acceptable salt thereof" and "3-[5-(2-fluoro-phenyl)-thiophen-2-yl]-1-(4-methyl-piperazin-1-yl)-propenone trifluoroacetic acid salt".

A further subject of the present invention are processes of preparation by which the compounds of the formulae I and Ia and salts thereof are obtainable and which are outlined in the following. There are several ways of preparing the compounds by assembling suitable building blocks. The synthetic strategies and the reaction types employed in these synthetic processes are per se known and are described in the literature, including the literature specifically referred to herein, and they can generally be performed under standard conditions which are familiar to one skilled in the art. In part, these processes comprise the reaction of a heteroarylacrylic acid or a derivative thereof of the formula IV with a amine of the formula V to give a compound of the formula I or Ia, where the compound of the formulae IV and/or the compound of the formula V can also be employed, and/or the compound of the formula I or Ia can also be obtained, in the form of a salt.

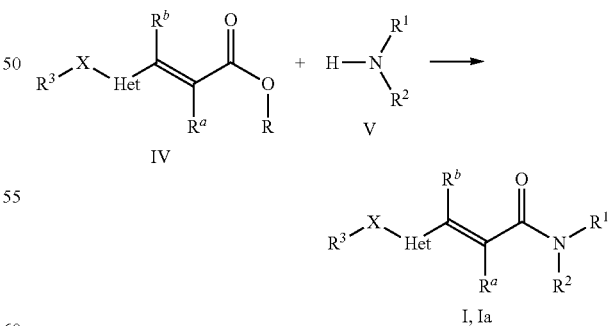

In the compounds of the formulae IV and V the groups Het, X, $R^a$, $R^b$, $R^1$, $R^2$ and $R^3$ are defined as in the compounds of the formulae I and Ia and, in addition, any functional groups can be present in protected form or in the form of precursor groups which are then converted into the desired final groups. As compounds of the formula IV, advantageously carboxylic acids or esters thereof such as an alkyl ester or benzyl ester can be employed, i.e. the group R in the compounds of the formula IV can be hydrogen or alkyl, for example ($C_1$-$C_4$)-alkyl like methyl or ethyl, or benzyl.

The reaction of a compound of the formula IV with a compound of the formula V to give a compound of the formula I or Ia can be performed under standard conditions for the conversion of a carboxylic acid or an ester thereof into a carboxamide or, from a different perspective, for the acylation of an amine by a carboxylic acid or an ester thereof. Compounds of the formula IV in which R is hydrogen, as well as compounds in which R is alkyl or benzyl, can be reacted with a compound of the formula V. If desired or more advantageous in a specific case, a compound of the formula IV in which COOR is a carboxylic acid group COOH can first be esterified and the obtained compound in which COOR is an ester group then reacted with a compound of the formula V. Likewise, a compound of the formula IV in which the group COOR is an ester group can first be cleaved to give the carboxylic acid, for example by acidic or basic saponification or by catalytic hydrogenation in the case of a benzyl ester, and the obtained compound in which COOR is a COOH group then reacted with a compound of the formula V. A compound of the formula IV in which COOR is an ester group, can be reacted with an amine of the formula V by combining the reactants at temperatures from about 20° C. to about 100° C. in a solvent, for example an ether like tetrahydrofuran (THF), dioxane, ethylene glycol dimethyl ether (1,2-dimethoxyethane, DME) or methyl tert-butyl ether (MTB), a hydrocarbon like dichloromethane, toluene or chlorobenzene, an alcohol like methanol, ethanol or isopropanol, an amide like dimethylformamide (DMF) or N-methylpyrrolidone (NMP), or another suitable solvent or a mixture of solvents. In the reaction of a compound of the formula IV in which the group COOR is a carboxylic acid group, preferably the latter group is first activated or converted into a reactive carboxylic acid derivative group. A suitable reactive carboxylic acid derivative is the carboxylic acid chloride, for example, which can be obtained by treatment of the acid with oxalyl chloride or thionyl chloride, for example. Suitable activating reagents for the carboxylic acid group include carbodiimides like N,N'-dicyclohexylcarbodiimide (DCC) or N,N'-diisopropylcarbodiimide (DIC), O-((cyano(ethoxycarbonyl)methylene)amino)-1,1,3,3-tetramethyluronium tetrafluoroborate (TOTU), N,N,N',N'-tetramethyl-O-(7-azabenzotriazol-1-yl)uronium hexafluorophosphate (HATU), propanephosphonic acid anhydride (PPA), N,N'-carbonyldiimidazole (CDI), and chloroformic acid alkyl esters like ethyl chloroformate or isobutyl chloroformate which latter reagents lead to the formation of mixed anhydrides. The acylation of a compound of the formula V with a compound of the formula IV in which the group COOR is a carboxylic acid group, is generally carried out in a solvent such as, for example, toluene, dichloromethane, THF, dioxane, DME, DMF or NMP, in the presence of a base such as, for example, an amine like triethylamine, ethyldiisopropylamine or N-ethylmorpholine (NEM), or a basic alkali metal compound like sodium carbonate, sodium hydrogencarbonate, potassium carbonate or sodium acetate, or in the presence of an excess of the amine of the formula V, at temperatures from about 0° C. to about 80° C.

Compounds of the formula IV can be obtained by different processes. According to one of them, a compound of the formula VI, such as an aldehyde or a ketone, is condensed with a compound of the formula VII in a reaction such as a Knoevenagel reaction, a Wittig reaction or a Wittig-Horner reaction, for example, to provide a heteroarylacrylic acid or derivative thereof of the formula IV.

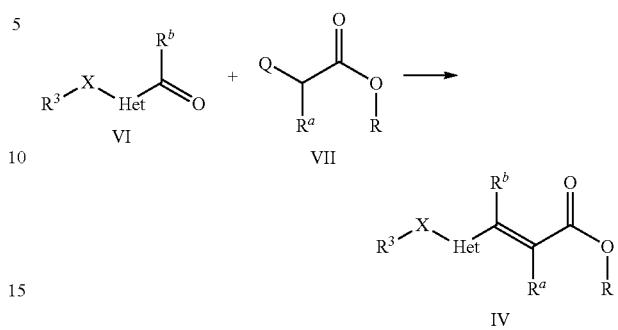

In the compounds of the formulae VI and VII the groups Het, X, $R^a$, $R^b$ and $R^3$ are defined as in the compounds of the formulae I and Ia and, in addition, any functional groups can be present in protected form or in the form of precursor groups which are then converted into the desired final groups. The group R in the compound of the formula VII is defined as in the compound of the formula IV. Depending on the reaction performed, the group Q in the compound of the formula VII can have different meanings. In case a Knoevenagel reaction is performed and $R^a$ denotes hydrogen, the compound of the formula VII can be malonic acid or a malonic acid derivative and the group Q can be a carboxylic acid group COOH or an ester group COOR in which R is ($C_1$-$C_4$)-alkyl or benzyl, for example. In such case the group COOR in the compound of the formula VII can, independently of the group Q, also be a carboxylic acid group COOH or an ester group like —COO—($C_1$-$C_4$)-alkyl. In the Knoevenagel reaction also cyanoacetic acid and cyanoacetic acid derivatives such as ($C_1$-$C_4$)-alkyl esters can be employed, and the group Q can be a cyano group in case of compounds in which $R^a$ is hydrogen. Unless malonic acid or a monoester thereof is employed in the Knoevenagel reaction which generally react with decarboxylation and directly lead to the compound of the formula IV, the formation of a compound of the formula IV from compounds of the formulae VI and VII in a Knoevenagel reaction may include the hydrolysis of an ester group or cyano group which may be performed in situ or in a separate step.

In case a Wittig reaction or a Wittig-Horner reaction is performed, in which case the group COOR in the compounds of the formula VII is an ester group and R is ($C_1$-$C_4$)-alkyl or benzyl, for example, the compound of the formula VII can be a phosphonium salt, for example a (($C_1$-$C_4$)-alkyloxy)carbonylmethyltriphenylphosphonium halide which may carry an alkyl group representing $R^a$ on the methyl group, and the group Q then is a triphenylphosphonio group having a halide anion as counterion, or the compound of the formula VII can be a phosphonate, for example a di(($C_1$-$C_4$)-alkyl) (($C_1$-$C_4$)-alkyloxy)carbonylmethylphosphonate which may carry an alkyl group representing $R^a$ on the methyl group, and the group Q then is a di(($C_1$-$C_4$)-alkyl)phosphonyl group. Instead of employing a (($C_1$-$C_4$)-alkyloxy)carbonylmethyl-triphenylphosphonium halide and deprotonating it when performing the reaction, also a stable phosphorus ylide, for example a (($C_1$-$C_4$)-alkyloxy)carbonylmethylene-triphenylphosphane, can directly be employed in the reaction with the compound of the formula VI.

The above-discussed reactions of compounds of the formulae VI and VII to give compounds of the formula IV can generally be performed under standard conditions. For example, a Knoevenagel reaction with malonic acid or a malonic acid derivative can be performed by heating the reactants to temperatures from about 60° C. to about 120° C. in a solvent, for example a hydrocarbon like benzene, toluene or chlorobenzene, an alcohol like ethanol, or pyridine, preferably in the presence of a base such as an amine like piperidine, pyridine or β-alanine or an acid addition salt of an amine like ammonium acetate. Unless a stable phosphorus ylide is employed directly, a Wittig reaction or a Wittig-Horner reaction for providing a compound of the formula IV is generally performed under anhydrous conditions in a solvent, for example in an ether like THF, dioxane or DME or in an alcohol like ethanol, by first reacting the phosphonium salt or the phosphonate with a base, for example an alkali metal alcoholate like sodium methoxide or potassium tert-butoxide or an amide like lithium diisopropylamide or a hydride like sodium hydride or an organometallic compound like n-butyllithium, and then with a compound of the formula VI at temperatures from about −80° C. to about 100° C.

Heteroarylacrylic acid derivatives of the formula IV can be obtained from aldehydes or ketones of the formula VI also by means of various other reactions which are well-known in the art. As an example, the Perkin reaction may be mentioned which can be applied for preparing compounds of the formula IV in which $R^b$ is hydrogen, and in which the respective aldehyde of the formula VI is heated with an excess of a carboxylic acid anhydride, for example acetic anhydride in case a compound is prepared in which $R^a$ is hydrogen, to temperatures from about 100° C. to about 150° C. in the presence of an alkali metal salt of the carboxylic acid, for example sodium acetate or potassium acetate.

In another process, heteroarylacrylic acids or derivatives thereof of the formula IV can be obtained from compounds of the formula VIII and acrylic acid derivatives of the formula IX in a Heck reaction.

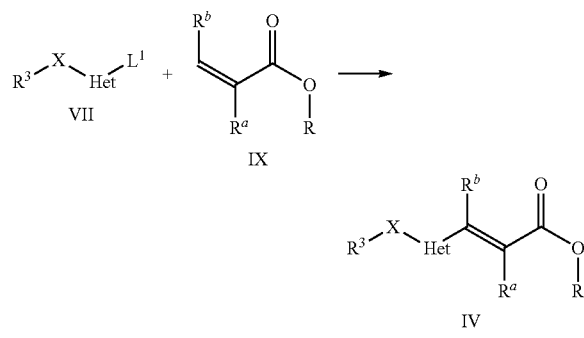

In the compounds of the formulae VIII and IX the groups Het, X, $R^a$, $R^b$ and $R^3$ are defined as in the compounds of the formulae I and Ia and, in addition, any functional groups can be present in protected form or in the form of precursor groups which are then converted into the desired final groups.

The group COOR in the acrylic acid derivatives of the formula IX preferably is an ester group and R is alkyl such ($C_1$-$C_4$)-alkyl, like methyl or ethyl, or benzyl, for example. The group $L^1$ in the compounds of the formula VIII is a leaving group which is substitutable by an alkene moiety under the conditions of the Heck reaction, such as halogen, for example chlorine, bromine or iodine, or a sulfonyloxy group, for example trifluoromethanesulfonyloxy. Generally, the reaction is performed in the presence of a transition metal catalyst, such as a palladium catalyst, for example palladium acetate in the presence of a phosphane like triphenylphosphane or tri(ortho-tolyl)phosphane, or bis(triphenylphosphane)palladium chloride or tetrakis(triphenylphosphane) palladium, and a base, such as an amine, for example a tertiary amine like triethylamine, or a basic alkali metal salt, for example potassium carbonate or sodium acetate, in an inert solvent, such as a hydrocarbon, for example toluene, chlorobenzene or dichloromethane, an ether, for example DME, THF or dioxane, an amide, for example DMF or NMP, a nitrile, for example acetonitrile, or a mixture of solvents, at temperatures from about 20° C. to about 110° C.

The compounds of the formulae VI, VII, VIII and IX as well as the compounds of the formula V and other starting compounds which are employed in the processes for the preparation of intermediates and the final compounds of the formulae I and Ia discussed herein, are commercially available or can be prepared according to standard procedures described in the literature or in analogy to such procedures. For example, aldehydes and ketones of the formula VI can be obtained by such procedures from the parent heteroarenes of the formula $R^3$—X—Het-H or respective substituted heteroarenes which carry a substituent such as halogen, alkyl, carboxy, alkoxycarbonyl or cyano, for example, by means of a reaction such as a Friedel-Crafts acylation, a Vilsmeier formylation, a metalation followed by reaction with a carboxylic acid derivative, a halogenation of an alkyl group followed by hydrolysis, an oxidation of an alkyl group, or a reduction or a reaction with an organometallic compound of a cyano or carboxy group or a derivative thereof. Compounds of the formula VIII can be obtained, for example, from the parent heteroarenes or respective substituted heteroarenes which carry a substituent such as hydroxy or amino by means of a reaction such as a halogenation of the parent heteroarene or a hydroxy-substituted heteroarene, a sulfonylation of a hydroxy group, or a diazotization of an amino group followed by reaction with halide.

The structural moiety $R^3$—X may already be present in the compounds of the formulae VI and VIII which are available or may be obtained as outlined afore, or it may be introduced by standard procedures in starting compounds of the compounds of the formulae VI and VII or their starting compounds. For example, compounds of the formulae VI and VIII may be obtained from appropriate starting compounds of the formulae X and XIII, or the formulae XIV and XV, respectively, by reaction with appropriate compounds of the formulae XI and XII.

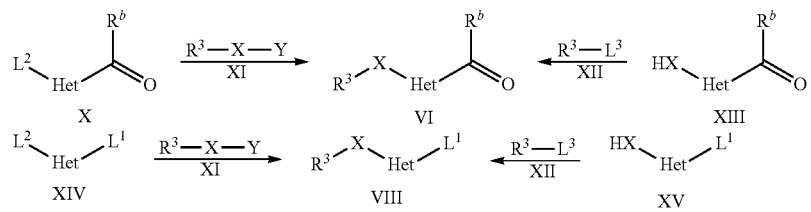

In the compounds of the formulae X, XI, XII, XIII, XIV and XV the groups Het, $R^b$ and $R^3$ are defined as in the compounds of the formulae I and Ia and, in addition, any functional groups can be present in protected form or in the form of precursor groups which are then converted into the desired final groups. When performing the contemplated processes, also the C=O group in the compounds of formulae X and XIII, which is depicted in the formulae, can be present in protected form or in the form of a precursor group. The group X in the compounds of the formula XIII and XV is chosen from O, O—$CH_2$, S, NH and N($(C_1$-$C_4)$-alkyl). The group X in the compound of the formula XI is chosen from a direct bond, $CH_2$, O, O—$CH_2$, $CH_2$—O, S, NH and N($(C_1$-$C_4)$-alkyl). In case the group X in the compound of the formula XI and the obtained compound of the formula VI or VII is O, $CH_2$—O, S, NH or N($(C_1$-$C_4)$-alkyl), the group Y in the compound of the formula XI is hydrogen. In case the group X in the compound of the formula XI and the obtained compound of the formula VI or VIII is a direct bond, the group Y can be a boronic acid group or a derivative thereof, for example a boronic acid group —$B(OH)_2$, and the compound of the formula XI thus can be a boronic acid of the formula $R^3$—$B(OH)_2$. In case the group X in the compound of the formula XI is $CH_2$ or O—$CH_2$, the group Y can be a nucleophilically substitutable leaving group, for example halogen, in particular chlorine and bromine, or an arylsulfonyloxy or alkylsulfonyloxy group such as benzenesulfonyloxy, toluenesulfonyloxy, nitrobenzenesulfonyloxy, methanesulfonyloxy or trifluoromethanesulfonyloxy, and the compound of the formula XI thus can be an alkylating agent. The group $L^1$ in the compounds of formulae XIV and XV is defined as in the compound of the formula VIII or can be present in the form of a precursor group which is then converted into the desired group $L^1$, for example a hydroxy group or a protected hydroxyl group which can be converted into a trifluoromethanesulfonyloxy leaving group by treatment with trifluoromethanesulfonyl chloride. The group $L^2$ in the compounds of formulae X and XIV is a leaving group which can be replaced with the group $R^3$—X— in a catalyzed or uncatalyzed nucleophilic aromatic substitution reaction or coupling reaction or a reaction of another type as it is performed when reacting the compounds of the formulae X and XI or XIV and XI. Examples of suitable leaving groups $L^2$ in the compounds of the formulae X and XIV are halogen, in particular chlorine, bromine and iodine, and sulfonyloxy groups such as trifluoromethanesulfonyloxy. The group $L^2$ in the compound of the formula XIV can be identical to or different from the group $L^1$. If $L^1$ is a leaving group, the formation of the desired product of the formula VIII in the reaction of the compounds of the formulae XIV and XI can be achieved by applying suitable reaction conditions and employing a compound of the formula XIV which contains two leaving groups $L^1$ and $L^2$ of different reactivity, or taking advantage of different reactivities of leaving groups which are present in different positions of the group Het in case $L^1$ and $L^2$ are identical. The latter situation applies to a compound of the formula XIV such as 2,5-dibromopyridine, for example, in which the bromine atom in the 2-position is more reactive than the bromine atom in the 5-position. The group $L^3$ in the compound of the formula XII likewise is a nucleophilically substitutable leaving group and can be halogen, in particular chlorine, bromine and iodine, or a sulfonyloxy group like trifluoromethanesulfonyloxy, for example.

The reactions of the compounds of the formulae X and XIV with a compound of the formula XI and of the compounds of the formulae XIII and XV with a compound of the formula XII are generally performed in the presence of a base which binds the liberated acid of the formula $L^2$-H or $L^3$-H and/or enhances the nucleophilicity of compounds of the formulae XI, XIII and XV which are alcohols, thiols or amines. Suitable bases include amines, for example tertiary amines like triethylamine, ethyldiisopropylamine, pyridine, amide salts, for example sodium amide or lithium diisopropylamide, organometallic compounds, for example organolithium compounds like n-butyllithium, alkali metal or alkaline earth metal hydrides, for example lithium hydride, sodium hydride or calcium hydride, alkali metal or alkaline earth metal hydroxides or quaternary ammonium hydroxides, for example lithium hydroxide, sodium hydroxide, potassium hydroxide, calcium hydroxide, benzyltrimethyl-ammonium hydroxide, alkali metal or alkaline earth metal alkoxides, for example sodium methoxide, sodium ethoxide, potassium methoxide, potassium ethoxide, potassium tert-butoxide, or other basic alkaline metal or alkaline earth metal compounds, for example carbonates like sodium carbonate, potassium carbonate, cesium carbonate, hydrogencarbonates like sodium hydrogencarbonate, potassium hydrogencarbonate, or other basic salts, or a mixture of bases. By means of the base, the compounds of the formula XI, XIII and XV, which are alcohols, thiols or amines, can initially be converted into their corresponding salts. The reactions, which are nucleophilic arylation reactions and which can be performed in the presence or absence of a catalyst such as transition metal compound, are usually carried out in an inert solvent, such as a hydrocarbon or chlorinated hydrocarbon, for example n-heptane, toluene, xylene, chlorobenzene, dichloromethane, an ether, for example diethyl ether, diisopropyl ether, DME, THF, dioxane, an ester, for example ethyl acetate, butyl acetate, an amide, for example DMF, NMP, a nitrile, for example acetonitrile, an alcohol, for example methanol, ethanol, isopropanol, n-butanol, or another solvent, for example pyridine or dimethyl sulfoxide (DMSO), or a mixture of solvents. The reactions are generally performed at temperatures from about −20° C. to about 130° C.

In case the group X is a direct bond and the group Y in the compound of the formula XI is a boronic acid group —$B(OH)_2$ or a derivative thereof, the reaction of the compound of the formula XI with a compound of the formula X or XIV to give a compound of the formula VI or VIII, in which X is a direct bond, can be carried out under the conditions of the well known Suzuki coupling, or Suzuki-Miyaura coupling, in the presence of a transition metal catalyst in an aqueous or non-aqueous solvent, for example a mixture of an ether such as DME and water. Suitable catalysts include palladium catalysts, for example tetrakis(triphenylphosphane) palladium and palladium acetate. Details on such coupling reactions of boronic acid derivatives, which can advantageously be used also in other processes for the preparation of the compounds of the invention, and intermediates therefor are explained in Kotha et al., Tetrahedron 58 (2002) 9633; Miyaura, Topics in Current Chemistry 219 (2002) 11; or Walker et al., Angew. Chem. Ind. Ed. 43 (2004) 1871, for example. If the group X is $CH_2$ or O—$CH_2$ and the compound of the formula XI is an alkylating agent as specified above, the reaction of a compound of the formula XI with a compound of the formula X or XIV to give a compound of the formula VI or VIII, in which X is $CH_2$ or O—$CH_2$, can be carried out by metalating the compound of the formulae X or XIV, for example by means of an organolithium compound such as n-butyllithium, and then alkylating it with the compound of the formula XI or reacting it with an aldehyde of the formula $R^3$—CHO to give a compound containing the group $R^3$—CH(OH)— which is then reduced to the group $R^3$—$CH_2$—. An $R^3$—$CH_2$— group representing the group $R^3$—X— can also be introduced into a compound of the invention by performing an acylation reaction with a suitable starting compound to give a compound which contains the group $R^3$—CO— and reducing this group to the group $R^3$—$CH_2$—. As is usual and applies to all reactions performed in the synthesis of a compound of the invention, the detailed conditions of a specific preparation, including the solvent, the base, the temperature, the order of addition, the molar ratios and other parameters, are routinely chosen by the skilled person in view of the characteristics of the starting compounds and the target compound.

The order in which the structural moieties in a compound of the invention are introduced to give the final compound of the formula I or Ia, is variable and can be adapted to the needs and desire in a specific case. For example, besides by the processes for the preparation of the intermediates of the formula IV outlined above in which the group $R^3$—X— is present in the starting compounds of the formulae VI and VIII which are reacted with the compounds of the formulae VII and IX, respectively, just so the starting compounds of the formulae X and VII, or the starting compounds of the formulae XIV and IX, may be reacted to give the intermediate of the formula XVI which does not yet contain the group $R^3$—X— and in which this group is introduced by reaction with a compound of the formula XI to give a compound of the formula IV.

formulae XIII and VII, or the starting compounds of the formulae XV and IX, may be reacted to give an intermediate which differs from the compound of the formula XVI in that it contains a group HX— instead of the group $L^2$, wherein X is chosen from O, O—$CH_2$, S, NH and N(($C_1$-$C_4$)-alkyl) and into which the group $R^3$ is then introduced by reaction with a compound of the formula XII to give a compound of the formula IV.

Instead of introducing the moiety —$NR^1R^2$ at the final stage of the synthesis of a compound of the formula I or Ia by reacting an intermediate of the formula IV with an amine of the formula V, it is also possible to introduce the said moiety at an earlier stage. For example, a compound of the formula XVI, which can be prepared as outlined afore, can be reacted with an amine of the formula V to give a compound of the formula XVII which is then reacted with a compound of the formula XI to give a compound of the formula I or Ia.

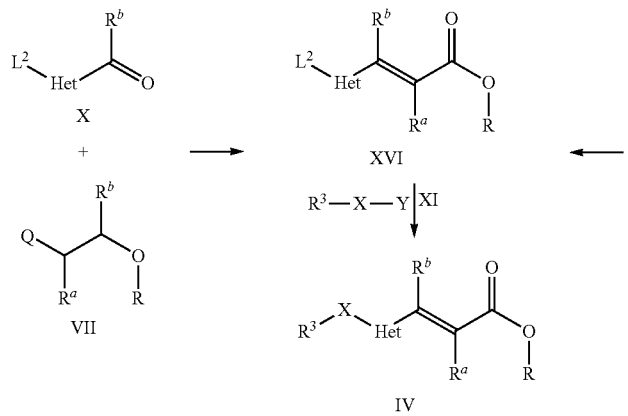

In the compound of the formula XVI the groups Het, $R^a$ and $R^b$ are defined as in the compounds of the formulae I and Ia and, in addition, any functional groups can be present in protected form or in the form of precursor groups which are then converted into the desired final groups. The group R in the compound of the formula XVI is defined as in the compound of the formula IV and can thus be hydrogen, ($C_1$-$C_4$)-alkyl or benzyl, for example, and the group $L^2$ is defined as in the compounds of the formulae X and XIV. The explanations given above on the reaction of the compound of the formula VI with the compound of the formula VII, the reaction of the compound of the formula VIII with the compound of the formula IX, and the reaction of the compounds of the formulae X and XIV with the compound of the formula XI apply correspondingly to the reaction of the compound of the formula X with the compound of the formula VII, the reaction of the compound of the formula XIV with the compound of the formula IX, and the reaction of the compound of the formula XVI with the compound of the formula XI, respectively. Similarly as explained above, the formation of a compound of the formula XVI in which R is hydrogen may thus include the cleavage of an ester group to provide a carboxylic acid group. Analogously, in a further approach for the synthesis of a compound of the formula IV, the starting compounds of the

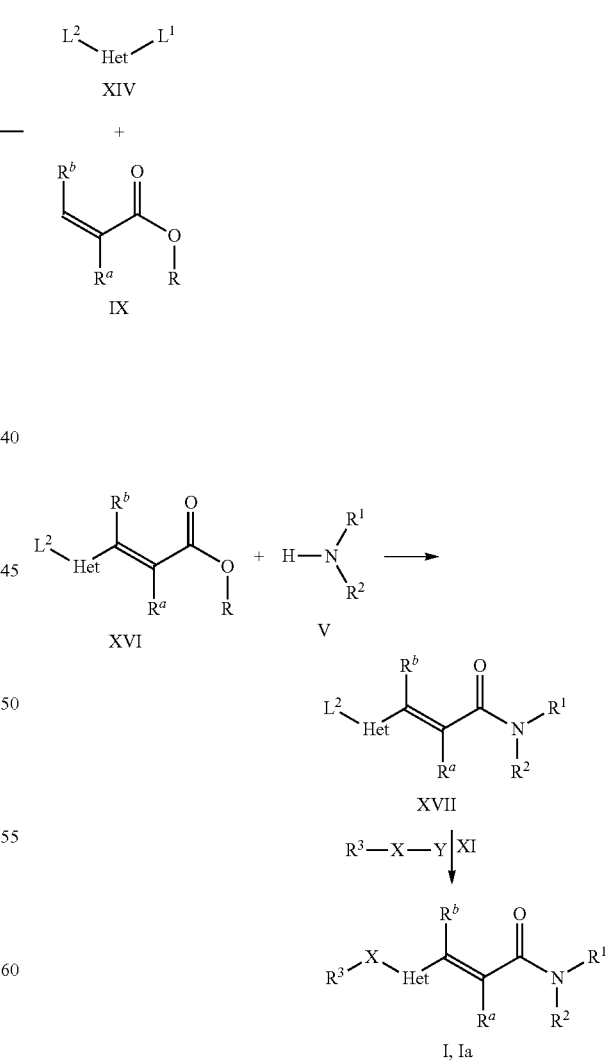

In the compound of the formula XVII the groups Het, $R^a$, $R^b$, $R^1$ and $R^2$ are defined as in the compounds of the formulae I and Ia and, in addition, any functional groups can be present in protected form or in the form of precursor groups which are then converted into the desired final groups. The explanations given above on the reaction of the compound of the formula IV with the compound of the formula V, and on the reaction of the compounds of the formulae X and XIV with the compound of the formula XI, apply correspondingly to the reaction of the compound of the formula XVI with the compound of the formula V, and the reaction of the compound of the formula XVI with the compound of the formula XI, respectively. Thus, for example, a compound of the formula XVI in which the group COOR is an ester group as well as a compound in which the group COOR is a carboxylic acid group COOH can be reacted with a compound of the formula V, where in the latter case the carboxylic acid group is preferably activated or converted into a reactive carboxylic acid derivative group, for example into the carboxylic acid chloride. As explained above, in case the group X is a direct bond, the group $R^3$—X is preferably introduced by means of a compound of the formula XI in which Y is a boronic acid group or a derivative thereof, for example a boronic acid of the formula $R^3$—$B(OH)_2$, under the conditions of the Suzuki reaction.

Further synthetic strategies for the preparation of compounds of the invention include the assembly of the group Het in a ring-forming reaction from starting compounds which may contain the groups $R^3$—X— or part of this group or a protected form or precursor thereof which is then modified in subsequent reaction steps. For example, compounds of the formulae I and Ia in which the group Het is a thiazole ring and the group X is a direct bond, can be prepared by reacting a 2-bromo-1-$R^3$-ethanone of the formula XVIII, in which the $CH_2$ group can optionally be substituted by a suitable substituent representing $R^5$, for example an alkyl substituent, with a 2-oxo-thiocarboxamide in which the oxo group is protected, for example as a ketal or acetal, for example with a 2,2-diethoxythioacetamide derivative of the formula XIX, to give a compound of the formula XX. Subsequent deprotection of the oxo group yields a compound of the formula VIa which is then reacted with a compound of the formula VII, for example in a Wittig reaction or a Wittig-Horner reaction, to give an intermediate of the formula IVa whose reaction with an amine of the formula V finally provides a compound of the formula I or Ia.

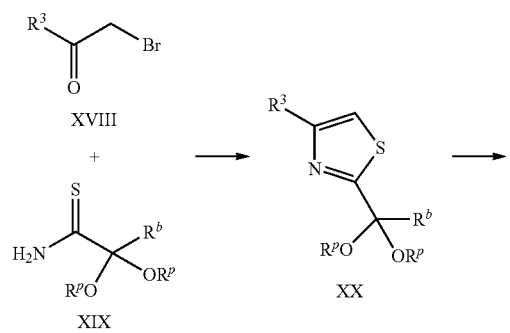

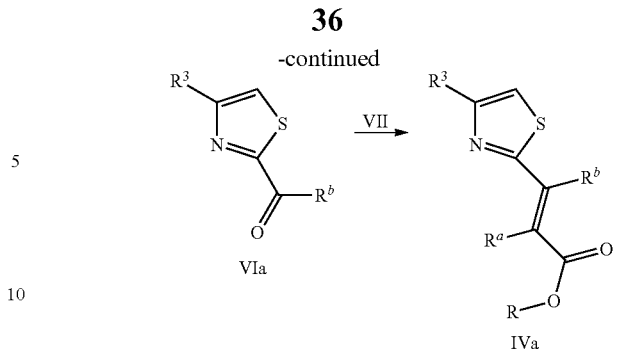

In the compounds of the formulae XVIII, XIX, XX, VIa and IVa the groups $R^a$, $R^b$ and $R^3$ are defined as in the compounds of the formulae I and Ia and, in addition, any functional groups can be present in protected form or in the form of precursor groups which are then converted into the desired final groups. Like the $CH_2$ group in the compound of the formula XVIII, the thiazole ring in the compounds of the formulae XX, VIa and IVa can be substituted by a suitable substituent such as an alkyl group. The group R in the compound of the formula IVa is defined as in the compound of the formula IV and can thus be hydrogen, $(C_1-C_4)$-alkyl or benzyl, for example, where the formation of a compound of the formula IVa in which R is hydrogen may include the cleavage of an initially formed ester. The groups $R^p$ in the compounds of the formulae XIX and XX can be alkyl groups, such as methyl or ethyl, or together be an alkanediyl group, such as an 1,2-ethanediyl group. The reaction of the compounds of the formulae XVIII and XIX is generally carried out in a solvent, for example an alcohol like as methanol or ethanol, an ester like ethyl acetate or butyl acetate, or an ether like THF, dioxane or DME, at temperatures from about 20° C. to about 80° C. The cleavage of the acetal or ketal group in the compound of the formula XX to give the free oxo group can be performed by treatment with a dilute acid, for example hydrochloric acid or sulfuric acid, at temperatures from about 20° C. to about 60° C., and the subsequent reaction with the compound of the formula VII under the condition outlined above with respect to the reaction of the compounds of the formulae VI and VII.

As another example of a process for the preparation of compounds of the invention which includes the assembly of the group Het in a ring-forming reaction, the preparation of compounds in which the group Het is a pyrimidine ring, the group X is a direct bond and the group $R^b$ is hydrogen, may be mentioned. Such compounds can be obtained by reacting an amidine of the formula XXI with a suitable triformylmethane derivative, for example a 2-dimethylaminomethylene-1,3-bis (dimethylimmonio)propane salt like the bis(tetrafluoroborate) of the formula XXII which is described in M. Keshavarz-K. et al., Synthesis (1988) 641, with subsequent hydrolysis of the dimethylimmonio group to give the a compound of the formula VIb which is then reacted with a compound of the formula VII, for example in a Knoevenagel reaction, to give an intermediate of the formula IVb whose reaction with an amine of the formula V finally provides a compound of the formula I or Ia.

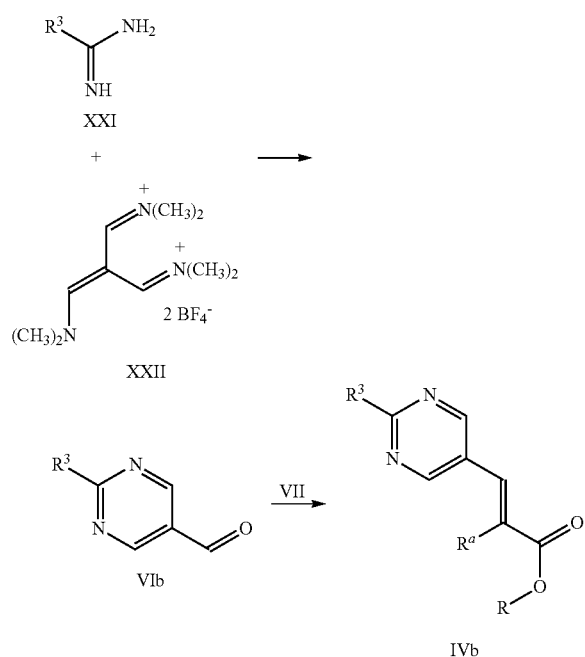

In the compounds of the formulae XXI, XXII, VIb and IVb the groups $R^a$ and $R^3$ are defined as in the compounds of the formulae I and Ia and, in addition, any functional groups can be present in protected form or in the form of precursor groups which are then converted into the desired final groups. The group R in the compound of the formula IVb is defined as in the compound of the formula IV and can thus be hydrogen, $(C_1\text{-}C_4)$-alkyl or benzyl, for example, where the formation of a compound of the formula IVb in which R is hydrogen may include an ester cleavage. As applies to starting materials in processes for the preparation of compounds of the formulae I and Ia in general, the compounds of the formula XXI may also be employed in the form of salts, for example acid addition salts with hydrochloric acid. The reaction of the compound of the formula XXI or its salt with the compound of the formula XXII is generally carried out in a solvent, for example an alcohol like methanol or ethanol, an ether like THF, dioxane or DME, or an amide like DMF or NMP, in the presence of a base, for example an alkali metal alkoxide like sodium methoxide, sodium ethoxide or potassium tert-butoxide, at temperatures from about 20° C. to about 100° C. After treatment of the reaction mixture with water, the obtained aldehyde of the formula VIb is then with a compound of the formula VII under the condition outlined above with respect to the reaction of the compounds of the formulae VI and VII.

Further compounds of the formulae I and Ia can be obtained from suitable intermediates or compounds of the formulae I and Ia prepared according to the above-described processes by functionalization or modification of contained functional groups according standard procedures, for example by esterification, amidation, hydrolysis, etherification, alkylation, acylation, sulfonylation, oxidation, reduction, conversion into salts, and others. As specific examples of oxidation reactions, the oxidation of ring nitrogen atoms to give N-oxides and the oxidation of sulfur atoms to give sulfoxides or sulfones may be mentioned, which are preferably carried out with hydrogen peroxide or a peracid such as 3-chloroperbenzoic acid.

All reactions used in the above-described syntheses of the compounds of the formulae I and Ia are per se well-known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. As already indicated above, depending on the circumstances of the individual case, in order to avoid an unwanted course of a reaction or side reactions during the synthesis of a compound, it can generally be necessary or advantageous to temporarily block functional groups by introducing protective groups and deprotect them at a later stage of the synthesis, or introduce functional groups in the form of precursor groups which later are converted into the desired functional groups. As examples of protecting groups, amino protecting groups such as the tert-butyloxycarbonyl group (Boc) which can be removed by treatment with trifluoroacetic acid (TFA), the benzyloxycarbonyl group which can be removed by catalytic hydrogenation, or the fluoren-9-ylmethoxycarbonyl group which can be removed by treatment with piperidine, carboxylic acid protecting groups such as the tert-butyl ester group which can be deprotected by treatment with TFA, or the benzyl ester group which can be deprotected by catalytic hydrogenation, or aldehyde and ketone protecting groups such as the dimethyl or diethyl acetal group and ketal group or the ethylene acetal group and ketal group which can be deprotected with dilute acid, may be mentioned. As an example of a precursor group the nitro group may be mentioned which can be converted into an amino group by reduction, for example by catalytic hydrogenation. Such synthesis strategies, and protective groups and precursor groups which are suitable in a specific case, are known to the skilled person. If desired, the obtained compounds of formulae I and Ia, as well as any intermediate compounds, can be purified by customary purification procedures, for example by recrystallization or chromatography.

The compounds of the formulae I and Ia are useful pharmacologically active, or pharmaceutically active compounds, which modulate the expression of endothelial NO synthase, and more specifically upregulate, or stimulate, the expression, or transcription, of endothelial NO synthase, and which can be employed as pharmaceuticals, or active ingredients of medicaments, for the treatment of various diseases. In the context of the present invention, treatment is understood as comprising both therapy, including alleviation and cure, of diseases and disease symptoms and prevention and prophylaxis of diseases and disease symptoms, such as, for example, the prevention of the appearance of asthmatic disease symptoms or the prevention of myocardial infarction or of myocardial reinfarction in affected patients. The diseases or disease symptoms can be acute or chronic. Diseases which can be treated with the compounds of the formulae I and Ia include, for example, cardiovascular diseases like stable and unstable angina pectoris, coronary heart disease, coronary artery disease, Prinzmetal angina (spasm), acute coronary syndrome, cardiac insufficiency, heart failure, myocardial infarction, stroke, thrombosis, peripheral artery occlusive disease (=PAOD), endothelial dysfunction, atherosclerosis, restenosis, endothelial damage after PTCA (=percutaneous transluminal coronary angioplasty), hypertension including essential hypertension, pulmonary hypertension and secondary hypertension (renovascular hypertension, chronic glomerulonephritis), erectile dysfunction, and ventricular arrhythmia. Further, the compounds of the formulae I and Ia can be used to lower the cardiovascular risk of postmenopausal women or after intake of contraceptives. Compounds of the formulae I and Ia can additionally be used in the treatment, including therapy and prevention, of diabetes and diabetes complications such as nephropathy or retinopathy, angiogenesis, asthma bronchial, chronic renal failure, cirrhosis of the liver, osteoporosis, restricted memory performance or a restricted ability to learn. Preferred indications are stable angina pectoris, coronary heart disease, cardiac insufficiency, hypertension, endothelial dysfunction, atherosclerosis and diabetes complications.

The compounds of the formulae I and Ia can be used in combination with other pharmacologically active compounds or pharmaceuticals, preferably with compounds which are able to enhance the effect of the compounds according to the formulae I and Ia. Examples of such other compounds include statins; ACE inhibitors; AT1 antagonists; argininase inhibitors; PDE V inhibitors; calcium antagonists; alpha blockers; beta blockers; metimazol and analogous compounds; arginine; tetrahydrobiopterin; vitamins, in particular vitamin C and vitamin B6; niacine.

The compounds of the formulae I and Ia and their physiologically acceptable salts, optionally in combination with other pharmacologically active compounds, can be administered to animals, preferably to mammals, and in particular to humans, as pharmaceuticals by themselves, in mixtures with one another, or in the form of pharmaceutical compositions. Further subjects of the present invention therefore also are the compounds of the formulae I and Ia and their physiologically acceptable salts for use as pharmaceuticals, their use as modulating agents, and more specifically as stimulating agents or upregulating agents, of the expression or transcription of endothelial NO synthase, for example in conditions in which an increased expression of said enzyme or an increased NO level or the normalization of a decreased NO level in a patient is desired, and in particular their use in the treatment, including therapy and prevention, of the above-mentioned diseases or syndromes, as well as their use for the preparation or manufacture of medicaments for these purposes. Furthermore, a subject of the present invention are pharmaceutical compositions, or pharmaceutical preparations, which comprise at least one compound of the formulae I or Ia and/or a physiologically acceptable salt thereof and a pharmaceutically acceptable carrier, i.e. one or more pharmaceutically acceptable carrier substances and/or additives.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously, for example in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, among others, on the disease to be treated and on its severity.

The amount of a compound of the formula I or Ia and/or its physiologically acceptable salts present in the pharmaceutical compositions is chosen such that it is effective for the desired purpose, and normally ranges from about 0.2 to about 800 mg, preferably from about 0.5 to about 500 mg, in particular from about 1 to about 200 mg, per dose, but depending on the type of the pharmaceutical composition it may also be higher. The pharmaceutical compositions usually comprise from about 0.5 to about 90 percent by weight of the compounds of the formulae I or Ia and/or their physiologically acceptable salts. The production of the pharmaceutical compositions can be carried out in a manner known per se. To this end, one or more compounds of the formulae I or Ia and/or their physiologically acceptable salts together with one or more solid or liquid pharmaceutical carrier substances (or vehicles) and/or additives (or auxiliary substances) and, if a combination medicament is desired, other pharmacologically active compounds having therapeutic or prophylactic action are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, starch derivatives, talc, stearic acid or its salts, etc. Soft gelatin capsules and suppositories can comprise, for example, fats, waxes, semisolid and liquid polyols, natural or hardened oils, etc. Suitable carrier substances for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formulae I and Ia and their physiologically acceptable salts and to use the resulting lyophilisates, for example, for preparing compositions for injection or infusion. Suitable carriers for microcapsules, implants or rods are, for example, copolymers of glycolic acid and lactic acid. Besides the compound or compounds according to the invention and carrier substances, the pharmaceutical compositions can also contain additives such as, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formula I or Ia to be administered and/or of a physiologically acceptable salt thereof depends on the individual case and, as is customary, has to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compound used, on whether the use is for the therapy of a acute or chronic disease or prophylactic, or on whether other active compounds are administered in addition to compound of the formula I or Ia. In general, a daily dose from about 0.01 mg/kg to about 100 mg/kg, preferably from about 0.1 mg/kg to about 10 mg/kg, in particular from about 0.3 mg/kg to about 5 mg/kg (in each case mg per kg of bodyweight) is appropriate for administration to an adult weighing about 75 kg in order to obtain the desired results. The daily dose can be administered in a single dose or, in particular when larger amounts are administered, divided into several, for example two, three or four individual doses. In some cases, depending on the individual response, it may be necessary to deviate upwards or downwards from the given daily dose.

The compounds of the formulae I and Ia can also be used for other purposes than those indicated in the foregoing. Non-limiting examples include the use as diagnostics, for example the use in methods for determining the activity of endothelial NO synthase in biological samples, the use as biochemical tools and the use as intermediates for the preparation of further compounds, for example further pharmacologically active compounds.

EXAMPLES

Compounds containing a basic group which were purified by preparative high pressure liquid chromatography (HPLC), specifically on reversed phase (RP) material, using an eluent which contained trifluoroacetic acid, were in part obtained in the form of acid addition salts with trifluoroacetic acid (TFA) which is not depicted in the formulae in the examples. The compounds were characterized by analytical HPLC and/or mass spectrometry (MS) and/or nuclear magnetic resonance spectrometry (NMR).

Example 1

1-(Piperidin-1-yl)-3-(quinolin-3-yl)-propenone

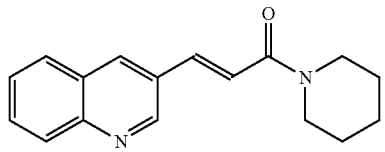

(a) 3-(Quinolin-3-yl)-acrylic Acid 1.006 g (6.4 mmol) of quinoline-3-carbaldehyde were dissolved in 10 ml of pyridine and 0.794 g (7.6 mmol) of malonic acid and 54 mg (0.6 mmol) of piperidine were added. The resulting solution was boiled under reflux for 6 h. The solution was allowed to cool to room temperature and kept for 16 h whereupon the product precipitated. The product was isolated by filtration. Yield: 0.765 g.

MS: m/e=200 (M+H)$^+$

(b) 1-(Piperidin-1-yl)-3-(quinolin-3-yl)-propenone 0.25 g (1.3 mmol) of 3-(quinolin-3-yl)-acrylic acid, 1.445 g (12.5 mmol) of NEM and 453 mg (1.4 mmol) of TOTU were dissolved in 2 ml of DMF and stirred at room temperature for 15 min. 117 mg (1.4 mmol) of piperidine were added, and reaction mixture was stirred at room temperature for 16 h. The solvent was removed under reduced pressure. The residue was dissolved in ethyl acetate, and the solution was washed with a saturated aqueous sodium hydrogencarbonate solution. The organic phase was dried with sodium sulfate, filtered and the solvent was removed under reduced pressure. Yield: 312 mg.

MS: m/e=267 (M+H)$^+$

Example 2

3-[5-(4-Chloro-phenyl)-thiophen-2-yl]-1-(piperidin-1-yl)-propenone

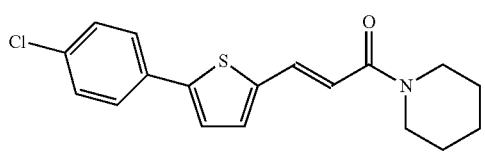

(a) 3-(5-Bromo-thiophen-2-yl)-acrylic Acid 3 g (15.7 mmol) of 5-bromo-thiophene-2-carbaldehyde were dissolved in 30 ml of pyridine and 1.96 g (18.8 mmol) of malonic acid and 133 mg (1.6 mmol) of piperidine was added. The reaction mixture was boiled under reflux for 6 h. After cooling to room temperature, it was poured into a mixture of ice and concentrated aqueous hydrochloric acid whereupon the product precipitated. The product was isolated by filtration, dissolved in ethyl acetate, and the solution was washed with 0.1 M hydrochloric acid. The organic phase was dried with sodium sulfate, filtered and the solvent was removed under reduced pressure. Yield: 3.0 g.

MS: m/e=234 (M+H)$^+$

(b) 3-[5-(4-Chloro-phenyl)-thiophen-2-yl]-acrylic Acid 0.250 g (1.1 mmol) of 3-(5-bromo-thiophen-2-yl)-acrylic acid and 61.9 mg (0.1 mmol) of tetrakis(triphenylphosphine)palladium were dissolved in 5 ml of degassed DME and stirred for 10 min at room temperature. 0.251 g (1.6 mmol) of 4-chlorophenylboronic acid and 1 ml of a 2 M aqueous sodium carbonate solution were added together with an additional 5 ml of degassed DME. The reaction mixture was heated to 95° C. for 4 h, and then stirred at room temperature for 16 h. Solids were removed by filtration and the resulting solution was evaporated to dryness. The residue was dissolved in ethyl acetate and washed three times with a saturated aqueous sodium hydrogencarbonate solution, and once with a saturated sodium chloride solution. The organic phase was dried with sodium sulfate, filtered, and the solvent was removed under reduced pressure. The product was purified by silica gel chromatography. Yield: 0.12 g.

MS: m/e=265 (M+H)$^+$

(c) 3-[5-(4-Chloro-phenyl)-thiophen-2-yl]-1-(piperidin-1-yl)-propenone 0.12 g (0.5 mmol) of 3-[5-(4-chloro-phenyl)-thiophen-2-yl]-acrylic acid, 522 mg (4.5 mmol) of NEM and 163 mg (0.5 mmol) of TOTU were dissolved in 3 ml of DMF and stirred at room temperature for 15 min. 42.5 mg (0.5 mmol) of piperidine were added, and the reaction mixture was stirred at room temperature for 16 h. After filtration and evaporation, and the product was purified by preparative RP HPLC eluting with a gradient of 0 to 100% acetonitrile in water (+0.01% TFA). After lyophilization, the product was obtained as a white solid. Yield: 72 mg.

MS: m/e=332 (M+H)$^+$

Example 3

3-[5-(4-Fluoro-phenyl)-thiophen-2-yl]-1-(piperidin-1-yl)-propenone

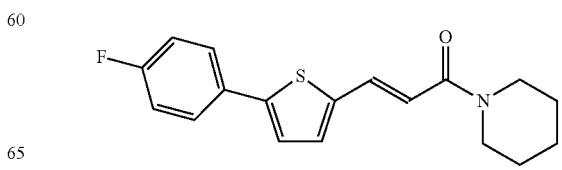

(a) 3-(5-Bromo-thiophen-2-yl)-1-(piperidin-1-yl)-propenone 50 g (2.1 mmol) of 3-(5-bromo-thiophen-2-yl)-acrylic acid, 2.47 g (21.5 mmol) of NEM and 774 mg (2.4 mmol) of TOTU were dissolved in 5 ml of DMF and stirred at room temperature for 15 min. 201 mg (0.5 mmol) of piperidine were added, and the reaction mixture was stirred at room temperature for 16 h. The solvent was removed under reduced pressure. The product was purified by silica gel chromatography.
Yield: 458 mg.
MS: m/e=300 (M)$^+$

(b) 3-[5-(4-Fluoro-phenyl)-thiophen-2-yl]-1-(piperidin-1-yl)-propenone 0.250 g (0.8 mmol) of 3-(5-bromo-thiophen-2-yl)-1-(piperidin-1-yl)-propenone and 48.1 mg (0.08 mmol) of tetrakis(triphenylphosphine)palladium were dissolved in 5 ml of degassed DME and stirred at room temperature for 10 min. 0.251 g (1.6 mmol) of 4-fluorophenylboronic acid and 1 ml of a 2 M aqueous sodium carbonate solution was added together with an additional 5 ml of degassed DME. The reaction mixture was heated to 95° C. for 4 h and then stirred at room temperature for 16 h. Solids were removed by filtration and the solution was evaporated to dryness. The residue was dissolved in ethyl acetate and washed three times with a saturated sodium hydrogencarbonate solution, and once with a saturated sodium chloride solution. The organic phase was dried with sodium sulfate, filtered and the solvent was removed under reduced pressure. The product was purified by preparative RP HPLC eluting with a gradient of 0 to 100% acetonitrile in water (+0.01% TFA). After lyophilization, the product was obtained as a white solid. Yield: 120 mg.
MS: m/e=316 (M+H)$^+$

Example 4

3-[5-(2-Fluoro-phenyl)-thiophen-2-yl]-1-(piperidin-1-yl)-propenone

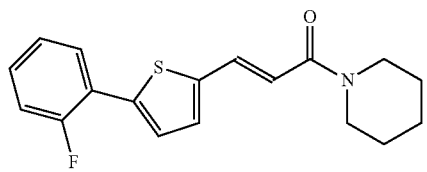

(a) 3-[5-(2-Fluoro-phenyl)-thiophen-2-yl]-acrylic Acid 9.38 g (40.2 mmol) of 3-(5-Bromo-thiophen-2-yl)-acrylic acid and 6.97 g (6 mmol) of tetrakis(triphenylphosphine)palladium were dissolved in 50 ml of degassed DME and stirred for 10 min at room temperature. 8.44 g (60.4 mmol) of 2-fluorophenylboronic acid and 50 ml of a 2 M aqueous sodium carbonate solution were added together with an additional 5 ml of degassed DME. The reaction mixture was heated to 95° C. for 4 h, and then stirred at room temperature for 16 h. The product precipitated partially from the reaction solution and was collected by filtration. This solid was boiled for 1 h in ethyl acetate and filtered while hot. The solvent was removed under reduced pressure. The remaining reaction solution was evaporated to dryness. The residue was taken up in ethyl acetate/water and filtered. The organic phase was dried with sodium sulfate, filtered and the solvent was removed under reduced pressure. The combined product was purified by silica gel chromatography. Yield: 7.5 g.
MS: m/e=249 (M+H)$^+$

(b) 3-[5-(2-Fluoro-phenyl)-thiophen-2-yl]-(1-piperidin-1-yl)-propenone

The compound was prepared analogously to Example 2(c) using 208 mg (0.8 mmol) of 3-[5-(2-fluoro-phenyl)-thiophen-2-yl]-acrylic acid. Yield: 65 mg.
MS: m/e=316 (M+H)$^+$

Example 5

3-(6-Phenoxy-pyridin-3-yl)-1-(piperidin-1-yl)-propenone Trifluoroacetic Acid Salt

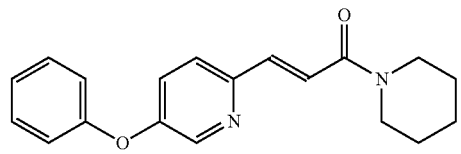

(a) 3-(6-Phenoxy-pyridin-3-yl)-acrylic Acid

The compound was prepared analogously to Example 2(a) using 5.0 g (25.1 mmol) of 6-phenoxy-pyridine-3-carbaldehyde. Yield: 5.66 g.
MS: m/e=242 (M+H)$^+$

(b) 3-(6-Phenoxy-pyridin-3-yl)-1-(piperidin-1-yl)-propenone Trifluoroacetic Acid Salt The compound was prepared analogously to Example 2(c) using 308 mg (1.3 mmol) of 3-(6-phenoxy-pyridin-3-yl)-acrylic acid. Yield: 169 mg.
MS: m/e=309 (M+H)$^+$

Example 6

4-[3-(6-Phenoxy-pyridin-3-yl)-acryloyl]-piperazin-2-one Trifluoroacetic Acid Salt

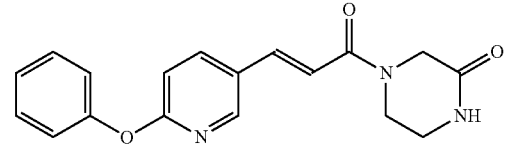

The compound was prepared analogously to Example 5(b) using 150 mg (0.62 mmol) of 3-(6-phenoxy-pyridin-3-yl)-acrylic acid and 54.2 mg (0.54 mmol) of piperazin-2-one.
Yield: 153 mg.
MS: m/e=324 (M+H)$^+$

Example 7

3-[5-(2-Fluoro-phenyl)-thiophen-2-yl]-1-(4-methyl-piperazin-1-yl)-propenone Trifluoroacetic Acid Salt

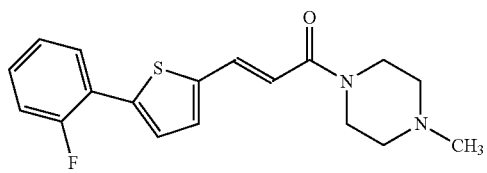

The compound was prepared analogously to Example 4(b) using 150 mg (0.6 mmol) of 3-[5-(2-fluoro-phenyl)-thiophen-2-yl]-acrylic acid and 50 mg (0.5 mmol) of 1-methylpiperazine. Yield: 152 mg.

MS: m/e=331 (M+H)⁺

Example 8

4-{3-[5-(2-Fluoro-phenyl)-thiophen-2-yl]-acryloyl}-piperazin-2-one

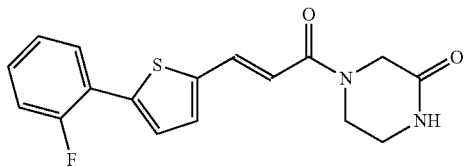

The compound was prepared analogously to Example 4(b) using 150 mg (0.6 mmol) of 3-[5-(2-fluoro-phenyl)-thiophen-2-yl]-acrylic acid and 54.2 mg (0.54 mmol) of piperazin-2-one. Yield: 109 mg.

MS: m/e=331 (M+H)⁺

Example 9

3-([2,2']Bithiophenyl-5-y)l-1-(piperidin-1-yl)-propenone

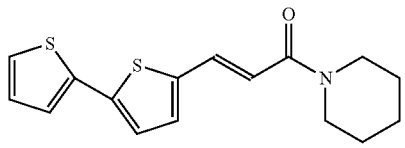

The compound was prepared analogously to Example 2(c) using 150 mg (0.63 mmol) of 3-([2,2']bithiophenyl-5-yl)-acrylic acid. Yield: 147 mg.

MS: m/e=304 (M+H)⁺

Example 10

1-(4-Methyl-piperazin-1-yl)-3-(6-phenoxy-pyridin-3-yl)-propenone Trifluoroacetic Acid Salt

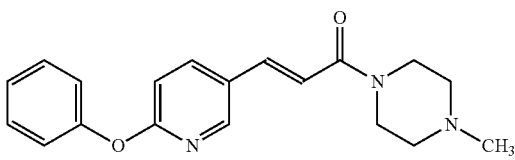

The compound was prepared analogously to Example 5(b) using 150 mg (0.62 mmol) of 3-(6-phenoxy-pyridin-3-yl)-acrylic acid and 50 mg (0.5 mmol) of 1-methylpiperazine. Yield: 162 mg.

MS: m/e=324 (M+H)⁺

Example 11

3-[5-(2-Methyl-5-trifluoromethyl-2H-pyrazol-3-yl)-thiophen-2-yl]-1-(piperidin-1-yl)-propenone

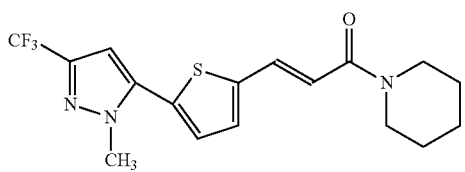

(a) 3-[5-(2-Methyl-5-trifluoromethyl-2H-pyrazol-3-yl)-thiophen-2-yl]-acrylic Acid The compound was prepared analogously to Example 2(a) using 2.32 g (9 mmol) of 5-(2-methyl-5-trifluoromethyl-2H-pyrazol-3-yl)-thiophene-2-carbaldehyde.

(b) 3-[5-(2-Methyl-5-trifluoromethyl-2H-pyrazol-3-yl)-thiophen-2-yl]-1-(piperidin-1-yl)-propenone The compound was prepared analogously to Example 2(c) using 100 mg (0.35 mmol) of 3-[5-(2-methyl-5-trifluoromethyl-2H-pyrazol-3-yl)-thiophen-2-yl]-acrylic acid. Yield: 27 mg.

MS: m/e=370 (M+H)⁺

Example 12

3-[5-(1-Methyl-5-trifluoromethyl-1H-pyrazol-3-yl)-thiophen-2-yl]-1-(piperidin-1-yl)-propenone

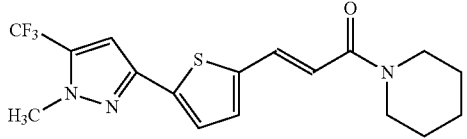

The compound was prepared analogously to Example 11 using 5-(1-methyl-5-trifluoromethyl-1H-pyrazol-3-yl)-thiophene-2-carbaldehyde. Yield: 22 mg.
MS: m/e=370 (M+H)$^+$

Example 13

1-(Piperidin-1-yl)-3-[5-(2-trifluoromethoxy-phenyl)-furan-2-yl]-propenone

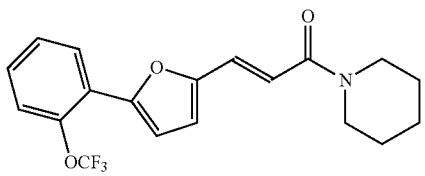

The compound was prepared analogously to Example 2(c) using 500 mg (1.7 mmol) of 3-[5-(2-trifluoromethoxy-phenyl)-furan-2-yl]-acrylic acid. Yield: 446 mg.
MS: m/e=366 (M+H)$^+$

Example 14

1-(Piperidin-1-yl)-3-[5-(2-trifluoromethyl-phenyl)-furan-2-yl]-propenone

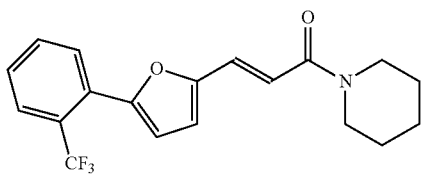

The compound was prepared analogously to Example 2(c) using 500 mg (1.8 mmol) of 3-[5-(2-trifluoromethyl-phenyl)-furan-2-yl]-acrylic acid. Yield: 474 mg.
MS: m/e=350 (M+H)$^+$

Example 15

3-[4-(2-Fluoro-phenyl)-thiophen-2-yl]-1-(piperidin-1-yl)-propenone

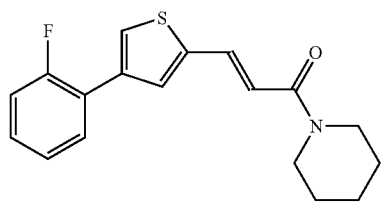

(a) 3-(4-Bromo-thiophen-2-yl)-1-(piperidin-1-yl)-propenone

The compound was prepared analogously to Example 3(a) using 142 mg (0.6 mmol) of 3-(4-bromo-thiophen-2-yl)-acrylic acid. Yield: 137 mg.
MS: m/e=301 (M+H)$^+$ (b) 3-[4-(2-Fluoro-phenyl)-thiophen-2-yl]-1-(piperidin-1-yl)-propenone The compound was prepared analogously to Example 3(b)) using 167 mg (0.6 mmol) of 3-(4-bromo-thiophen-2-yl)-1-(piperidin-1-yl)-propenone and 116 mg (0.8 mmol) of 2-fluorophenylboronic acid. Yield: 119 mg.
MS: m/e=316 (M+H)$^+$

Example 16

3-(6-Amino-5-phenyl-pyridin-2-yl)-1-(piperidin-1-yl)-propenone

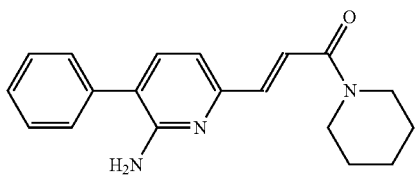

1.00 g (4 mmol) of 6-bromo-3-phenyl-2-pyridylamine were dissolved in 100 ml of acetonitrile and 0.22 (1 mmol) of palladium acetate, 0.61 mg of tri(ortho-tolyl)phosphine and 0.89 g (6.4 mmol) of 1-(piperidin-1-yl)-propenone were added and the mixture was refluxed in a sealed tube for 20 h. After evaporation to dryness the product was purified by column chromatography (silica gel, dichloromethane).
Yield: 95 mg.
MS: m/e=308 (M+H)$^+$

Example 17

3-(6-Chloro-benzo[b]thiophen-2-yl)-1-(piperidin-1-yl)-propenone

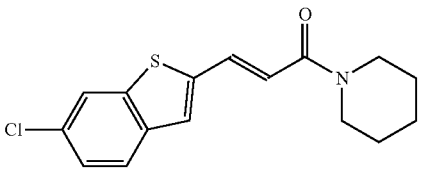

The compound was prepared analogously to Example 2(c) using 112 mg (0.6 mmol) of 3-(6-chloro-benzo[b]thiophen-2-yl)-acrylic acid. Yield: 0.1 mg.
MS: m/e=306 (M+H)$^+$

Example 18

3-[5-(4-Fluoro-phenyl)-pyridin-3-yl]-1-(piperidin-1-yl)-propenone

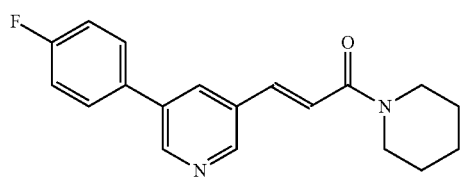

(a) 3-[5-(4-Fluoro-phenyl)-pyridin-3-yl]-acrylic Acid

The compound was prepared analogously to Example 2(a) using 5.0 g (24.9 mmol) of 5-(4-fluoro-phenyl)-pyridine-3-carbaldehyde. Yield: 4.53 g.
MS: m/e=244 (M+H)+

(b) 3-[5-(4-Fluoro-phenyl)-pyridin-3-yl]-1-(piperidin-1-yl)-propenone

The compound was prepared analogously to Example 2(c) using 250 mg (1 mmol) of 3-[5-(4-fluoro-phenyl)-pyridin-3-yl]-acrylic acid. Yield: 104 mg.
MS: m/e=311 (M+H)$^+$ Example 19

1-(Piperidin-1-yl)-3-(quinolin-4-yl)-propenone

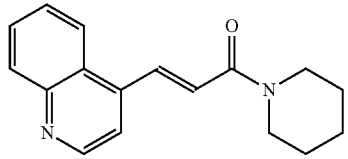

(a) 3-(Quinolin-4-yl)-acrylic Acid

The compound was prepared analogously to Example 2(a) using 10.0 g (63.6 mmol) of quinoline-4-carbaldehyde. Yield: 8.75 g.
MS: m/e=200 (M+H)$^+$ (b) 1-(Piperidin-1-yl)-3-(quinolin-4-yl)-propenone The compound was prepared analogously to Example 2(c) using 150 mg (0.75 mmol) of 3-(quinolin-4-yl)-acrylic acid. Yield: 154 mg.
MS: m/e=267 (M+H)$^+$ The 3-(quinolin-4-yl)-propenone derivatives of the formula Ib, which are listed in Table 1, were prepared analogously to Example 19.

TABLE 1

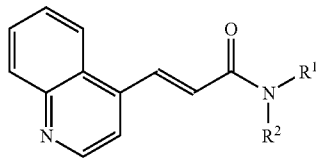

Example compounds of the formula Ib

| Example No. | $\begin{matrix} R^1 \\ | \\ N— \\ | \\ R^2 \end{matrix}$ | Yield | MS: m/e = |
|---|---|---|---|
| 20 | H$_3$C—N⟨⟩N— | 45.7 mg | 282 (M + H)$^+$ |

TABLE 1-continued

Ib

Example compounds of the formula Ib

| Example No. | $\begin{matrix} R^1 \\ | \\ N— \\ | \\ R^2 \end{matrix}$ | Yield | MS: m/e = |
|---|---|---|---|
| 21 | CH$_3$C(O)—N⟨⟩N— | 39.3 mg | 310 (M + H)$^+$ |
| 22 | O=⟨piperazinone⟩N— | 15.1 mg | 282 (M + H)$^+$ |
| 23 | cyclohexyl-NH-CH$_3$ | 10.3 mg | 281 (M + H)$^+$ |

Example 24

3-(4-Phenyl-thiophen-2-yl)-1-(piperidin-1-yl)-propenone

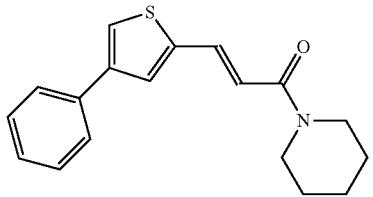

(a) 3-(4-Bromo-thiophen-2-yl)-acrylic Acid

The compound was prepared analogously to Example 2(a) using 25 g (130.9 mmol) of 4-bromo-thiophene-2-carbaldehyde. Yield: 21.2 g.
MS: m/e=234 (M+H)$^+$ (b) 3-(4-Bromo-thiophen-2-yl)-1-(piperidin-1-yl)-propenone 10 g (42.9 mmol) of 3-(4-bromo-thiophen-2-yl)-acrylic acid, 49.4 g (429 mmol) of NEM and 15.48 g (47.2 mmol) of TOTU were dissolved in 25 ml of DMF and stirred at room temperature for 15 min. 4.02 g (47.2 mmol) of piperidine were added, and the reaction mixture was stirred at room temperature for 16 h. The solvent was removed under reduced pressure. The residue was dissolved in ethyl acetate and the solution was washed three times with a saturated aqueous sodium hydrogencarbonate solution. The organic phase was dried with sodium sulfate, filtered and the solvent was removed under reduced pressure. The product was purified by silica gel chromatography eluting with dichloromethane. Yield: 10.87 g.

MS: m/e=301

(c) 3-(4-Phenyl-thiophen-2-yl)-1-(piperidin-1-yl)-propenone

The compound was prepared analogously to Example 3(b) using 150 mg (0.5 mmol) of 3-(4-bromo-thiophen-2-yl)-1-(piperidin-1-yl)-propenone and 0.091 g (0.7 mmol) of phenylboronic acid. Yield: 42.3 mg.

MS: m/e=298 (M+H)$^+$

Example 25

3-(4-Methyl-2-phenyl-pyrimidin-5-yl)-1-(piperidin-1-yl)-propenone

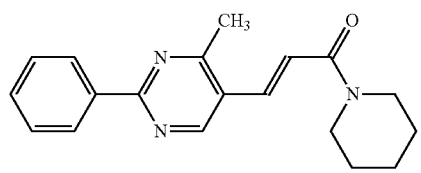

(a) 3-(4-Methyl-2-phenyl-pyrimidin-5-yl)-acrylic Acid

The compound was prepared analogously to Example 2(a) using 2.5 g (12.6 mmol) of 4-methyl-2-phenyl-pyrimidine-5-carbaldehyde. Yield: 2.4 g.

MS: m/e=241(M+H)$^+$ (b) 3-(4-Methyl-2-phenyl-pyrimidin-5-yl)-1-(piperidin-1-yl)-propenone The compound was prepared analogously to Example 2(c) using 100 mg (0.42 mmol) of 3-(4-methyl-2-phenyl-pyrimidin-5-yl)-acrylic acid. Yield: 100 mg.

MS: m/e=308 (M+H)+

Example 26

N-Cyclohexyl-3-(6-phenoxy-pyridin-3-yl)-acrylamide Trifluoroacetic Acid Salt

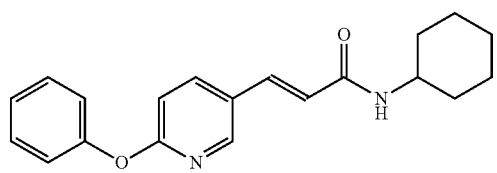

The compound was prepared analogously to Example 5(b) using 100 mg (0.41 mmol) of 3-(6-phenoxy-pyridin-3-yl)-acrylic acid. Yield: 85 mg.

MS: m/e=323 (M+H)$^+$

Example 27

3-(6-Phenoxy-pyridin-3-yl)-N-phenyl-acrylamide Trifluoroacetic Acid Salt

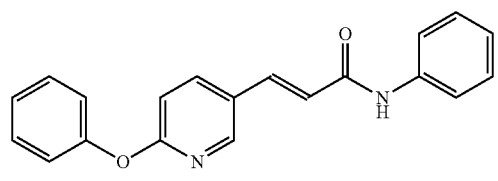

The compound was prepared analogously to Example 5(b) using 100 mg (0.41 mmol) of 3-(6-phenoxy-pyridin-3-yl)-acrylic acid. Yield: 82 mg.

MS: m/e=317 (M+H)$^+$

Example 28

General procedure 1

Preparation of N-substituted 3-[6-(2-fluoro-phenyl)-pyridin-3-yl]-acrylamides of the Formula Ic

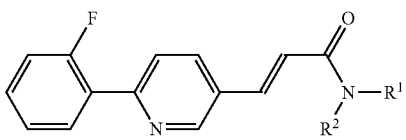

Ic

3-[6-(2-Fluoro-phenyl)-pyridin-3-yl]-acryloyl chloride hydrochloride salt was prepared in quantitative yield by boiling 3-[6-(2-fluoro-phenyl)-pyridin-3-yl]-acrylic acid in thionyl chloride, followed by removal of the volatiles by coevaporating three times with toluene. 3-[6-(2-Fluoro-phenyl)-pyridin-3-yl]-acryloyl chloride hydrochloride salt was dissolved in pyridine, and 1 equivalent of the respective amine was added. The reaction mixture was stirred at room temperature for 2 h. The solvent was removed under reduced pressure, and residual pyridine was removed by coevaporating three times with toluene. The residue was dissolved in DMF, and the product was purified by preparative RP HPLC eluting with a gradient of 0 to 100% acetonitrile in water (+0.01% TFA). After lyophilization, the product was obtained as a solid.

According to general procedure 1, the example compounds listed in Table 2 were prepared which may be named as N-substituted 3-[6-(2-fluoro-phenyl)-pyridin-3-yl]-acrylamides, for example as 3-[6-(2-fluoro-phenyl)-pyridin-3-yl]-N-(2-trifluoromethyl-phenyl)-acrylamide in the case of Example 29, or as 1-substituted 3-[6-(2-fluoro-phenyl)-pyridin-3-yl]-propenones, for example as 3-[6-(2-fluoro-phenyl)-pyridin-3-yl]-1-(pyrrolidin-1-yl)-propenone in the case of Example 51, or in another manner, for example as 1-{3-[6-(2-fluoro-phenyl]-pyridin-3-yl}-acryloyl-pyrrolidine-2-carboxylic acid methyl ester in the case of Example 57, depending on the structure of the individual compound.

TABLE 2

Example compounds of the formula Ic

R¹–N(–)–R²

| Example No. | R¹/R² structure | MS: m/e = |
|---|---|---|
| 29 | 2-CF₃-C₆H₄-NH- | 387 (M + H)⁺ |
| 30 | 2,4-diCl-C₆H₃-NH- | 387 (M + H)⁺ |
| 31 (a) | piperidin-1-yl | 311 (M + H)⁺ |
| 32 (a) | 2-F-C₆H₄-NH- | 337 (M + H)⁺ |
| 33 (a) | 2-CN-C₆H₄-NH- | 344 (M + H)⁺ |
| 34 (a) | 2-Cl-C₆H₄-NH- | 353 (M + H)⁺ |
| 35 (a) | 2,3-diCl-C₆H₃-NH- | 387 (M + H)⁺ |
| 36 (a) | 2,3-diF-C₆H₃-NH- | 355 (M + H)⁺ |
| 37 (a) | 4-Cl-C₆H₄-NH- | 353 (M + H)⁺ |
| 38 (a) | 4-F-C₆H₄-NH- | 337 (M + H)⁺ |
| 39 (a) | 2,4-diF-C₆H₃-NH- | 355 (M + H)⁺ |
| 40 (a) | 4-CF₃-C₆H₄-NH- | 387 (M + H)⁺ |
| 41 (a) | 6-CF₃-pyridin-3-yl-NH- | 388 (M + H)⁺ |
| 42 (a) | 2-methyl-6-CF₃-pyridin-3-yl-NH- | 402 (M + H)⁺ |
| 43 (a) | 6-CH₃O-pyridin-3-yl-NH- | 350 (M + H)⁺ |
| 44 (a) | pyridin-2-yl-NH- | 320 (M + H)⁺ |
| 45 (a) | pyridin-3-yl-NH- | 320 (M + H)⁺ |
| 46 (a) | 2,2-difluoro-benzo[1,3]dioxol-4-yl-NH- | 399 (M + H)⁺ |
| 47 (a) | C₆H₅-N(CH₃)- | 333 (M + H)⁺ |
| 48 (a) | C₆H₅-N(CH₂CH₃)- | 347 (M + H)⁺ |
| 49 (a) | thiazol-2-yl-NH- | 326 (M + H)⁺ |
| 50 (a) | azetidin-1-yl | 283 (M + H)⁺ |
| 51 (a) | pyrrolidin-1-yl | 297 (M + H)⁺ |
| 52 (a) | azepan-1-yl | 325 (M + H)⁺ |

TABLE 2-continued

Example compounds of the formula Ic

| Example No. | R¹, R² structure | MS: m/e = |
|---|---|---|
| 53 (a) | morpholine-N- | 313 (M + H)⁺ |
| 54 (a) | 2,6-dimethylmorpholine-N- | 341 (M + H)⁺ |
| 55 (a) | morpholine-N-NH- | 328 (M + H)⁺ |
| 56 (a) | 1,4-oxazepane-N- | 327 (M + H)⁺ |
| 57 (a) | 1-methylpyrrolidine-2-carboxylic acid methyl ester | 355 (M + H)⁺ |
| 58 (a) | thiazolidine-N- | 315 (M + H)⁺ |
| 59 (a) | diisopropyl-N(CH₃)- | 327 (M + H)⁺ |
| 60 (a) | diethyl-N- | 299 (M + H)⁺ |
| 61 (a) | bis(2-methoxyethyl)-N- | 359 (M + H)⁺ |
| 62 (a) | CH₃-O-CH₂CH₂-N(CH₃)- | 315 (M + H)⁺ |
| 63 (a) | dimethyl-N- | 271 (M + H)⁺ |
| 64 (a) | cyclopropylmethyl-NH- | 297 (M + H)⁺ |
| 65 (a) | isobutyl-NH- | 299 (M + H)⁺ |
| 66 (a) | cyclohexyl-NH- | 325 (M + H)⁺ |
| 67 (a) | adamantyl-NH- | 377 (M + H)⁺ |
| 68 (a) | benzyl-NH- | 333 (M + H)⁺ |
| 69 (a) | 1-phenylethyl-NH- | 347 (M + H)⁺ |
| 70 (a) | benzyl-N(CH₃)- | 347 (M + H)⁺ |
| 71 (a) | pyridin-2-ylmethyl-NH- | 334 (M + H)⁺ |
| 72 (a) | 2-fluorobenzyl-NH- | 351 (M + H)⁺ |
| 73 (a) | 2,6-difluorobenzyl-NH- | 369 (M + H)⁺ |
| 74 (a) | thiophen-2-ylmethyl-NH- | 339 (M + H)⁺ |
| 75 (a) | phenyl-NH- | 319 (M + H)⁺ |

(a) trifluoroacetic acid salt

Example 76

3-[6-(4-Fluoro-phenoxy)-pyridin-3-yl]-1-(piperidin-1-yl)-propenone Trifluoroacetic Acid Salt

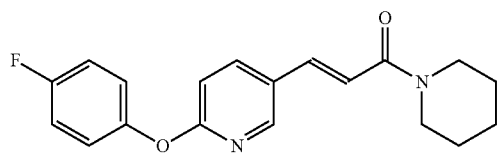

193 mg (1.72 mmol) of 4-fluorophenol were added to 43 mg (1.72 mmol) of sodium hydride in 3 ml dry DMF. After stirring the mixture at room temperature for 1 h, 378 mg (1.56 mmol) of 3-(6-bromo-pyridin-3-yl)-acrylic acid ethyl ester were added and the mixture was heated to 120° C. for 2 h. The solution was poured onto ice and extracted with ethyl acetate. The combined organic phases were dried with sodium sulfate and evaporated to dryness. The resulting 3-[6-(4-fluoro-phenoxy)-pyridin-3-yl]-acrylic acid ethyl ester was hydrolyzed using 168 mg (7.2 mmol) of lithium hydroxide in 1 ml of THF and 9 ml of water. The mixture was extracted with ethyl acetate, acidified to pH=4 with 1 N hydrochloric acid, and the precipitating 3-[6-(4-fluoro-phenoxy)-pyridin-3-yl]-acrylic acid was collected by suction and dried. 100 mg (0.38 mmol) of the acid were dissolved in 5 ml of THF and treated with 128 mg (0.39 mmol) of TOTU and 93 mg (0.72 mmol) ethyldiisopropylamine. After stirring the mixture for 1 h at room temperature, 28 mg (0.33 mmol) of piperidine were added and the reaction mixture was stirred for further 10 h. The mixture was poured onto a saturated sodium hydrogencarbonate solution and extracted with ethyl acetate. The combined organic phases were dried and evaporated to dryness. The raw material was purified by HPLC(RP18, acetonitrile/water, 0.1% TFA). Yield: 55 mg.

MS: m/e=327 (M+H)+

Example 77

3-[6-(2-Chloro-phenoxy)-pyridin-3-yl]-1-(piperidin-1-yl)-propenone Trifluoroacetic Acid Salt

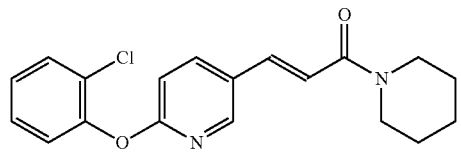

The compound was prepared according to the procedure described in Example 76, using 2-chlorophenol in stead of 4-fluorophenol.

MS: m/e=343 (M+H)+

Example 78

3-[6-(4-Fluoro-benzyloxy)-pyridin-3-yl]-1-(piperidin-1-yl)-propenone Trifluoroacetic Acid Salt

The compound was prepared according to the procedure described in Example 76, using 4-fluorophenylmethanol instead of 4-fluorophenol.

MS: m/e=341 (M+H)+

Example 79

3-[6-(2-Fluoro-phenyl)-pyridin-2-yl]-1-(piperidin-1-yl)-propenone Trifluoroacetic Acid Salt

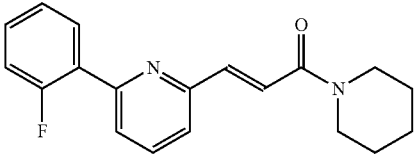

(a) 3-(6-Bromo-pyridin-2-yl)-acrylic Acid 10 g (53.8 mmol) of 6-bromo-pyridine-2-carbaldehyde were dissolved in 70 ml of pyridine and 6.73 g (64.5 mmol) of malonic acid and 457 mg (5.4 mmol) of piperidine were added. The reaction mixture was boiled under reflux for 6 h. The solution was cooled to room temperature and then poured onto ice. Concentrated hydrochloric acid was added until pH=5, whereupon the product precipitated. The product was isolated by filtration and dried under reduced pressure. Yield: 9.85 g.

MS: m/e=227

(b) 3-(6-Bromo-pyridin-2-yl)-1-(piperidin-1-yl)-propenone 3 g (13.2 mmol) of 3-(6-bromo-pyridin-2-yl)-acrylic acid, 15.1 g (131 mmol) of NEM and 4.75 g (14.5 mmol) of TOTU were dissolved in 15 ml of DMF and stirred at room temperature for 20 min. 1.23 g (14.5 mmol) of piperidine were added, and the reaction mixture was stirred at room temperature for 16 h. The solvent was removed under reduced pressure. The residue was dissolved in ethyl acetate and the solution was washed three times with a saturated aqueous sodium hydrogencarbonate solution. The organic phase was dried with sodium sulfate, filtered, and the solvent was removed under reduced pressure. Yield: 3.0 g.

MS: m/e=294

(c) 3-[6-(2-Fluoro-phenyl)-pyridin-2-yl]-1-(piperidin-1-yl)-propenone Trifluoroacetic Acid Salt 150 mg (0.51 mmol) of 3-(6-bromo-pyridin-2-yl)-1-(piperidin-1-yl)-propenone and 87.7 mg (0.076 mmol) of tetrakis(triphenylphosphine)palladium were dissolved in 50 ml of degassed DME and stirred for 10 min at room temperature. 107 mg (0.76 mmol) of 2-fluorophenylboronic acid and 1 ml of a 2 M aqueous sodium carbonate solution were added. The reaction mixture was heated to 105° C. for 4 h and then stirred at room temperature for 16 h. The mixture was applied to a silica cartridge and eluted with dichloromethane. The solvent was removed under reduced pressure. The product was purified by preparative RP HPLC eluting with a gradient of 0 to 100% acetonitrile in water (+0.01% TFA). After lyophilization, the product was obtained as a solid.

Yield: 60.8 mg.

MS: m/e=311 (M+H)$^+$

Example 80

3-[6-(4-Fluoro-phenyl)-pyridin-2-yl]-1-(piperidin-1-yl)-propenone Trifluoroacetic Acid Salt

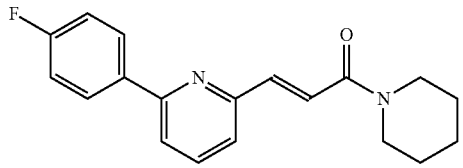

The compound was prepared analogously to Example 79(c) using 108 mg (0.76 mmol) of 4-fluorophenylboronic acid. Yield: 70.7 mg.

MS: m/e=311 (M+H)$^+$

Example 81

3-[6-Phenyl-pyridin-2-yl]-1-(piperidin-1-yl)-propenone Trifluoroacetic Acid Salt

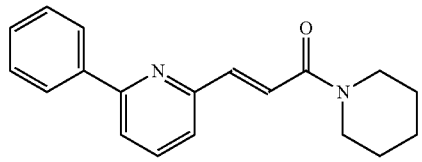

The compound was prepared analogously to Example 79(c) using 92.9 mg (0.76 mmol) of phenylboronic acid. Yield: 13.9 mg.

MS: m/e=293 (M+H)$^+$

Example 82

3-[6-(Benzo[b]thiophen-2-yl)-pyridin-2-yl]-1-(piperidin-1-yl)-propenone Trifluoroacetic Acid Salt

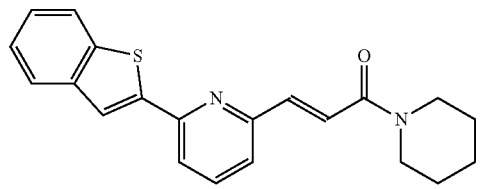

The compound was prepared analogously to Example 79(c) using 136 mg (0.76 mmol) of benzo[b]thiophene-2-boronic acid. Yield: 65.4 mg.

MS: m/e=349 (M+H)$^+$

Examples 83

N-(2,2-Dimethyl-propyl)-3-[6-(2-fluoro-phenyl)-pyridin-3-yl]-acrylamide Trifluoroacetic Acid Salt

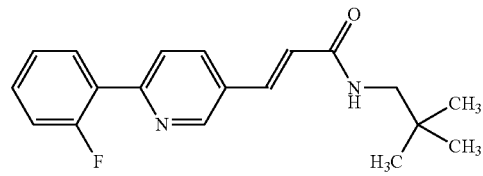

The compound was prepared analogously to Example 2(c) using 75 mg (0.31 mmol) of 3-[6-(2-fluoro-phenyl)-pyridin-3-yl]-acrylic acid. Yield: 49 mg.

MS: m/e=313 (M+H)$^+$

Example 84

N-Cyclohexylmethyl-3-[6-(2-fluoro-phenyl)-pyridin-3-yl]-acrylamide Trifluoroacetic Acid Salt

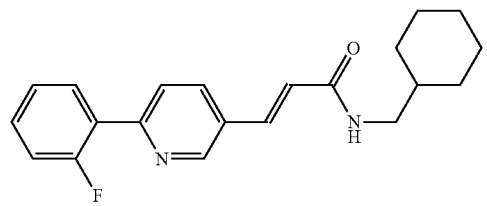

The compound was prepared analogously to Example 2(c) using 75 mg (0.31 mmol) of 3-[6-(2-fluoro-phenyl)-pyridin-3-yl]-acrylic acid. Yield: 76 mg.

MS: m/e=339 (M+H)$^+$

The N-substituted 3-[5-(4-fluoro-phenyl)-pyridin-3-yl]-acrylamides of the formula Id, which are listed in Table 3, were prepared analogously to Example 18(b) using 75 mg (0.31 mmol) of 3-[5-(4-fluoro-phenyl)-pyridin-3-yl]-acrylic acid.

TABLE 3

Example compounds of the formula Id (Structure: 4-fluorophenyl-pyridine with acrylamide -C(O)-N(R¹)(R²))

| Example No. | R¹/R² (amine) | Yield | MS: m/e = |
|---|---|---|---|
| 85 (a) | cyclohexylmethyl-NH- | 64 mg | 339 (M + H)⁺ |
| 86 (a) | phenyl-NH- | 52.5 mg | 319 (M + H)⁺ |
| 87 (a) | isobutyl-NH- (H₃C-CH(CH₃)-CH₂-NH-) | 61.5 mg | 299 (M + H)⁺ |
| 88 (a) | diethyl-N- ((H₃C-CH₂-)₂N-) | 52.5 mg | 299 (M + H)⁺ |
| 89 (a) | thiazol-2-yl-NH- | 30.7 mg | 326 (M + H)⁺ |
| 90 (a) | benzyl-NH- | 50.5 mg | 333 (M + H)⁺ |
| 91 (a) | cyclohexyl-NH- | 48.5 mg | 325 (M + H)⁺ |
| 92 (a) | neopentyl-NH- ((CH₃)₃C-CH₂-NH-) | 49 mg | 313 (M + H)⁺ |

(a) trifluoroacetic acid salt

TABLE 4

Example compounds of the formula Ie (Structure: 4-methyl-2-phenyl-pyrimidin-5-yl acrylamide -C(O)-N(R¹)(R²))

| Example No. | R¹/R² (amine) | Yield | MS: m/e = |
|---|---|---|---|
| 93 | benzyl-NH- | 51 mg | 330 (M + H)⁺ |
| 94 | phenyl-NH- | 18 mg | 316 (M + H)⁺ |
| 95 | cyclohexylmethyl-NH- | 33.8 mg | 336 (M + H)⁺ |
| 96 (a) | pyridin-3-yl-NH- | 37.9 mg | 317 (M + H)⁺ |
| 97 | isobutyl-NH- (H₃C-CH(CH₃)-CH₂-NH-) | 46 mg | 296 (M + H)⁺ |
| 98 | cyclohexyl-NH- | 46 mg | 322 (M + H)⁺ |
| 99 (a) | pyridin-2-yl-NH- | 14 mg | 317 (M + H)⁺ |
| 100 | neopentyl-NH- ((CH₃)₃C-CH₂-NH-) | 41.5 mg | 310 (M + H)⁺ |
| 101 | diethyl-N- ((H₃C-CH₂-)₂N-) | 39 mg | 296 (M + H)⁺ |

(a) trifluoroacetic acid salt

The N-substituted 3-(4-methyl-2-phenyl-pyrimidin-5-yl)-acrylamides of the formula Ie, which are listed in Table 4, were prepared analogously to Example 25(b) using 75 mg (0.31 mmol) of 3-(4-methyl-2-phenyl-pyrimidin-5-yl)-acrylic acid.

The N-substituted 3-(6-phenoxy-pyridin-3-yl)-acrylamides of the formula If, which are listed in Table 5, were prepared analogously to Example 5(b) using 75 mg (0.31 mmol) of 3-(6-phenoxy-pyridin-3-yl)-acrylic acid.

TABLE 5

Example compounds of the formula If

| Example No. | R² | Yield | MS: m/e = |
|---|---|---|---|
| 102 (a) | benzyl | 42 mg | 331 (M + H)⁺ |
| 103 (a) | N-methylbenzyl | 51 mg | 345 (M + H)⁺ |
| 104 (a) | cyclohexylmethyl | 53.9 mg | 337 (M + H)⁺ |
| 105 (a) | pyridin-3-yl | 35.6 mg | 318 (M + H)⁺ |
| 106 (a) | isobutyl | 29 mg | 297 (M + H)⁺ |
| 107 (a) | neopentyl | 41 mg | 311 (M + H)⁺ |
| 108 (a) | diethyl-like | 24 mg | 297 (M + H)⁺ |
| 109 (a) | pyridin-2-yl | 2.1 mg | 318 (M + H)⁺ |

(a) trifluoroacetic acid salt

Example 110

3-[6-(2-Fluoro-phenyl)-pyridin-3-yl]-but-2-enoic Acid Dimethylamide Trifluoroacetic Acid Salt

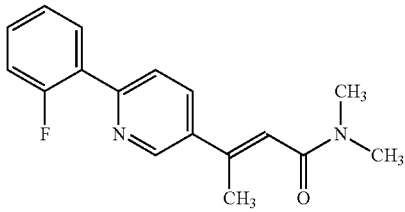

5 ml of dimethylsulfoxide were added slowly to a mixture of 0.928 g (4.22 mmol) of trimethylsulfoxonium iodide and 96 mg (4.03 mmol) of sodium hydride. The mixture was stirred at room temperature for 15 min, and then 850 mg (3.15 mmol) of 3-[6-(2-fluoro-phenyl)-pyridin-3-yl]-N,N-dimethyl-acrylamide were added. The reaction mixture was stirred at room temperature for 18 h, filtered, and the product was purified by preparative RP HPLC eluting with a gradient of 0 to 100% acetonitrile in water (+0.01% TFA). After lyophilization, the product was obtained as a solid. Yield: 150 mg.

MS: m/e=285 (M+H)⁺

Example 111

3-[4-(Benzo[b]thiophen-2-yl)-thiophen-2-yl]-1-(piperidin-1-yl)-propenone

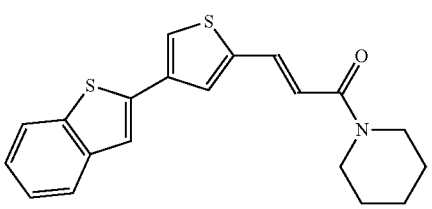

The compound was prepared analogously to Example 24(c) using 126 mg (0.42 mmol) of 3-(4-bromo-thiophen-2-yl)-1-(piperidin-1-yl)-propenone. Yield: 32 mg.

MS: m/e=354 (M+H)⁺

Example 112

3-(4-Methyl-2-phenyl-thiazol-5-yl)-1-(piperidin-1-yl)-propenone

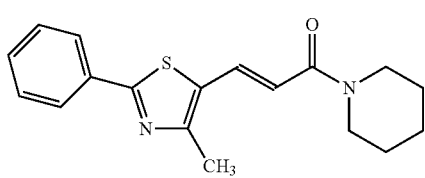

(a) 3-(4-Methyl-2-phenyl-thiazol-5-yl)-acrylic Acid

A mixture of 300 mg (1.47 mmol) of 4-methyl-2-phenyl-thiazole-5-carbaldehyde, 169 mg (1.62 mmol) of malonic acid and 880 mg (10.33 mmol) of piperidine in 10 ml of pyridine was stirred at 90° C. for 5 h and at 100° C. for 6 h. After concentration, the residue was treated with a sodium hydrogencarbonate solution and ethyl acetate. The aqueous phase was separated and acidified. The precipitated product was filtered off with suction and dried. Yield: 260 mg.

(b) 3-(4-Methyl-2-phenyl-thiazol-5-yl)-1-(piperidin-1-yl)-propenone 80 mg (0.326 mmol) of 3-(4-methyl-2-phenyl-thiazol-5-yl)-acrylic acid and 66 mg (0.652 mmol) of triethylamine were dissolved in 5 ml of DMF. 124 mg (0.326 mmol) of HATU were added, the mixture was stirred at room temperature for 15 min, 55.5 mg (0.6523 mmol) of piperidine were added, and the mixture was stirred at room temperature for 2 h. After concentration, the residue was treated with a sodium hydrogencarbonate solution and ethyl acetate, the organic phase was separated and evaporated. Yield: 68 mg.

MS: m/e=313 (M+H)+

Example 113

3-[6-(4-Fluoro-phenyl)-pyridin-3-yl]-N-phenyl-acrylamide, Trifluoroacetic Acid Salt

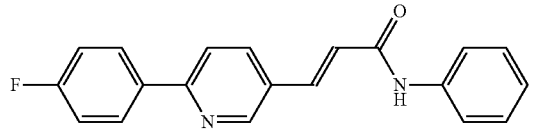

100 mg (0.41 mmol) of 3-[6-(4-fluoro-phenyl)-pyridin-3-yl]-acrylic acid and 195 mg of thionyl chloride were stirred at room temperature for 2 h. After concentration, 5 ml of pyridine and 38 mg (0.411 mmol) of aniline were added. The reaction mixture was stirred at room temperature for 5 h and then concentrated. The residue was purified by preparative HPLC(RP18, acetonitrile/water+0.1% TFA). Yield: 5 mg.

MS: m/e=319 (M+H)+

Example 114

N-(2-Fluoro-phenyl)-3-[6-(4-fluoro-phenyl)-pyridin-3-yl]-acrylamide, Trifluoroacetic Acid Salt

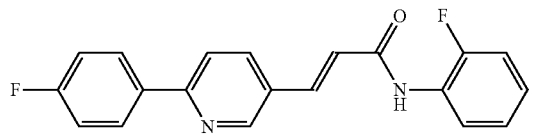

The compound was prepared analogously to Example 113 using 45.7 mg (0.411 mmol) of 2-fluoroaniline instead of aniline. Yield: 6 mg.

MS: m/e=337 (M+H)+

Example 115

3-[6-(4-Fluoro-phenyl)-pyridin-3-yl]-N-(thiazol-2-yl)-acrylamide, Trifluoroacetic Acid Salt

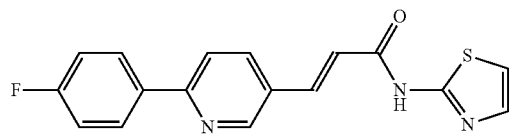

The compound was prepared analogously to Example 113 using 41.2 mg (0.411 mmol) of 2-aminothiazole instead of aniline. Yield: 3 mg.

MS: m/e=326 (M+H)+

Example 116

3-[4-(4-Fluoro-phenyl)-thiazol-2-yl]-N-(pyridin-2-yl)-acrylamide

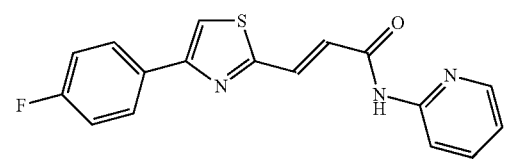

(a) 4-(4-Fluoro-phenyl)-thiazole-2-carbaldehyde 5 g (23.04 mmol) of 4-fluorophenacyl bromide and 3.76 g (23.04 mmol) of 2,2-diethoxythioacetamide in 100 ml of ethanol were stirred at room temperature for 2 h. After concentration, the residue was treated with ethyl acetate and filtered. The filtrate was concentrated and the obtained residue, which consisted of the diethyl acetal of 4-(4-fluoro-phenyl)-thiazole-2-carbaldehyde, was treated with 100 ml of acetone/water and 1 ml of 2 N hydrochloric acid. After stirring at room temperature for 2 h, the reaction mixture was evaporated. Yield: 4.22 g.

(b) 3-[4-(4-Fluoro-phenyl)-thiazol-2-yl]-acrylic Acid Tert-butyl Ester 2 g (10.57 mmol) of 4-(4-fluoro-phenyl)-thiazole-2-carbaldehyde and 4.177 g (11.09 mmol) of (tert-butoxycarbonylmethylene)triphenylphosphorane in 25 ml of THF were stirred at room temperature for 2 h. The reaction mixture was evaporated, and the residue was used in the subsequent step without purification.

(c) 3-[4-(4-Fluoro-phenyl)-thiazol-2-yl]-acrylic Acid

The crude product obtained in step (b) was stirred with 10 ml of 90% trifluoroacetic acid at room temperature for 1 h. After concentration, the residue was dissolved in a dilute sodium hydroxide solution and extracted with ethyl acetate. The aqueous phase was acidified with hydrochloric acid, and the precipitated product was filtered off with suction and dried. Yield: 1.52 g.

(d) 3-[4-(4-Fluoro-phenyl)-thiazol-2-yl]-N-(pyridin-2-yl)-acrylamide 100 mg (0.4 mmol) of 3-[4-(4-fluoro-phenyl)-thiazol-2-yl]-acrylic acid, 75.72 mg (0.8 mmol) of 2-aminopyridine, 121.8 mg (1.2 mmol) of triethylamine and 152.6 mg (0.4 mmol) of HATU in 5 ml of DMF were stirred at room temperature for 2 h. The reaction mixture was concentrated, and water and ethyl acetate were added. The organic phase was separated, washed and concentrated. The residue was purified by chromatography (RP18). Yield: 35.5 mg.

MS: m/e=326 (M+H)+

The N-substituted 3-[4-(4-fluoro-phenyl)-thiazol-2-yl]-acrylamides of the formula Ig, which are listed in Table 6, were prepared analogously to Example 116(d) using 100 mg (0.4 mmol) of 3-[4-(4-fluoro-phenyl)-thiazol-2-yl]-acrylic acid.

TABLE 6

Ig

Example compounds of the formula Ig

| Example No. | R1/R2 | Yield | MS: m/e = |
|---|---|---|---|
| 117 (a) | H3C–N–  H3C | 67.1 mg | 277 (M + H)+ |
| 118 | pyridin-3-yl–NH– | 77 mg | 326 (M + H)+ |
| 119 | piperidin-1-yl | 39 mg | 317 (M + H)+ |
| 120 | thiazol-2-yl–NH– | 84 mg | 332 (M + H)+ |
| 121 | 2-F-phenyl–NH– | 28 mg | 343 (M + H)+ |
| 122 | phenyl–NH– | 41 mg | 325 (M + H)+ |

(a) Dimethylamine was employed in the form of its hydrochloride, and an additional amount of 0.8 mmol of triethylamine was added.

Example 123

3-[4-(2-Fluoro-phenyl)-thiophen-2-yl]-1-(piperidin-1-yl)-but-2-en-1-one

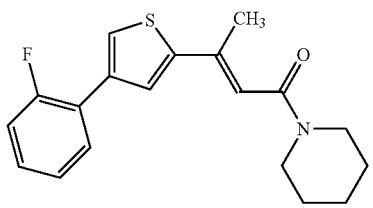

5 ml of dimethylsulfoxide were added slowly to a mixture of 0.907 g (4.12 mmol) of trimethylsulfoxonium iodide and 98.9 mg (4.12 mmol) of sodium hydride. The mixture was stirred at room temperature for 15 min, 500 mg (1.59 mmol) of 3-[4-(2-fluoro-phenyl)-thiophen-2-yl]-1-(piperidin-1-yl)-propenone was added, and the reaction mixture was stirred at room temperature for 18 h. Then a freshly prepared solution of a further 1 equivalent of trimethylsulfoxonium iodide/sodium hydride in dimethylsulfoxide was added. The reaction mixture was stirred at room temperature for 16 h, filtered, and the product was purified by preparative RP HPLC eluting with a gradient of 0 to 100% acetonitrile in water (+0.01% TFA). After lyophilization, the product was obtained as a solid. Yield: 80 mg.

MS: m/e=330 (M+H)+

Example 124

3-(6-Phenoxy-pyridin-3-yl)-acrylamide

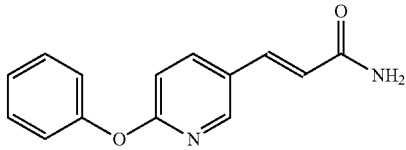

100 mg (0.415 mmol) of 3-(6-phenoxy-pyridin-3-yl)-acrylic acid was dissolved in 4 ml of DMF, and 52 mg (0.415 mmol) of N,N'-diisopropylcarbodiimide and 126 mg (0.830 mmol) of the ammonium salt of benzotriazol-1-ol were added. After 1 h a further 126 mg (0.830 mmol) of the ammonium salt of benzotriazol-1-ol were added. The reaction was stirred at room temperature for 16 h, filtered, and the product was purified by preparative RP HPLC eluting with a gradient of 0 to 100% acetonitrile in water (+0.01% TFA). After lyophilization, the product was obtained as a solid. Yield: 75 mg.

MS: m/e=241 (M+H)+

Example 125

3-(6-(Benzo[b]thiophen-2-yl)-pyridin-3-yl)-1-(piperidin-1-yl)-propenone

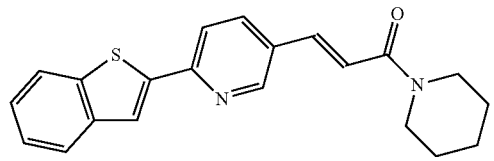

69

(a) 3-(6-Bromo-pyridin-3-yl)-acrylic Acid 750 mg (3.1 mmol) of 3-(6-bromo-pyridin-3-yl)-acrylic acid methyl ester was dissolved in 30 ml of dioxane and 4.65 ml of a 2 N aqueous sodium hydroxide solution was added. The reaction mixture was stirred at room temperature for 2 h. The reaction solution was poured into water and acidified with concentrated hydrochloric acid, whereupon the product precipitated. The product was isolated by filtration and dried under reduced pressure. Yield: 673 mg.

MS: m/e=228 (M+H)$^+$

(b) 3-(6-Bromo-pyridin-3-yl)-1-(piperidin-1-yl)-propenone

The compound was prepared analogously to Example 79(b) using 672 mg (2.95 mmol) of 3-(6-bromo-pyridin-3-yl)-acrylic acid. Yield: 660 mg.

MS: m/e=295 (M+H)$^+$

(c) 3-(6-(Benzo[b]thiophen-2-yl)-pyridin-3-yl)-1-(piperidin-1-yl)-propenone

The compound was prepared analogously to Example 79(c) using 110 mg (0.37 mmol) of 3-(6-bromo-pyridin-3-yl)-1-(piperidin-1-yl)-propenone. Yield: 84 mg.

MS: m/e=349 (M+H)$^+$

The 3-(6-substituted pyridin-3-yl)-1-(piperidin-1-yl)-propenones of the formula Ih, which are listed in Table 7, were prepared analogously to Example 79(c) using 110 mg (0.37 mmol) of 3-(6-bromo-pyridin-3-yl)-1-(piperidin-1-yl)-propenone.

TABLE 7

Ih

Example compounds of the formula Ih

| Example No. | R$^3$—X— | Yield | MS: m/e = |
|---|---|---|---|
| 126 (a) | 2,3-difluoro-phenyl | 48.5 mg | 329 (M + H)$^+$ |
| 127 (a) | 2,4-difluoro-3-methyl-phenyl | 60.6 mg | 329 (M + H)$^+$ |
| 128 | 3-fluoro-phenyl | 55 mg | 311 (M + H)$^+$ |
| 129 | 4-fluoro-phenyl | 85 mg | 311 (M + H)$^+$ |

TABLE 7-continued

Ih

Example compounds of the formula Ih

| Example No. | R$^3$—X— | Yield | MS: m/e = |
|---|---|---|---|
| 130 | phenyl | 74 mg | 293 (M + H)$^+$ |

(a) trifluoroacetic acid salt

Example 131

3-(1-Oxy-6-phenoxy-pyridin-3-yl)-1-(piperidin-1-yl)-propenone

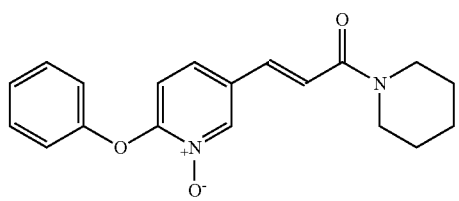

100 mg (0.324 mmol) of 3-(6-phenoxy-pyridin-3-yl)-1-(piperidin-1-yl)-propenone were dissolved in 10 ml dichloromethane and 80 mg (0.324 mmol) of 70% 3-chloroperbenzoic acid was added. The reaction mixture was stirred at room temperature for 16 h, and then a further 40 mg (0.162 mmol) of 70% 3-chloroperbenzoic acid was added and the reaction mixture was stirred at room temperature for another 16 h. The solvent was removed under a stream of argon. The residue was dissolved in DMF and the product was purified by preparative RP HPLC eluting with a gradient of 0 to 100% acetonitrile in water (+0.01% TFA). After lyophilization, the product was obtained as a solid. Yield: 24.2 mg.

MS: m/e=325 (M+H)$^+$

Example 132

3-[2-(4-Fluoro-phenyl)-pyrimidin-5-yl]-N-(thiazol-2-yl)-acrylamide

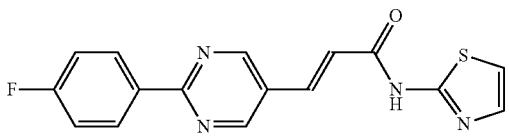

(a) 2-(4-Fluoro-phenyl)-pyrimidine-5-carbaldehyde 2 g (11.45 mmol) of 4-fluorobenzamidine hydrochloride, 4.09 g (11.45 mmol) of 2-dimethylaminomethylene-1,3-bis(dimethylimmonio)propane-bis(tetrafluoroborate) and 3.86 g (34.36 mmol) of potassium tert-butylate in 70 ml of ethanol were heated under reflux for 8 h. After concentration, water and ethyl acetate were added. The organic phase was washed with a potassium hydrogensulfate solution and water, dried and evaporated. Yield: 1.87 g.

(b) 3-[2-(4-Fluoro-phenyl)-pyrimidin-5-yl]-acrylic Acid 945 mg (4.67 mmol) of 2-(4-fluoro-phenyl)-pyrimidine-5-carbaldehyde, 1544 mg (14.84 mmol) of malonic acid and 4197 mg (49.29 mmol) of piperidine in 50 ml of pyridine were stirred at 125° C. for 17 h. After concentration, water and hydrochloric acid were added, and the solid product was filtered off with suction and dried. Yield: 1.01 g.

(c) 3-[2-(4-Fluoro-phenyl)-pyrimidin-5-yl]-N-(thiazol-2-yl)-acrylamide

The compound was prepared as described in Example 116 (d) from 39 mg (0.16 mmol) of 3-[2-(4-fluoro-phenyl)-pyrimidin-5-yl]-acrylic acid, 32 mg (0.32 mmol) of 2-aminothiazole, 267 mg (0.68 mmol) of HATU and 65 mg (0.64 mmol) of triethylamine. Yield: 4 mg.
MS: m/e=327 (M+H)$^+$ Example 133

3-[2-(4-Fluoro-phenyl)-pyrimidin-5-yl]-N-(pyridin-2-yl)-acrylamide

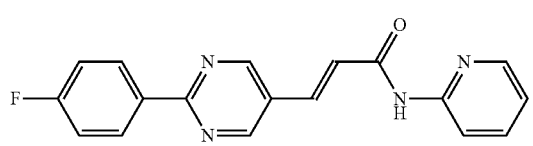

The compound was prepared according to the procedure described in Example 132 using 30 mg (0.32 mmol) of 2-aminopyridine instead of 2-aminothiazole. Yield: 4 mg.
MS: m/e=321 (M+H)$^+$ The N-substituted 3-[2-(4-fluoro-phenyl)-pyrimidin-5-yl]-acrylamides of the formula Ik, which are listed in Table 8, were prepared as described in Example 116(d) from 110 mg (0.45 mmol) of 3-[2-(4-fluoro-phenyl)-pyrimidin-5-yl]-acrylic acid, 0.9 mmol of the respective amine, 171 mg (0.45 mmol) of HATU and 136.7 mg (1.35 mmol) of triethylamine.

TABLE 8

Example compounds of the formula Ik

| Example No. | R$^2$ \ N-R$^1$ | Yield | MS: m/e = |
|---|---|---|---|
| 134 | 4-F-C$_6$H$_4$-NH- | 4.8 mg | 338 (M + H)$^+$ |
| 135 | 2-F-C$_6$H$_4$-NH- | 4.5 mg | 338 (M + H)$^+$ |
| 136 | 2,3-diF-C$_6$H$_3$-NH- | 1.4 mg | 356 (M + H)$^+$ |
| 137 (a) | (CH$_3$)$_2$N- | 4 mg | 272 (M + H)$^+$ |
| 138 | C$_6$H$_5$-NH- | 7.7 mg | 320 (M + H)$^+$ |
| 139 (a) | (C$_2$H$_5$)$_2$N- | 8.7 mg | 300 (M + H)$^+$ |

(a) Dimethylamine and diethylamine were employed in the form of their hydrochloride, and an additional amount of 0.9 mmol of triethylamine was added.

Example 140

N-tert-Butyl-3-[6-(4-fluoro-phenyl)-pyridin-3-yl]-acrylamide, Trifluoroacetic Acid Salt

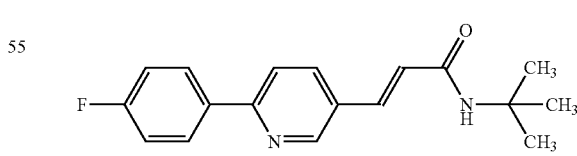

The compound was prepared as described in Example 116 (d) from 200 mg (0.82 mmol) of 3-[6-(4-fluoro-phenyl)-pyridin-3-yl]-acrylic acid, 120.2 mg (1.64 mmol) of tert-butylamine, 312.6 mg (0.82 mmol) of HATU and 332.8 mg (3.29 mmol) of triethylamine. Yield: 163 mg.
MS: m/e=299 (M+H)$^+$

Example 141

3-[1-(4-Fluoro-benzyl)-1H-imidazol-4-yl]-1-(piperidin-1-yl)-propenone, Trifluoroacetic Acid Salt

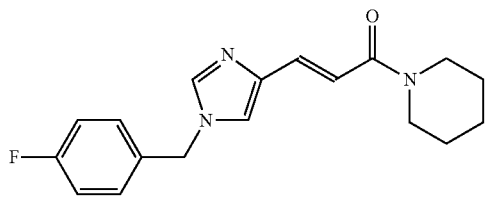

195 mg (4.87 mmol) of sodium hydride were added to 1.00 g (4.87 mmol) of 3-(1H-imidazol-4-yl)-1-(piperidin-1-yl)-propenone in 15 ml of dry DMF, and the mixture was stirred at room temperature for 1 h. Subsequently, 921 mg (4.87 mmol) of 4-fluorobenzyl bromide were added. After stirring at room temperature for 2 h, the mixture was poured onto ice and the resulting precipitate was isolated by filtration. The product was purified by preparative HPLC(RP18, acetonitrile/water, 0.2% TFA). Yield: 320 mg.

MS: m/e=314 (M+H)$^+$

Example 142

3-[1-(2-Chloro-benzyl)-1H-imidazol-4-yl]-1-(piperidin-1-yl)-propenone, Trifluoroacetic Acid Salt

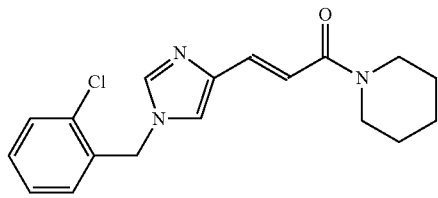

The compound was prepared analogously to Example 141.
MS: m/e=330 (M+H)$^+$

Example 143

3-[1-(5-Methyl-isoxazol-3-ylmethyl)-1H-imidazol-4-yl]-1-(piperidin-1-yl)-propenone, Trifluoroacetic Acid Salt

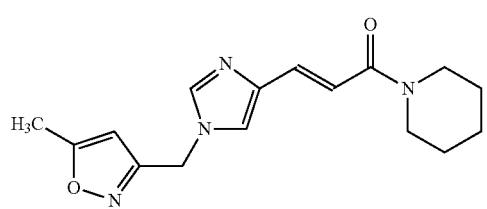

The compound was prepared analogously to Example 141.
MS: m/e=301 (M+H)$^+$

Example 144

3-[6-(4-Fluoro-phenyl)-pyridin-3-yl]-N-(pyridin-2-yl)-acrylamide, Trifluoroacetic Acid Salt

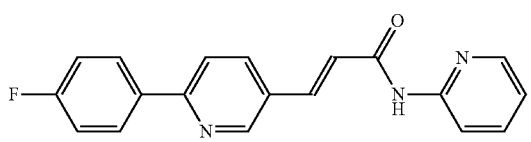

The compound was prepared as described in Example 116 (d) from 200 mg (0.82 mmol) of 3-[6-(4-fluoro-phenyl)-pyridin-3-yl]-acrylic acid, 154.7 mg (1.64 mmol) of 2-aminopyridine, 312.6 mg (0.82 mmol) of HATU and 332.8 mg (3.29 mmol) of triethylamine. Yield: 158 mg.

MS: m/e=320 (M+H)$^+$

Example 145

3-[4-(4-Fluoro-phenyl)-thiazol-2-yl]-N,N-diisopropyl-acrylamide

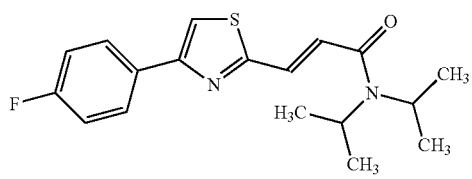

98 mg (0.39 mmol) of 3-[4-(4-fluoro-phenyl)-thiazol-2-yl]-acrylic acid, 79.6 mg (0.78 mmol) of diisopropylamine, 119.35 mg (1.17 mmol) of triethylamine and 164.5 mg (0.43 mmol) of HATU in 5 ml of DMF were stirred at room temperature for 2 h. The reaction mixture was concentrated, and water and ethyl acetate were added. The organic phase was separated, washed and evaporated. The residue was purified by chromatography (RP18). Yield: 39 mg.

MS: m/e=333 (M+H)$^+$

Example 146

N-tert-Butyl-3-[4-(4-fluoro-phenyl)-thiazol-2-yl]-acrylamide

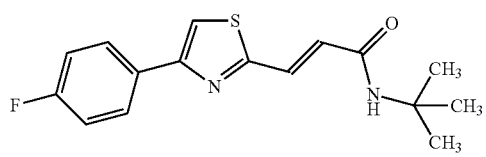

The compound was prepared analogously to Example 145 using 58.7 mg (0.8 mmol) of tert-butylamine instead of diisopropylamine. Yield: 57.6 mg.

MS: m/e=305 (M+H$^+$)

Example 147

N-(2,3-Difluoro-phenyl)-3-(4-(pyridin-4-yl)-thiophen-2-yl)-acrylamide, Trifluoroacetic Acid Salt

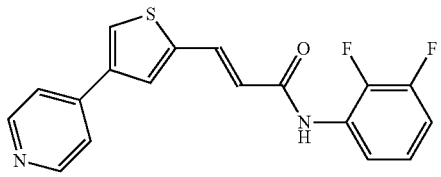

(a) 3-(4-Bromo-thiophen-2-yl)-N-(2,3-difluoro-phenyl)-acrylamide

The compound was prepared analogously to Example 15(a) using 1.0 g (4.29 mmol) of 3-(4-bromo-thiophen-2-yl)-acrylic acid. Yield: 1.31 g.
MS: m/e=344 (M+H)$^+$ (b) N-(2,3-Difluoro-phenyl)-3-(4-(pyridin-4-yl)-thiophen-2-yl)-acrylamide, Trifluoroacetic Acid Salt The compound was prepared analogously to Example 15(b) using 150 mg (0.58 mmol) of 3-(4-bromo-thiophen-2-yl)-N-(2,3-difluoro-phenyl)-acrylamide. Yield: 28.7 mg.
MS: m/e=343 (M+H)$^+$

Example 148

N-(2,3-Difluoro-phenyl)-3-(4-(pyridin-3-yl)-thiophen-2-yl)-acrylamide, Trifluoroacetic Acid Salt

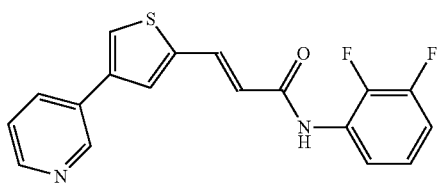

The compound was prepared analogously to Example 15(b) using 150 mg (0.58 mmol) of 3-(4-bromo-thiophen-2-yl)-N-(2,3-difluoro-phenyl)-acrylamide. Yield: 40.2 mg.
MS: m/e=343 (M+H)$^+$

Example 149

N-(2,3-Difluoro-phenyl)-3-[5-(2-fluoro-phenyl)-thiophen-2-yl]-acrylamide

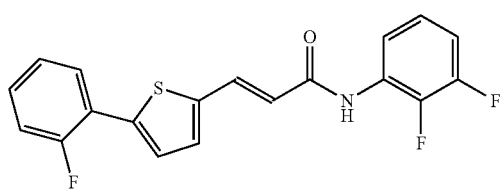

The compound was prepared analogously to Example 4(b) using 150 mg (0.60 mmol) of 3-[5-(2-fluoro-phenyl)-thiophen-2-yl]-acrylic acid. Yield: 38 mg.
MS: m/e=360 (M+H)$^+$

Example 150

3-[5-(2-Fluoro-phenyl)-thiophen-2-yl]-N-phenyl-acrylamide

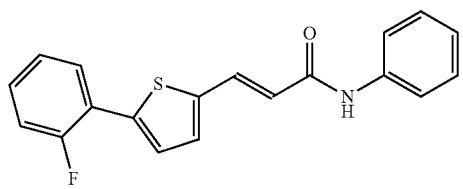

The compound was prepared analogously to Example 4(b) using 150 mg (0.60 mmol) of 3-[5-(2-fluoro-phenyl)-thiophen-2-yl]-acrylic acid. Yield: 63 mg.
MS: m/e=324 (M+H)$^+$

Example 151

3-[6-(2-Fluoro-phenyl)-pyridin-3-yl]-N-(3-pentafluorosulfuranyl-phenyl)-acrylamide

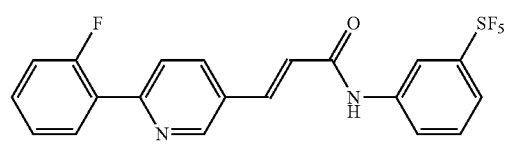

The compound was prepared analogously to Example 2(c) using 100 mg (0.41 mmol) of 3-[6-(2-fluoro-phenyl)-pyridin-3-yl]-acrylic acid. Yield: 68 mg.
MS: m/e=445 (M+H)$^+$

Example 152

3-(5-Chloro-3-methyl-2-phenyl-3H-imidazol-4-yl)-1-(piperidin-1-yl)-propenone

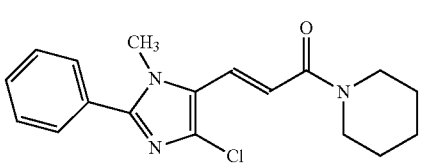

(a) 5-Chloro-3-methyl-2-phenyl-3H-imidazole-4-carbaldehyde 1 g (4.8 mmol) of 5-chloro-2-phenyl-3H-imidazole-4-carbaldehyde, 0.824 g (5.8 mmol) of methyl iodide and 1.338 g (9.7 mmol) of potassium carbonate in 50 ml of DMF were stirred at room temperature for 4 h. The reaction mixture was poured onto 200 ml of water, the resulting mixture stirred for 1 h, and the product was filtered off with suction and dried. Yield: 820 mg.

(b) 3-(5-Chloro-3-methyl-2-phenyl-3H-imidazol-4-yl)-acrylic Acid 2.72 ml of a 1.6 M solution of n-butyllithium in n-hexane (4.4 mmol) were added at 0° C. to a solution of 1.219 g (5.4 mmol) of diethylphosphonoacetic acid ethyl ester in 30 ml of dry THF. After stirring at 0° C. for 30 min, 0.8 g (3.8 mmol) of 5-chloro-3-methyl-2-phenyl-3H-imidazole-4-carbaldehyde in 10 ml of THF were added. The reaction mixture was allowed to stand overnight and then concentrated. The residue was taken up in 100 ml of ethyl acetate, and the solution washed three times with 30 ml each of a sodium hydrogencarbonate solution, dried with magnesium sulfate and evaporated. The obtained crude 3-(5-chloro-3-methyl-2-phenyl-3H-imidazol-4-yl)-acrylic acid ethyl ester was stirred in 5.4 ml of 1 N sodium hydroxide solution and 20 ml of tert-butanol at room temperature for 24 h. After concentration, 10 ml of water were added, and the mixture was acidified to pH=5 with hydrochloric acid. The mixture was stirred for 1 h, and the precipitated product was filtered off with suction and dried.

(c) 3-(5-Chloro-3-methyl-2-phenyl-3H-imidazol-4-yl)-1-(piperidin-1-yl)-propenone 0.69 g (2.6 mmol) of 3-(5-chloro-3-methyl-2-phenyl-3H-imidazol-4-yl)-acrylic acid, 0.268 g (3.2 mmol) of piperidine, 1.034 g (3.2 mmol) of TOTU and 0.407 mg (3.2 mmol) of ethyldiisopropylamine in 5 ml of dry DMF were stirred at room temperature for 18 h. The mixture was diluted with 10 ml of ethyl acetate, washed two times with 5 ml each of a sodium carbonate solution and two times with 5 ml each of a sodium hydrogensulfate solution, dried with magnesium sulfate and evaporated. Yield: 0.55 g.

MS: m/e=330 (M+H)$^+$

Determination of the Biological Activity

A) Activation of eNOS Transcription

Activation of eNOS transcription was measured as described in detail by L[1] et al., "Activation of protein kinase C alpha and/or epsilon enhances transcription of the human endothelial nitric oxide synthase gene", Mol. Pharmacol. 53 (1998) 630. Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with the compounds.

All compounds were dissolved in sterile dimethyl sulfoxide (DMSO). A final concentration of 0.5% DMSO in complete medium was allowed. Induction of reporter gene expression in these cells was measured using a standard luciferase assay system (Promega, Cat. No. E150) according to the manufacturer's instructions. Luciferase induction in cells incubated with compounds were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. $EC_{50}$ values of transcription induction ratios as a function of compound concentration were determined graphically.

Numerous compounds of the instant invention were tested by the above-described assay and found to increase protein transcription. Generally, the tested compounds exhibited $EC_{50}$ values of less than about 50 μM. Preferred compounds, including the compounds of examples 1, 13, 21, 50, 56, 76, 116, 123, 125, 150, for example, exhibited $EC_{50}$ values of from about 5 μM to about 0.5 μM. More preferred compounds, including the compounds of examples 5, 15, 32, 44, 63, 105, 110, 119, 145, 146, for example, exhibited $EC_{50}$ values of less than about 0.5 μM.

The effect of compounds on eNOS-transcription was confirmed in a second assay based on eNOS protein detection. Primary human umbilical vein cord endothelial cells (HUVEC) were isolated and cultivated according to standard procedures. Confluent cells were incubated with compounds for 18 h and the effect on eNOS protein expression determined by a quantitative Western blotting procedure. After compound incubation, HUVEC were lysed in ice-cold lysis buffer containing 10 mM Tris-HCl, pH 8.0, 1% SDS and protease inhibitors. The lysate was subjected to a standard denaturating polyacrylamide gel electrophoresis and blotted to nitrocellulose membranes. Using a specific primary monoclonal antibody (Transduction Laboratories, UK) and alkaline phosphatase labelled secondary antibody (Jackson Labs), a specific eNOS protein band was visualized and quantified based on a chemifluorescence detection method.

The effect of the compounds of the formulae I and Ia can also be investigated in the following animal models (animal experiments are performed in accordance with the German animal protection law and the guidelines for the use of experimental animals as given by the Guide for the Care and Use of Laboratory Animals of the US National Institutes of Health).

Animals and Treatment (Experiments B-D)

ApoE and eNOS deficient mice (C57BL/6J background, Jackson Laboratory, Bar Harbor, Me.) are used. All animals are 10 to 12 weeks of age and weigh 22 to 28 g. Three days before surgery mice are divided into 4 groups (apoE control, n=10 to 12; apoE with test compounds, n=10 to 12; eNOS control, n=10 to 12; eNOS with test compounds, n=10 to 12) and receive either a standard rodent chow (containing 4% of fat and 0.001% of cholesterol; in the following designated as placebo group) or a standard rodent chow+test compound (10 or 30 mg/kg/day p.o.).

B) Anti-Hypertensive Effect in ApoE Knockout Mice

Blood-pressure is determined in conscious mice using a computerized tail-cuff system (Visitech Systems, Apex, Nc). After treatment of ApoE deficient mice and eNOS deficient mice with the test compounds the blood pressure is compared to the results obtained with a placebo treatment.

C) Inhibition of Neointima Formation and Atherogenesis (Femoral Artery Cuff)

After 3 day treatment of ApoE deficient mice with the respective compound (10 mg/kg/day pressed in chow), animals are anesthetized with an intraperitoneal injection of pentobarbital (60 mg/kg) followed by an intramuscular injection of xylazin (2 mg/kg) and a cuff is placed around the femoral artery as described in Moroi et al. (J. Clin. Invest. 101 (1998) 1225). Briefly, the left femoral artery is dissected. A non-occlusive 2.0 mm polyethylene cuff made of PE 50 tubing (inner diameter 0.56 mm, outer diameter 0.965 mm, Becton Dickinson, Mountain View, Calif.) is placed around the artery and tied in place with two 7-0 sutures. The right femoral artery is isolated from the surrounding tissues but a cuff is not placed. Treatment with the respective compound is continued for 14 days after surgery. Then the animals are sacrificed. The aorta are taken for determination of vascular eNOS expressions by quantitative western blotting. Both femoral arteries are harvested, fixed in formalin and embedded in paraffin. 20 cross sections (10 μm) are cut from the cuffed portion of the left femoral artery and from the corresponding segment of the right artery. Sections are subjected to standard hematoxylin and eosin staining. Morphometric analyses are performed using an image analysis computer program (LeicaQWin, Leica Imaging Systems, Cambridge, GB). For each cross section the area of the lumen, the neointima and the media are determined. To this end, the neointima is defined as the area between the lumen and the internal elastic lamina and the media is defined as the area between the internal and the external elastic lamina. The ratio between the area of the neointima and the area of the media is expressed as the neointima/media ratio. The results obtained in the compound group are compared to those obtained in the placebo group.

D) Prevention of Atherosclerotic Plaque Formation in Chronic Treatment

ApoE deficient mice are treated for 16 weeks with the respective compound pressed in chow and finally sacrificed. Aortas are removed from each mouse, fixed in formalin and embedded in paraffin. Plaque formation is measured via lipid lesions formation in the aortas (from aortic arch to diaphragm) and is analyzed by oil red O staining. For quantifying the effect of the respective compound on vascular eNOS expression the femoral arteries are used in this experiment. The results obtained in the compound group are compared to those obtained in the placebo group.

E) Improvement of Coronary Function in Diseased ApoE Deficient Mice

Old Male wild-type C57BL/6J mice (Charles River Wiga GmbH, Sulzfeld), and apoE deficient mice (C57BL/6J background, Jackson Laboratory, Bar Harbor, Me.) of 6 month of age and weighing 28 to 36 g are used in the experiments. Mice are divided into 3 groups (C57BL/6J, n=8; apoE control, n=8; apoE with respective compound, n=8) and receive for 8 weeks either a standard rodent chow (containing 4% of fat and 0.001% of cholesterol) or a standard rodent chow+respective compound (30 mg/kg/day p.o.). Mice are anesthetized with sodium pentobarbitone (100 mg/kg i.p.), and the hearts are rapidly excised and placed into ice-cold perfusion buffer. The aorta is cannulated and connected to a perfusion apparatus (Hugo Sachs Electronics, Freiburg, Germany) which is started immediately at a constant perfusion pressure of 60 mm Hg. Hearts are perfused in a retrograde fashion with modified Krebs bicarbonate buffer, equilibrated with 95% $O_2$ and 5% $CO_2$ and maintained at 37.5° C. A beveled small tube (PE 50) is passed through a pulmonary vein into the left ventricle and pulled through the ventricular wall, anchored in the apex by a fluted end, and connected to a tip-micromanometer (Millar 1.4 French). The left atrium is cannulated through the same pulmonary vein and the heart switched to the working mode with a constant preload pressure of 10 mm Hg and an afterload pressure of 60 mm Hg. Aortic outflow and atrial inflow are continuously measured using ultrasonic flow probes (HSE/Transonic Systems Inc.). Coronary flow is calculated as the difference between atrial flow and aortic flow. All hemodynamic data are digitized at a sampling rate of 1000 Hz and recorded with a PC using specialized software (HEM, Notocord).

Hearts are allowed to stabilize for 30 min. All functional hemodynamic data are measured during steady state, and during volume and pressure loading. Left ventricular function curves are constructed by varying pre-load pressure. For acquisition of preload curves, afterload is set at 60 mm Hg and preload is adjusted in 5 mm Hg steps over a range of 5 to 25 mm Hg. Hearts are allowed to stabilize at baseline conditions between pressure and volume loading.

We claim:
1. A compound of the formula I,

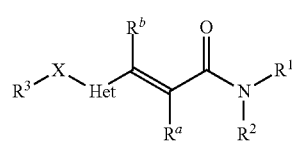

in which

Het is pyridinediyl, which can be substituted on ring carbon atoms by one or more identical or different substituents $R^5$;

X is selected from a direct bond, $CH_2$, O and NH, provided that X cannot be O or NH if the group $R^3$—X— is bonded to a ring nitrogen atom of the group Het;

$R^a$ and $R^b$ are independently of each other selected from hydrogen and $(C_1-C_4)$-alkyl;

$R^1$ and $R^2$ are independently of each other selected from hydrogen, $(C_1-C_6)$-alkyl, $(C_3-C_6)$-alkenyl, $(C_3-C_6)$-alkynyl, $(C_3-C_7)$-cycloalkyl-$C_nH_{2n}$—, phenyl-$C_nH_{2n}$— and heteroaryl-$C_nH_{2n}$—, wherein the groups $(C_1-C_6)$-alkyl, $(C_3-C_7)$-cycloalkyl, $(C_3-C_6)$-alkenyl and $(C_3-C_6)$-alkynyl can all be substituted by one or more identical or different substituents $R^6$, and the groups $C_nH_{2n}$ can all be substituted by one or more identical or different substituents selected from fluorine and $(C_1-C_4)$-alkyl, and all phenyl and heteroaryl groups can independently of each other be substituted on carbon atoms by one or more identical or different substituents $R^7$, or $R^1$ and $R^2$, together with the nitrogen atom carrying them, form a 4-membered to 7-membered monocyclic, saturated or unsaturated ring which, in addition to the ring nitrogen atom carrying $R^1$ and $R^2$, can contain one or two further heteroatom ring members selected from N, $NR^9$, O, S, SO and $SO_2$ which can be identical or different, with the proviso that two ring members from the series O, S, SO and $SO_2$ cannot be present in adjacent ring positions, wherein the ring formed by $R^1$ and $R^2$ together with the nitrogen atom carrying them can be substituted on ring carbon atoms by one or more identical or different substituents $R^8$;

$R^3$ is selected from phenyl, pyridinyl, isoxazolyl, and thiofuranyl which can all be substituted by one or more identical or different substituents selected from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_3)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN, $CF_3$, $H_2NSO_2$— and $(C_1-C_4)$-alkyl-$SO_2$—, wherein heteroaryl representing $R^3$ is bonded to the group X-Het via a ring carbon atom;

$R^5$ is selected from $(C_1-C_4)$-alkyl, OH, $(C_1-C_4)$-alkylmercapto, $NH_2$, $(C_1-C_4)$-alkylamino, di$((C_1-C_4)$-alkyl)

amino, $((C_1-C_4)$-alkyl$)$-CONH—, di$((C_1-C_4)$-alkyl$)$ aminocarbonyl-, $((C_1-C_4)$-alkyl$)$aminocarbonyl-, $((C_1-C_4)$-alkyloxy$)$carbonyl-, CONH$_2$, CN, CF$_3$ and $(C_1-C_4)$-alkyl-SO$_2$—;

R$^6$ is selected from fluorine, OH, oxo, $(C_1-C_4)$-alkyloxy, $(C_1-C_4)$-alkylmercapto, di$((C_1-C_4)$-alkyl$)$amino, $((C_1-C_4)$-alkyl$)$-CONH—, di$((C_1-C_4)$-alkyl$)$aminocarbonyl-, $((C_1-C_4)$-alkyl$)$aminocarbonyl-, $((C_1-C_4)$-alkyloxy$)$carbonyl-, CONH$_2$, CN and CF$_3$;

R$^7$ is selected from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_3)$-alkylenedioxy which can be substituted by one or more fluorine atoms, $(C_1-C_4)$-alkylmercapto, NH$_2$, $(C_1-C_4)$-alkylamino, di$((C_1-C_4)$-alkyl$)$amino, $((C_1-C_4)$-alkyl$)$-CONH—, di$((C_1-C_4)$-alkyl$)$aminocarbonyl-, $((C_1-C_4)$-alkyl$)$aminocarbonyl-, $((C_1-C_4)$-alkyloxy$)$carbonyl-, CONH$_2$, CN, CF$_3$, SF$_5$, H$_2$NSO$_2$— and $(C_1-C_4)$-alkyl-SO$_2$—;

R$^8$ is selected from fluorine, $(C_1-C_4)$-alkyl, $(C_1-C_4)$-alkyloxy-$(C_1-C_2)$-alkyl-, OH, oxo, $(C_1-C_4)$-alkyloxy which can be substituted by one or more fluorine atoms, $(C_1-C_3)$-alkylenedioxy, $(C_1-C_4)$-alkylmercapto, NH$_2$, $(C_1-C_4)$-alkylamino, di$((C_1-C_4)$-alkyl$)$amino, $((C_1-C_4)$-alkyl$)$-CONH—, di$((C_1-C_4)$-alkyl$)$aminocarbonyl-, $((C_1-C_4)$-alkyl$)$aminocarbonyl-, $((C_1-C_4)$-alkyloxy$)$carbonyl-, CONH$_2$, CN and CF$_3$;

R$^9$ is selected from hydrogen, $(C_1-C_4)$-alkyl, $((C_1-C_4)$-alkyl$)$-CO— and phenyl-CO—, wherein the phenyl group can be substituted by one or more identical or different substituents selected from halogen, $(C_1-C_4)$-alkyl, CF$_3$ and $(C_1-C_4)$-alkyloxy;

R$^{10}$ is selected from hydrogen and $(C_1-C_4)$-alkyl;

heteroaryl is a 5-membered or 6-membered, monocyclic aromatic group which contains one, two or three identical or different heteroatom ring members selected from N, NR$^{10}$, O and S; and n is 0, 1 or 2, where all numbers n are independent of each other and can be identical or different;

in any of its stereoisomeric forms or a mixture of stereoisomeric forms in any ratio, or a physiologically acceptable salt thereof;

provided that R$^1$ and R$^2$, together with the nitrogen atom carrying them, cannot be a piperidin-1-yl group if simultaneously R$^a$ and R$^b$ are hydrogen and the group R$^3$—X—Het- is 6-(2,6-diethylphenyl)-4-ethyl-2-methyl-pyridin-3-yl; and provided that R$^1$ cannot be 2-aminophenyl when R$^a$, R$^b$, and R$^2$ are hydrogen and the group R$^3$—X—Het is 6-(3,4-dimethoxyphenyl)pyridin-3-yl.

2. A compound as claimed in claim 1, in which R$^1$ is selected from $(C_1-C_4)$-alkyl, $(C_3-C_7)$-cycloalkyl-C$_n$H$_{2n}$—, phenyl-C$_n$H$_{2n}$— and heteroaryl-C$_n$H$_{2n}$—, and R$^2$ is selected from hydrogen and $(C_1-C_4)$-alkyl, wherein all $(C_1-C_4)$-alkyl and $(C_3-C_7)$-cycloalkyl groups can be substituted by one or more identical or different substituents R$^6$, and all phenyl and heteroaryl groups can be substituted by one or more identical or different substituents R$^7$, or R$^1$ and R$^2$, together with the nitrogen atom carrying them, form a 4-membered to 7-membered monocyclic, saturated ring which, in addition to the ring nitrogen atom carrying R$^1$ and R$^2$, can contain one further heteroatom ring member selected from NR$^9$, O, S, SO and SO$_2$, wherein the ring formed by R$^1$ and R$^2$ and the nitrogen atom carrying them can be substituted by one or more identical or different substituents R$^8$;

or a physiologically acceptable salt thereof.

3. A compound as claimed in claim 1, in which R$^3$ is selected from phenyl, pyridinyl, isoxazolyl and thiofuranyl, which can all be substituted by one or more identical or different substituents selected from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl$)$amino, CONH$_2$, CN, CF$_3$ and $(C_1-C_4)$-alkyl-SO$_2$—; or a physiologically acceptable salt thereof.

4. A compound as claimed in claim 3, in which R$^3$ is phenyl which can be substituted by one or more identical or different substituents selected from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl$)$amino, CONH$_2$, CN, CF$_3$ and $(C_1-C_4)$-alkyl-SO$_2$—; or a physiologically acceptable salt thereof.

5. A compound as claimed in claim 1, in which X is selected from a direct bond and O; or a physiologically acceptable salt thereof.

6. A compound as claimed in claim 1, in which R$^3$ is phenyl which can be substituted by one or more identical or different substituents selected from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl$)$amino, CONH$_2$, CN, CF$_3$ and $(C_1-C_4)$-alkyl-SO$_2$—; and X is selected from a direct bond and O;

or a physiologically acceptable salt thereof.

7. A compound as claimed in claim 1, in which

R$^3$ is selected from phenyl, pyridinyl, isoxazolyl and thiofuranyl, which can all be substituted by one or more identical or different substituents selected from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl$)$amino, CONH$_2$, CN, CF$_3$ and $(C_1-C_4)$-alkyl-SO$_2$—; and X is selected from a direct bond and O;

or a physiologically acceptable salt thereof.

8. A process for the preparation of a compound as claimed in claim 1, or a physiologically acceptable salt thereof, comprising reacting a compound of the formula IV and a compound of the formula V,

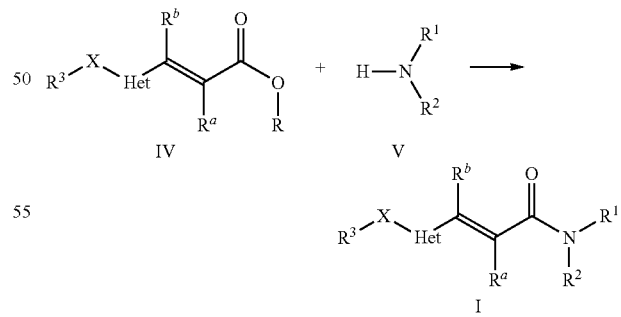

wherein Het, X, R$^a$, R$^b$, R$^1$, R$^2$ and R$^3$ are defined as in claim 1 and, in addition, any functional groups can be present in protected form or in the form of precursor groups, and R is hydrogen, $(C_1-C_4)$-alkyl or benzyl.

9. A pharmaceutical composition, comprising at least one compound as claimed in claim 1, or a physiologically acceptable salt thereof, and a pharmaceutically acceptable carrier.

10. A method of treating a patient for a condition that responds to the stimulation of the expression of endothelial NO synthase, the method comprising administering to the patient a pharmaceutically effective dose of a compound according to claim 1.

11. The method according to claim 10, wherein the condition is selected from stable or unstable angina pectoris, coronary heart disease, coronary artery disease, Prinzmetal angina, acute coronary syndrome, cardiac insufficiency, heart failure, myocardial infarction, stroke, thrombosis, peripheral artery occlusive disease, endothelial dysfunction, atherosclerosis, restenosis, endothelial damage after PTCA, hypertension, essential hypertension, pulmonary hypertension, secondary hypertension, renovascular hypertension, chronic glomerulonephritis, erectile dysfunction, ventricular arrhythmia, diabetes, diabetes complications, nephropathy, retinopathy, angiogenesis, asthma bronchiale, chronic renal failure, cirrhosis of the liver, osteoporosis, and restricted memory.

\* \* \* \* \*